(12) United States Patent
Barolet et al.

(10) Patent No.: US 7,887,533 B2
(45) Date of Patent: Feb. 15, 2011

(54) DEVICE FOR THE TREATMENT OF MAMMALIAN TISSUES

(75) Inventors: Daniel Barolet, Rosemere (CA); Mathieu Auclair, Laval (CA); Annie Boucher, Montreal (CA)

(73) Assignee: Clinique Dr Daniel Barolet Inc., Town of Mount Royal, Quebec (CA)

( * ) Notice: Subject to any disclaimer, the term of this patent is extended or adjusted under 35 U.S.C. 154(b) by 29 days.

(21) Appl. No.: 11/976,921

(22) Filed: Oct. 30, 2007

(65) Prior Publication Data
US 2008/0108982 A1    May 8, 2008

Related U.S. Application Data

(63) Continuation of application No. 11/053,603, filed on Feb. 7, 2005.

(60) Provisional application No. 60/541,936, filed on Feb. 6, 2004.

(51) Int. Cl.
*A61N 5/06* (2006.01)
(52) U.S. Cl. .................. 606/9; 606/2; 606/10
(58) Field of Classification Search .......... 606/1, 606/39, 51
See application file for complete search history.

(56) References Cited

U.S. PATENT DOCUMENTS

| | | | | |
|---|---|---|---|---|
| 2,315,786 | A * | 4/1943 | Grobe | 378/196 |
| 3,803,418 | A * | 4/1974 | Holstrom | 378/177 |
| 4,440,160 | A | 4/1984 | Fischell et al. | |
| 4,458,678 | A | 7/1984 | Yannas et al. | |
| 4,622,971 | A * | 11/1986 | Yamamoto et al. | 606/2 |
| 4,646,743 | A | 3/1987 | Parris | |
| 4,669,466 | A | 6/1987 | L'Esperance | |
| 4,767,402 | A | 8/1988 | Kost et al. | |
| 4,836,203 | A | 6/1989 | Muller et al. | |
| 4,888,354 | A | 12/1989 | Chang et al. | |
| 4,930,504 | A | 6/1990 | Diamantopoulos et al. | |

(Continued)

FOREIGN PATENT DOCUMENTS

GB        2333962        8/1999

(Continued)

OTHER PUBLICATIONS

Parrish, John et al., Cutaneous Laser Therapy: Principles and Methods; edited by K. A. Arndt et al; 1983; pp. 41-52; Considerations of Selectivity in Laser Therapy [full article enclosed].

(Continued)

*Primary Examiner*—Henry M Johnson, III
*Assistant Examiner*—Jeffrey B Lipitz
(74) *Attorney, Agent, or Firm*—McDermott Will & Emery LLP

(57) ABSTRACT

A photoactivation device for modulating the physiology of a target biological activity by directing a photoactivating beam of light having a predetermined set of photoactivating light parameters on a target surface, the device comprising:
  a photoactivating light source for emitting the photoactivating beam of light;
  a positioning means operatively coupled to the photoactivating light source for allowing selective positioning of the photoactivating light source relative to the target surface;
  a position evaluating means for evaluating the position of the photoactivating light source relative to the target surface.

19 Claims, 33 Drawing Sheets

U.S. PATENT DOCUMENTS

| | | | |
|---|---|---|---|
| 4,969,912 A | 11/1990 | Kelman et al. | |
| 4,973,848 A | 11/1990 | Kolobanov et al. | |
| 5,021,452 A | 6/1991 | Labbe et al. | |
| 5,037,432 A | 8/1991 | Molinari | |
| 5,147,349 A | 9/1992 | Johnson et al. | |
| 5,198,465 A | 3/1993 | Dioguardi | |
| 5,226,907 A | 7/1993 | Tankovich | |
| 5,231,975 A | 8/1993 | Bommannan et al. | |
| 5,259,380 A | 11/1993 | Mendes et al. | |
| 5,266,480 A | 11/1993 | Naughton et al. | |
| 5,312,396 A | 5/1994 | Feld et al. | |
| 5,320,619 A | 6/1994 | Badawi | |
| 5,332,802 A | 7/1994 | Kelman et al. | |
| 5,358,503 A | 10/1994 | Bertwell et al. | |
| 5,366,498 A | 11/1994 | Brannan et al. | |
| 5,397,352 A | 3/1995 | Burres | |
| 5,409,479 A | 4/1995 | Dew et al. | |
| 5,423,803 A | 6/1995 | Tankovich et al. | |
| 5,425,728 A | 6/1995 | Tankovich | |
| 5,445,146 A | 8/1995 | Bellinger | |
| 5,445,634 A | 8/1995 | Keller | |
| 5,460,939 A | 10/1995 | Hansbrough et al. | |
| 5,474,528 A | 12/1995 | Meserol | |
| 5,489,758 A | 2/1996 | Nihei et al. | |
| 5,492,135 A | 2/1996 | DeVore et al. | |
| 5,501,680 A | 3/1996 | Kurtz et al. | |
| 5,549,660 A | 8/1996 | Mendes et al. | |
| 5,591,444 A | 1/1997 | Boss, Jr. | |
| 5,620,478 A | 4/1997 | Eckhouse | |
| 5,638,593 A | 6/1997 | Gerhardt et al. | |
| 5,643,334 A | 7/1997 | Eckhouse et al. | |
| 5,647,866 A | 7/1997 | Zaias et al. | |
| 5,674,217 A | 10/1997 | Washlstrom et al. | |
| 5,735,285 A | 4/1998 | Albert et al. | |
| 5,755,751 A | 5/1998 | Eckhouse | |
| 5,807,387 A * | 9/1998 | Druais | 606/10 |
| 5,968,034 A | 10/1999 | Fullmer et al. | |
| 6,015,404 A | 1/2000 | Altshuler et al. | |
| 6,050,990 A | 4/2000 | Tankovich et al. | |
| 6,063,108 A | 5/2000 | Salansky et al. | |
| 6,077,294 A | 6/2000 | Cho et al. | |
| 6,096,066 A | 8/2000 | Chen et al. | |
| 6,171,332 B1 | 1/2001 | Whitehust | |
| 6,187,029 B1 | 2/2001 | Shapiro et al. | |
| 6,221,095 B1 | 4/2001 | Van Zuylen et al. | |
| 6,251,102 B1 | 6/2001 | Gruzdev et al. | |
| 6,251,127 B1 | 6/2001 | Biel | |
| 6,283,956 B1 | 9/2001 | McDaniel | |
| 6,387,089 B1 | 5/2002 | Kreindel et al. | |
| 6,406,474 B1 | 6/2002 | Neuberger et al. | |
| 6,413,267 B1 | 7/2002 | Dumoulin-White et al. | |
| 6,488,697 B1 | 12/2002 | Ariura et al. | |
| 6,494,900 B1 | 12/2002 | Salansky et al. | |
| 6,530,921 B1 * | 3/2003 | Maki | 606/15 |
| 6,592,611 B1 | 7/2003 | Zawada | |
| 6,595,986 B2 | 7/2003 | Almeida | |
| 6,602,275 B1 | 8/2003 | Sullivan | |
| 6,645,230 B2 | 11/2003 | Whitehurst | |
| 6,652,512 B2 | 11/2003 | Ota | |
| 6,660,000 B2 | 12/2003 | Neuberger et al. | |
| 6,663,659 B2 | 12/2003 | McDaniel | |
| 6,676,655 B2 | 1/2004 | McDaniel | |
| 6,689,124 B1 | 2/2004 | Thiberg | |
| 6,709,446 B2 | 3/2004 | Lundahl et al. | |
| 6,718,128 B2 | 4/2004 | Meyer et al. | |
| 6,746,444 B2 | 6/2004 | Key | |
| 6,749,602 B2 | 6/2004 | Sierra et al. | |
| 6,758,845 B1 | 7/2004 | Weckwerth et al. | |
| 6,835,202 B2 * | 12/2004 | Harth et al. | 607/91 |
| 6,887,260 B1 | 5/2005 | McDaniel | |
| 6,902,563 B2 | 6/2005 | Wilkens et al. | |
| 6,975,404 B2 * | 12/2005 | Schwarz | 356/446 |
| 7,033,349 B2 | 4/2006 | Key | |
| 2001/0023363 A1 | 9/2001 | Harth et al. | |
| 2001/0053907 A1 | 12/2001 | Ota | |
| 2002/0095143 A1 * | 7/2002 | Key | 606/9 |
| 2002/0120312 A1 | 8/2002 | Ignatius et al. | |
| 2002/0123782 A1 | 9/2002 | Sierra et al. | |
| 2002/0128695 A1 * | 9/2002 | Harth et al. | 607/88 |
| 2002/0167669 A1 * | 11/2002 | Schwarz | 356/446 |
| 2003/0004556 A1 * | 1/2003 | McDaniel | 607/88 |
| 2003/0032950 A1 | 2/2003 | Altshuler et al. | |
| 2003/0130649 A1 | 7/2003 | Murray et al. | |
| 2003/0208245 A1 | 11/2003 | Mahadevan-Jansen et al. | |
| 2003/0216719 A1 | 11/2003 | Debenedictis et al. | |
| 2004/0093042 A1 | 5/2004 | Altshuler et al. | |
| 2004/0093043 A1 * | 5/2004 | Edel et al. | 607/88 |
| 2004/0122492 A1 * | 6/2004 | Harth et al. | 607/88 |
| 2004/0162549 A1 * | 8/2004 | Altshuler | 606/9 |
| 2004/0199152 A1 | 10/2004 | Key | |
| 2005/0045189 A1 | 3/2005 | Jay | |
| 2005/0143792 A1 | 6/2005 | Jay | |

FOREIGN PATENT DOCUMENTS

| | | |
|---|---|---|
| RU | 1724269 A1 | 4/1992 |
| WO | WO-03/001984 A2 | 1/2003 |
| WO | WO 2004-043543 | 5/2004 |

OTHER PUBLICATIONS

Whelan, Harry T., M.D. et al.; "Effect of NASA Light-Emitting Diode Irradiation on Wound Healing", Journal of Clinical Laser Medicine & Surgery, vol. 19, No. 6, 2001, pp. 305-314.

McDaniel, David H. MD. et al.; "Treatment of Stretch Marks with the 585-nm Flashlamp-pumped Pulsed Dye Laser", The American Society for Dermatology, Surgery, Inc., Published by Elsevier Science Inc., 1996, pp. 332-337.

Gupta, Adity A. K., M.D. et al., "The Use of Low Energy Photon Therapy (LEPT) in Venous Leg Ulcers: a Double-Blind, Placebo-Controlled Study", The American Society for Dermatology Surgery, Inc., Published by Elsevier Science Inc., 1998, pp. 1383-1386.

Gupta, A. K. et al., "The Use of Low-Energy Photon Therapy in the Treatment of Leg Ulcers—A Preliminary Study", Journal of Dermatological Treatment; 1997, pp. 103-108.

Kubasova, T. et al., "Biological Effect of He-Ne Laser: Investigations on Functional and Micromorphological Alterations of Cell Membranes, In Vitro", Lasers Surg Med. 1984; 4(4); pp. 381-388.

Abergel, R. P. et al., "Control of Connective Tissue Metabolism by Lasers: Recent Developments and Future Prospects", Journal of American Acad Dermatol, 1984, pp. 1142-1150.

Hallman, H. O. et al., "Does Low-Energy Helium-Neon Laser Irradiation Alter "In Vitro"Replication of Human Fibroblasts?", Lasers Surg Med. 1988, pp. 125-129.

Soudry, M. et. al., "Effect of Helium-Neon Laser on Cellular Growth: An In Vitro Study of Human Gingival Fibroblasts", J Biol Buccale, 1988, pp. 129-135.

Balboni et al., "Effect of Laser Irradiation on Collagen Production by Fibrolasts In Vitro", Bull Assoc Anat (Nancy), Mar. 1985 69(204): 15-8.

Yu W., et al., "Effects of Photostimulation on Wound Healing in Diabetic Mice", Laserts Surg Med. 1997;20(1): pp. 56-63.

Hashieh, et al., "Helium-Neon Laser Irradiation Is Not A Stressful Treatment: A Study on Heat-Shock Protein (HSP70) Level", Lasers Surg. Med., 1997; 20(4): pp. 451-460.

Yamamoto et al., "Effect of Low-Power Laser Irradiation on Procollagen Synthesis in Human Fibroblasts", J Clin Laser Med Surg., 1996, Jun. 14(3):,pp. 129-32.

Bosatra et al., "In Vitro Fibroblast and Dermis Fibroblast Activation by Laser Irradiation At Low Energy. An Electron Microscopic Study", Dermatologica, 1984;68(4), pp. 157-162.

Kim YG et al., "Hairless Mouse Epidermal Antioxidants and Lipid Peroxidation Assessed by He-Ne Laser", Lasers Surg Med. 2000;27(5), pp. 420-426.

E. J. Neiburger, "Rapid Healing of Gingival Incisions by the Helium-Neon Diode Laser", J Mass Dent Soc, 1999 Spring;48(1): 8-13, p. 40.

Labbe R.F., et al., "Laser Photobioactivation Mechanisms: In Vitro Studies Using Ascorbic Acid Uptake and Hydroxyproline Formation As Biochemical Markers of Irradiation Response", Lasers Surg Med. 1990;10(2): pp. 201-207.

Pereira A.N., et al., "Effect of Low-Power Laser Irradiation on Cell Growth and Procollagen Synthesis of Cultured Fibroblasts", Lasers Surg Med 2002;31(4): pp. 263-267.

Almeida-Lopes L., et al., "Comparison of the Low Level Laser Therapy Effects on Cultured Human Gingival Fibroblasts Proliferation Using Different Irradiance and Same Fluence", Lasers Surg Med. 2001;29(2): pp. 179-184.

Colver G.B. et al., "Failure of a Helium-Neon Laser to Affect Components of Wound Healing in Vitro", Br J Dermatol, Aug. 1989 121(2): pp. 179-186.

Webb C. et al., "Stimulatory Effrect of 660 nm low Level Laser Energy on Hypertrophic Scar-Derived Fibroblasts: Possible Mechanisms for Increase in Cell Counts", Lasers Surg Med., 1998; 22(5): pp. 294-301.

Sommer, Andrei P. et al., "Biostimulatory Windows in Low-Intensity Laser Activation: Lasers, Scanners, and NASA's Light Emitting Diode Array Systerm", journal of Clinical Laser Medicine & Surgery, vol. 19, No. 1, 2001, pp. 29-33.

Nussbaum, Ethne L. et al.; "Comparison of Ultrasound/Ultraviolet-C and Laser for Treatment of Pressure Ulcers in Patients With Spinal Cord Injury"; Physical Therapy, vol. 74, No. 9/Sep. 1994; pp. 812-825.

van Breugel HH, et al., "Power Density and Exposure Time of He-Ne Laser Irradiation Are More Important Than Total Energy Dose in Photo-Biomodulation of Human Fibroblasts in Vitro", Lasers Surg Med., 1992;12(5): pp. 528-537.

Wong-Riley et al., "Light-Emiting Diode Treatment reverses the Effect of TTX on Cytochrome Oxidase in Neurons", Neurochemistry, 2001, vol. 12 (14 8), pp. 3033-3037.

Whelan, Harry T., et al., "NASA Light Emiting Diode Medical Applications From Deep Space to Deep Sea", Space Technology and Applications International Forum, 2001, pp. 35-45.

Loevschall, et al., "Effect of Low Level Diode Laser Irradiation of Human Oral Mucosa Fibroblasts in Vitro", Lasers Surg Med. 1994; 14(4): pp. 347-354.

Whelan, Harry, T, " Medical Applications of Space Light-Emitting Diode Technology—Space Station and Beyond", Space Technology and Applications International Forum—1999, pp. 3-15.

Office Action dated Jul. 1, 2010 in counterpart JP Application No. 2006-551698.

* cited by examiner

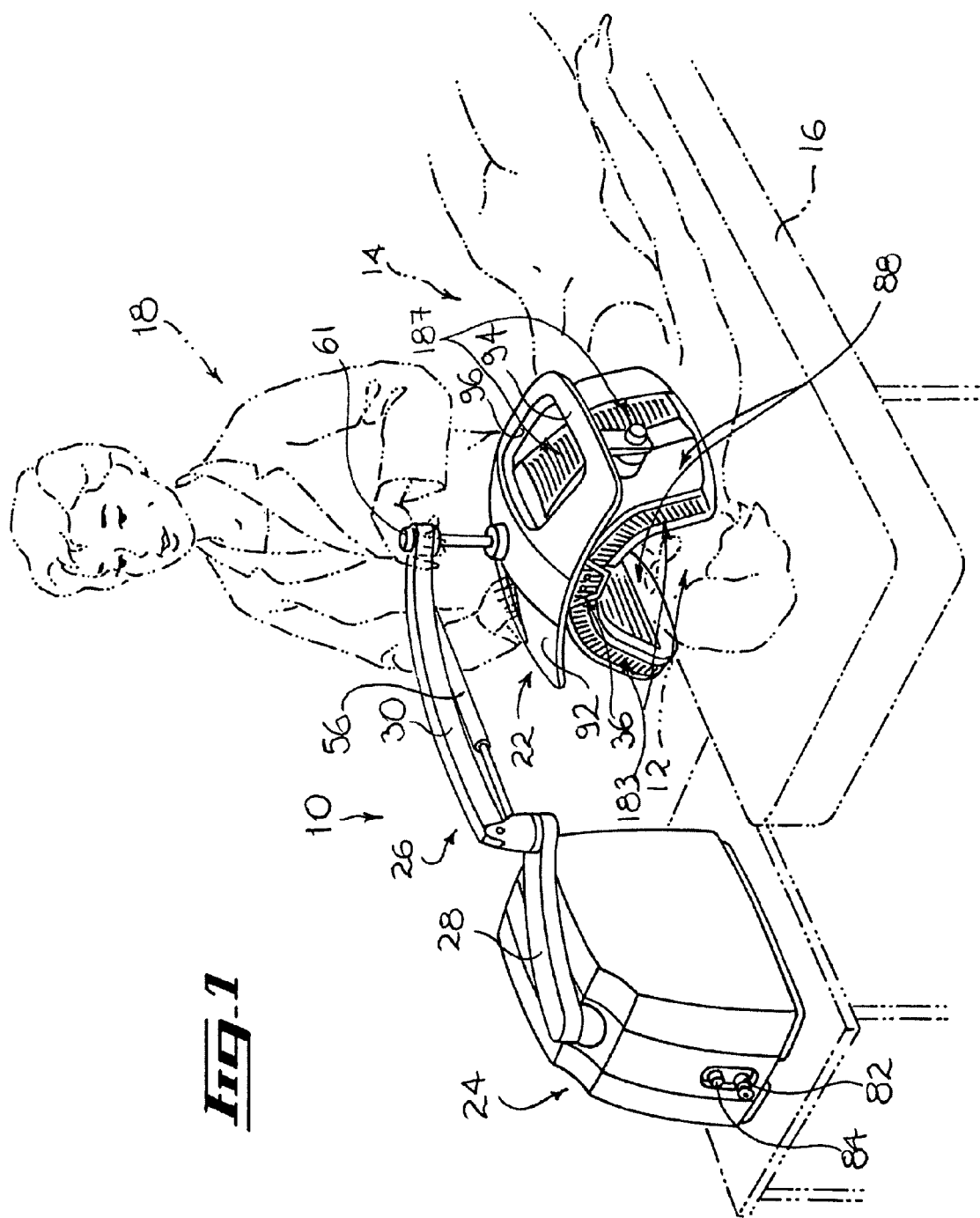

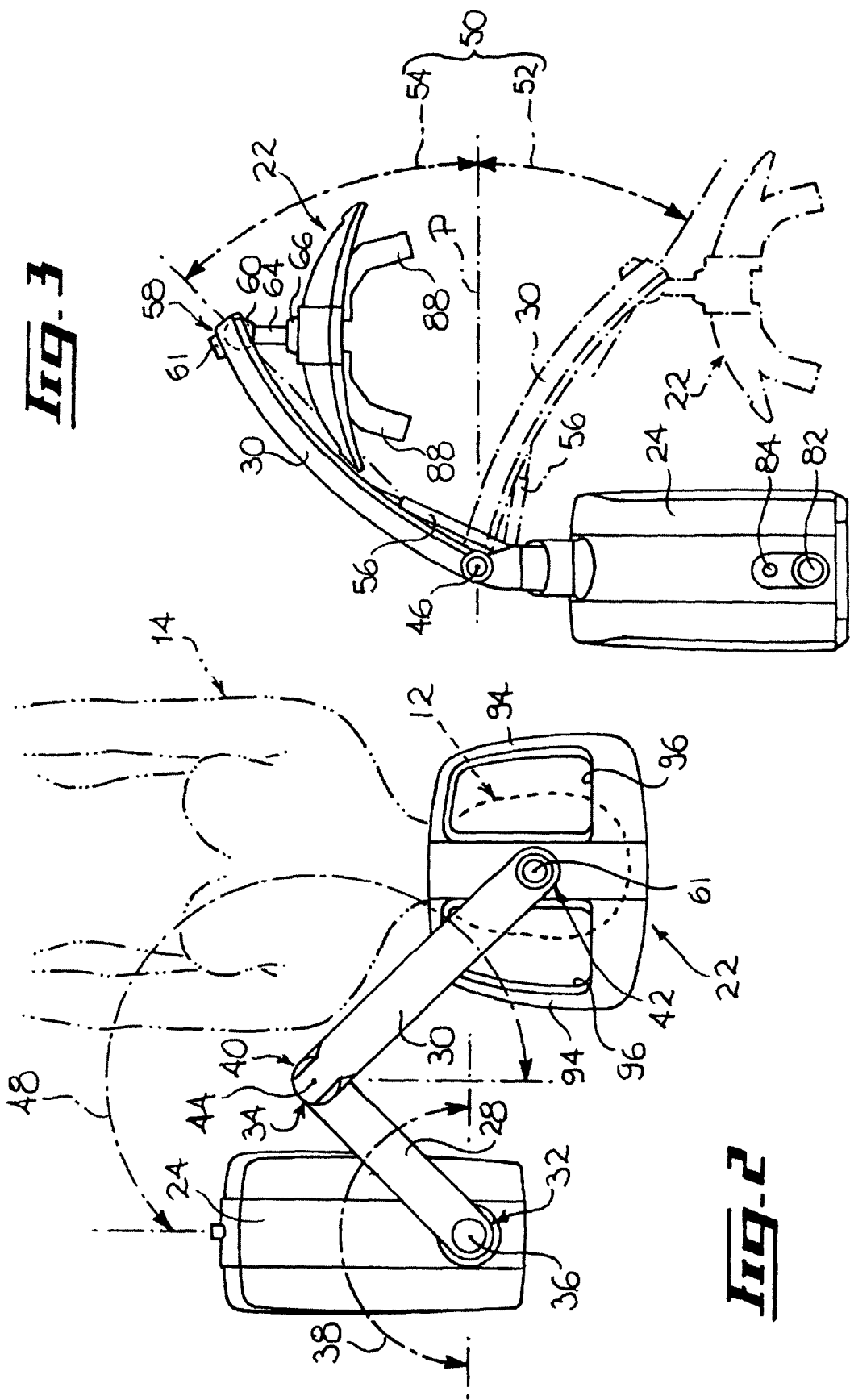

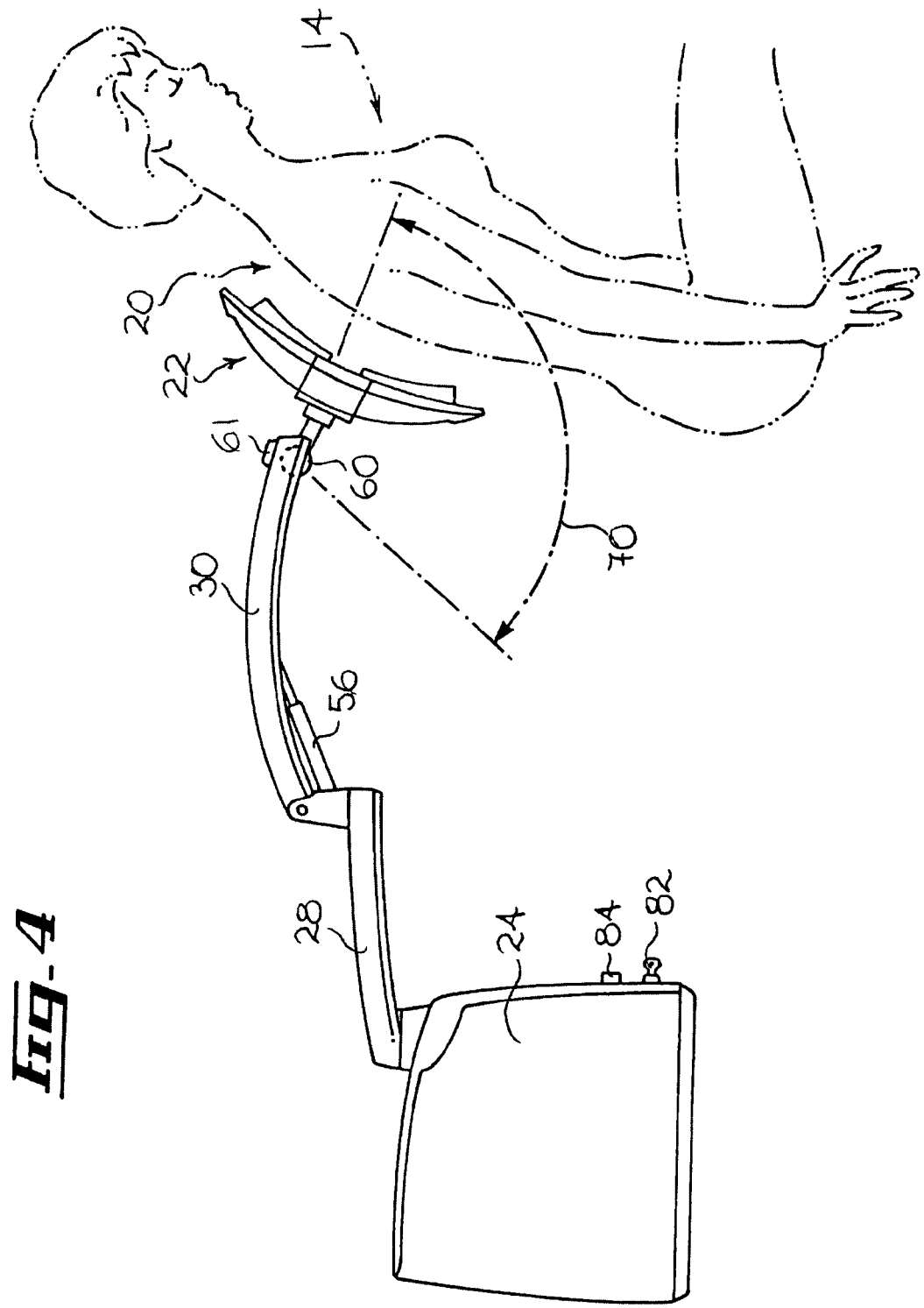

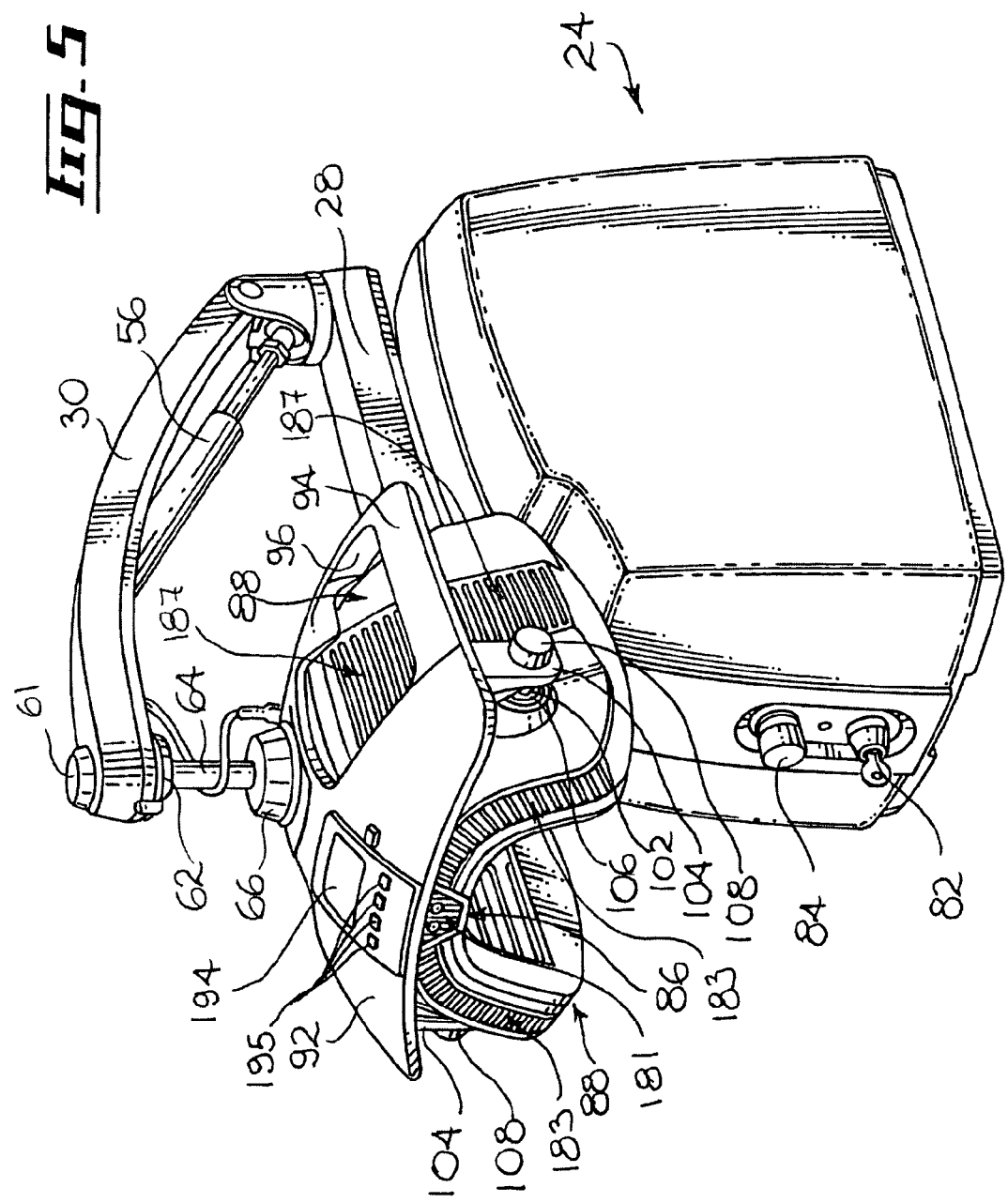

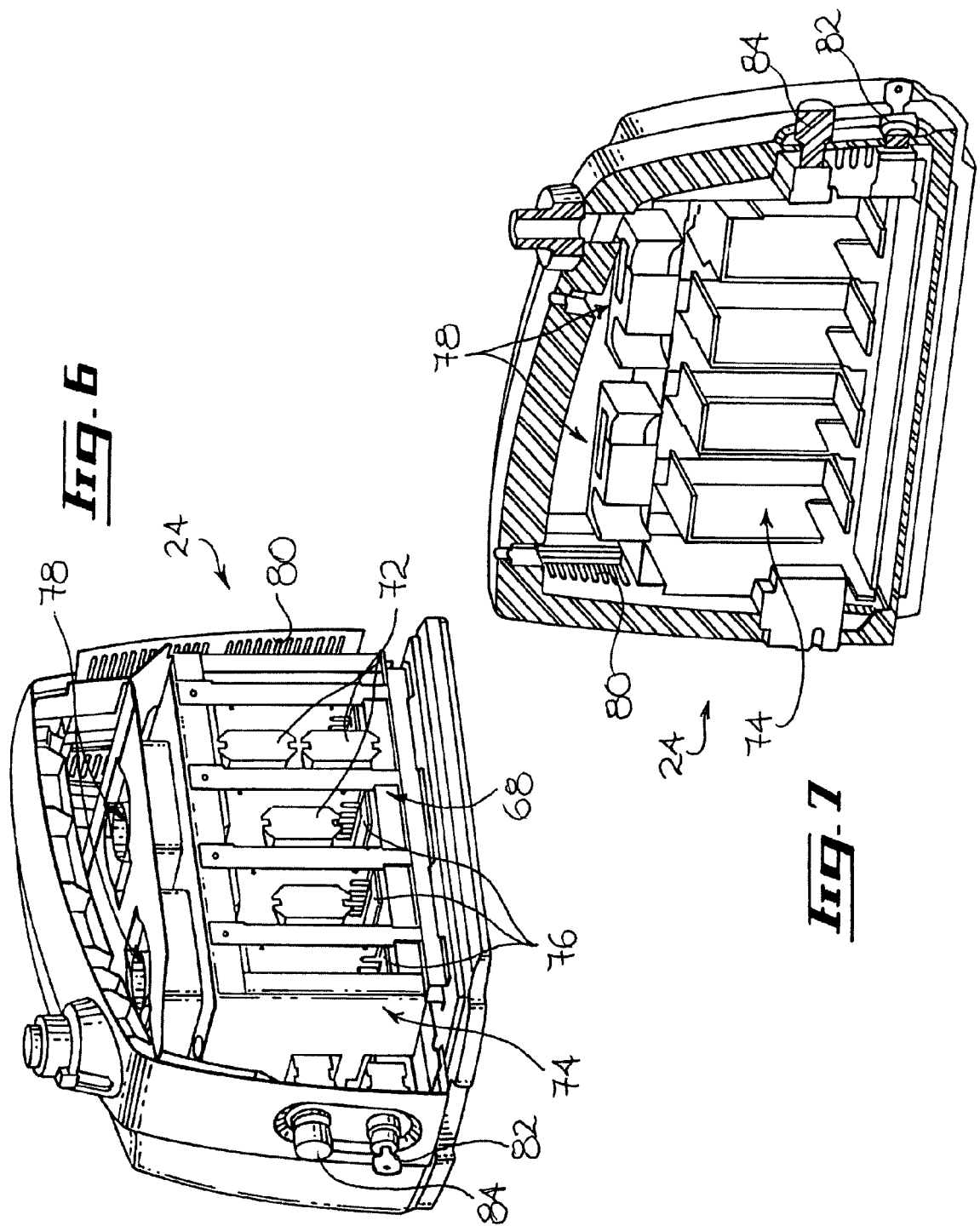

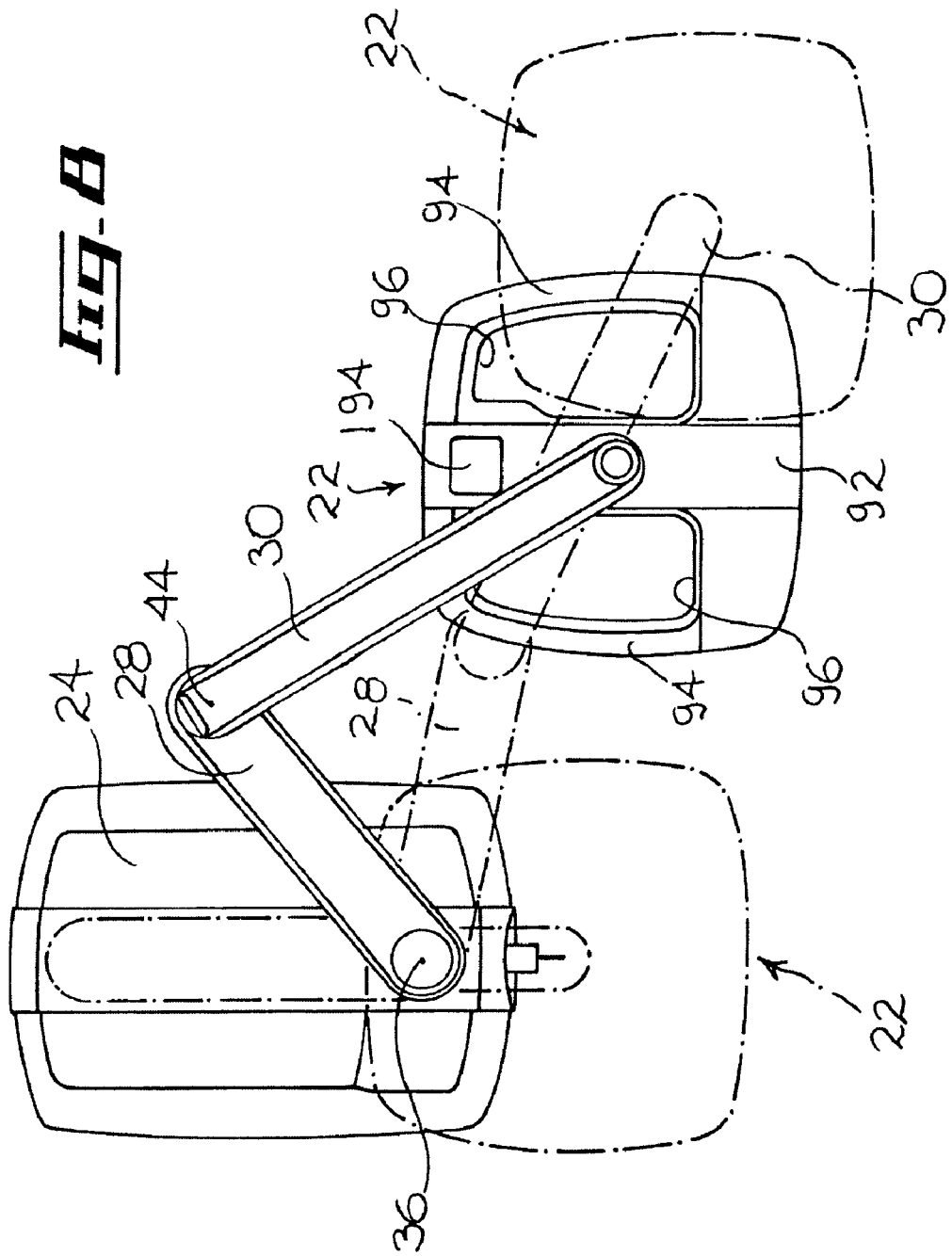

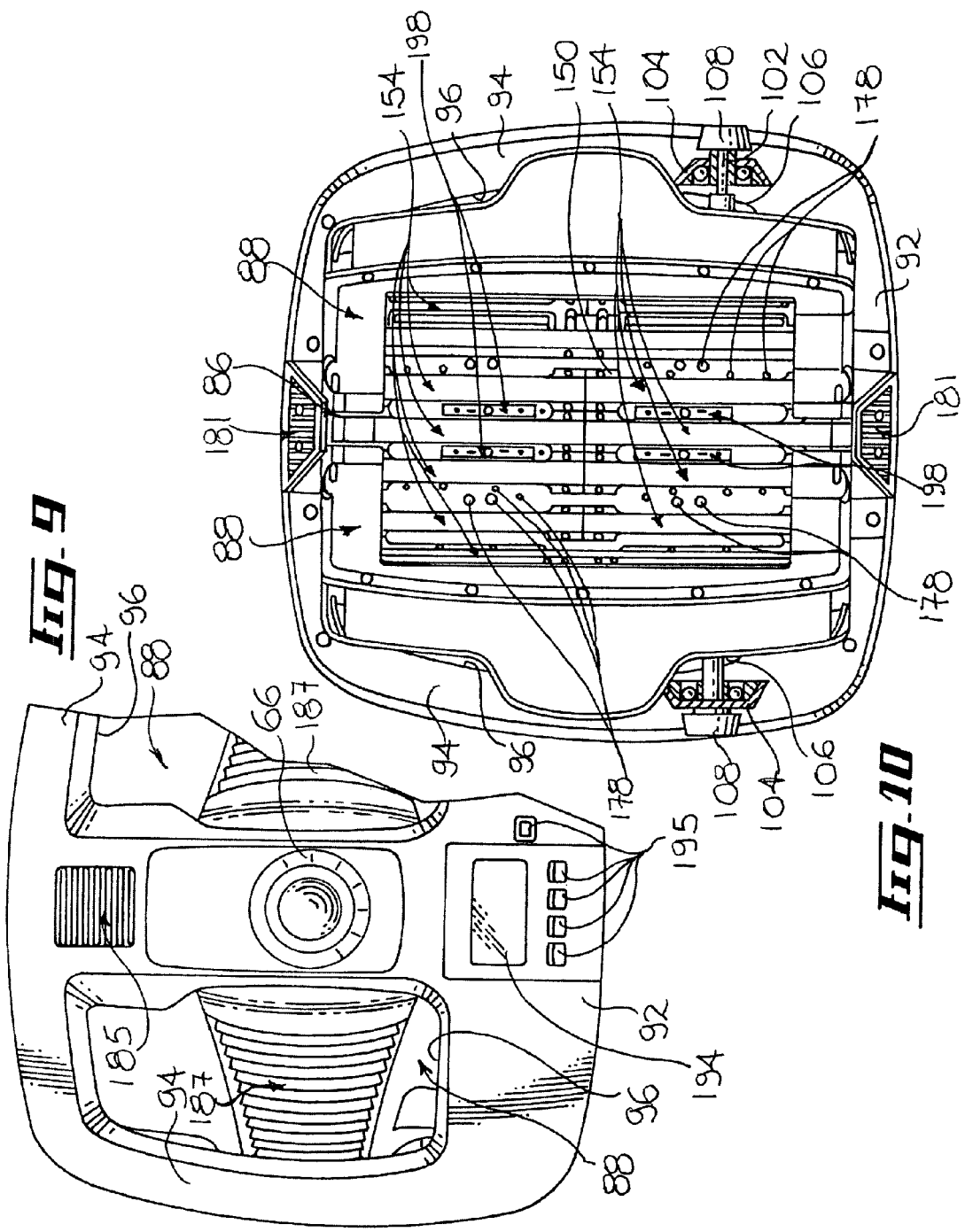

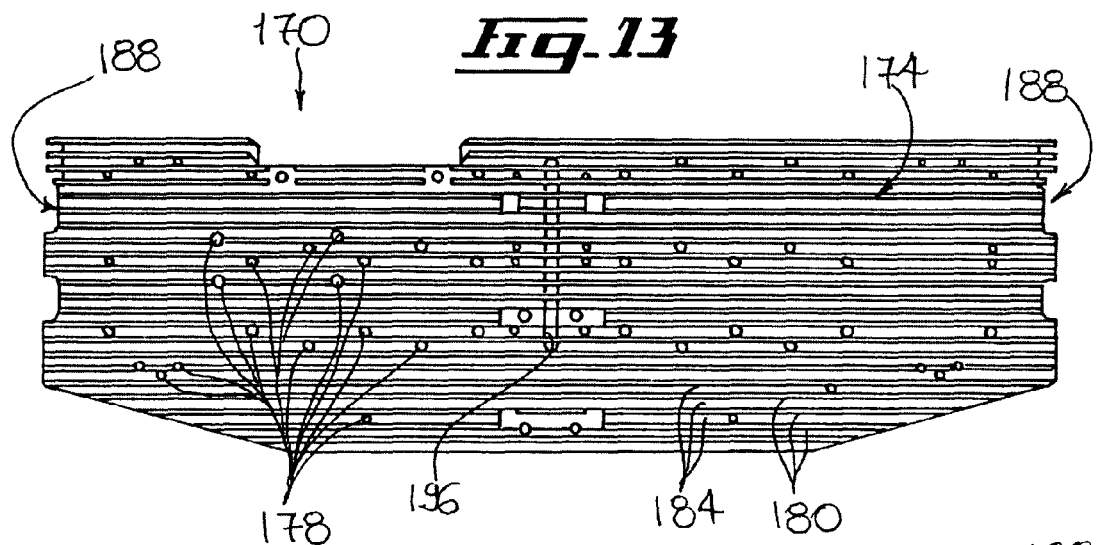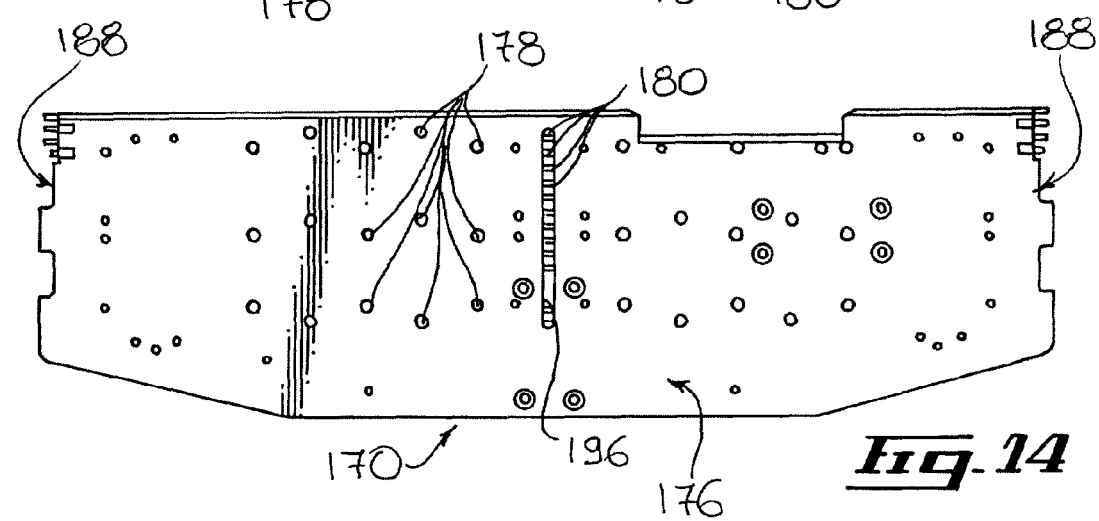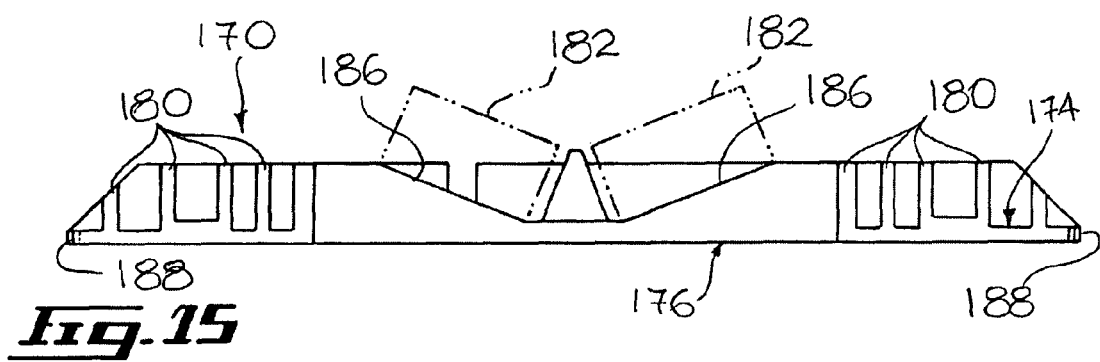

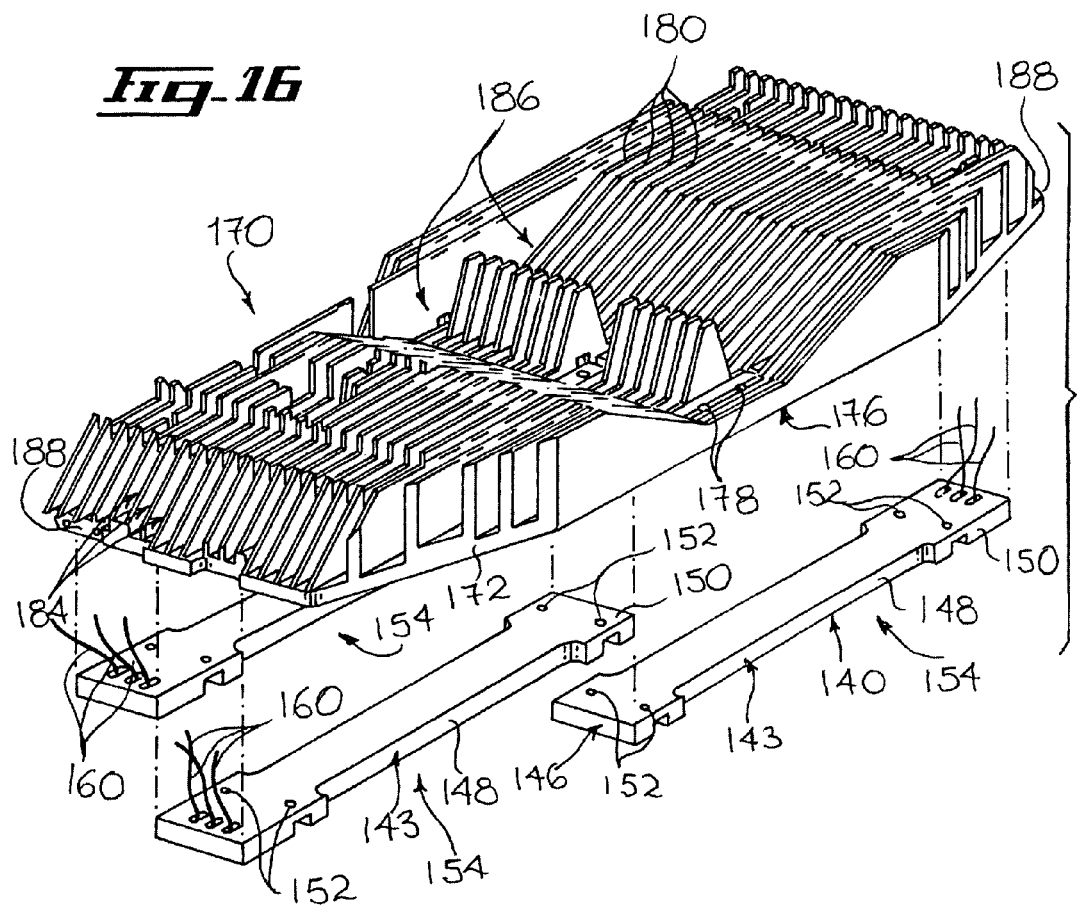
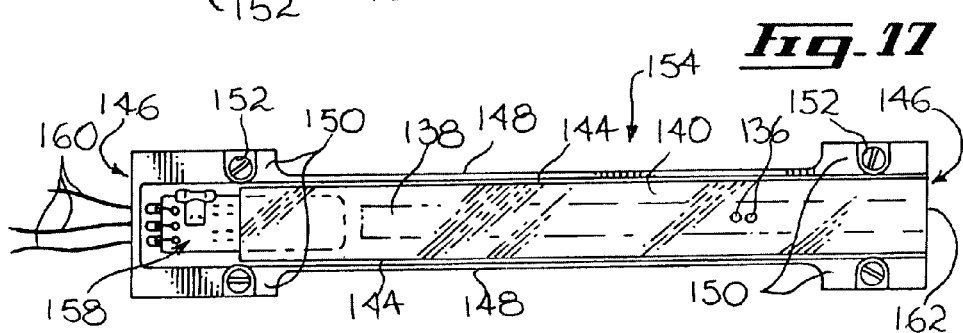

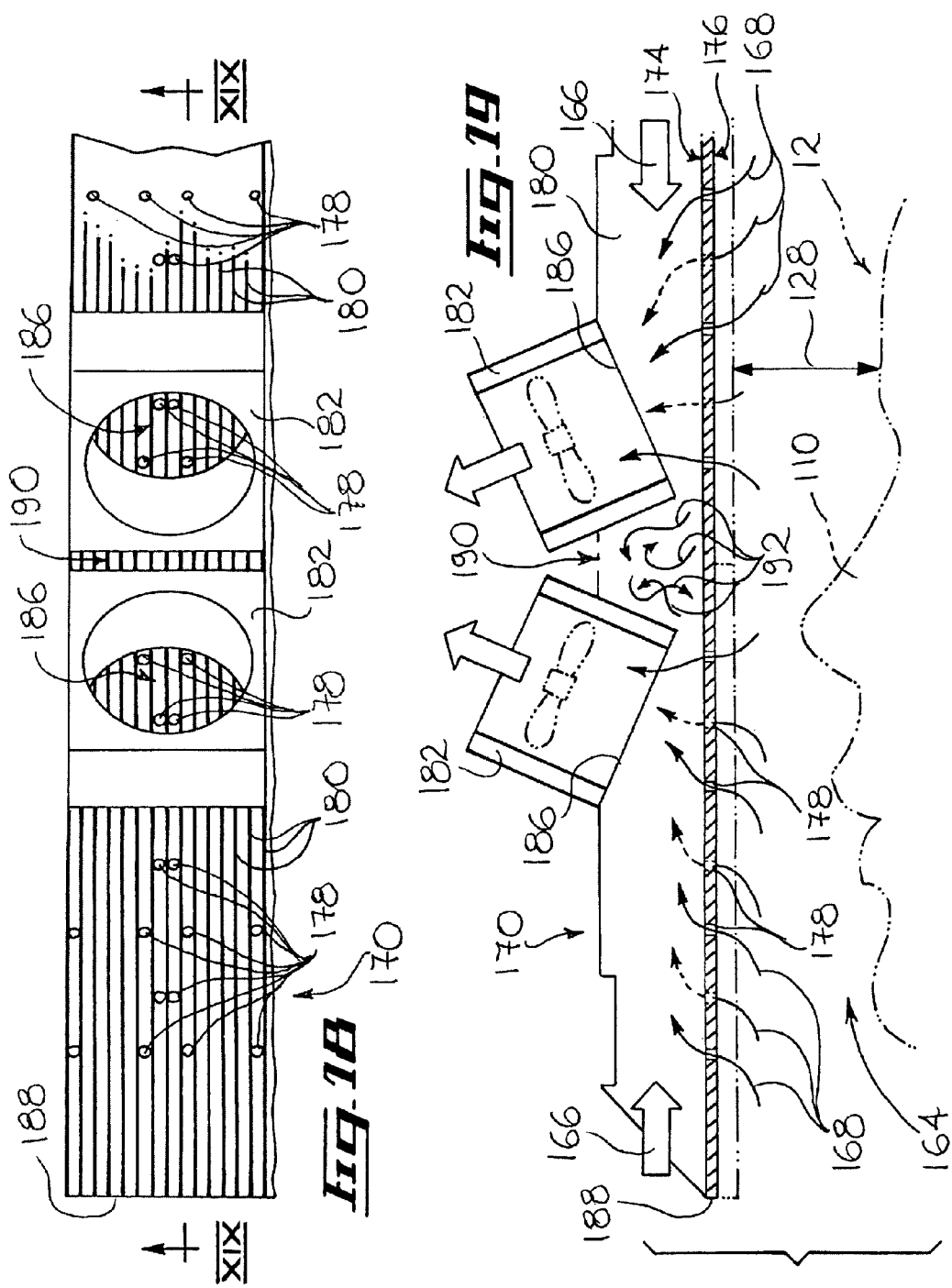

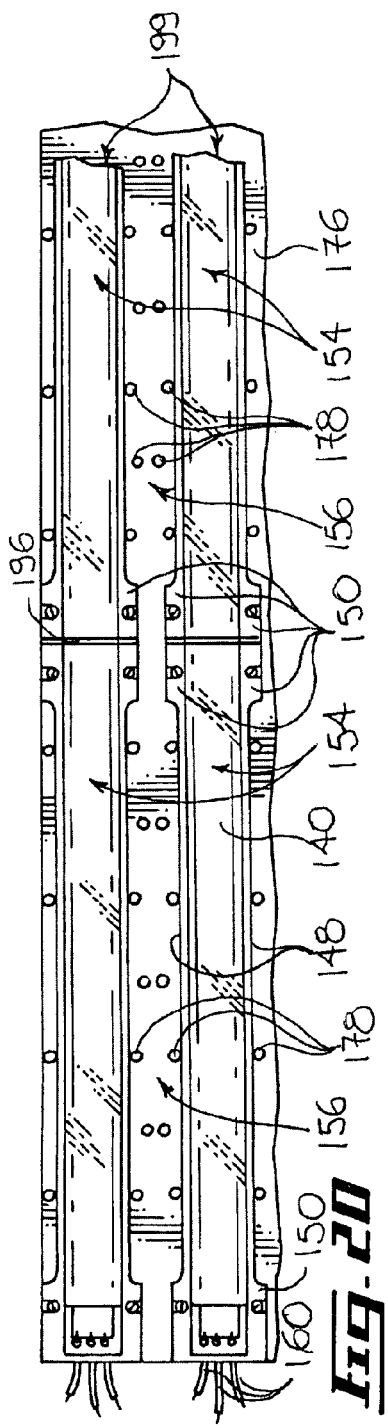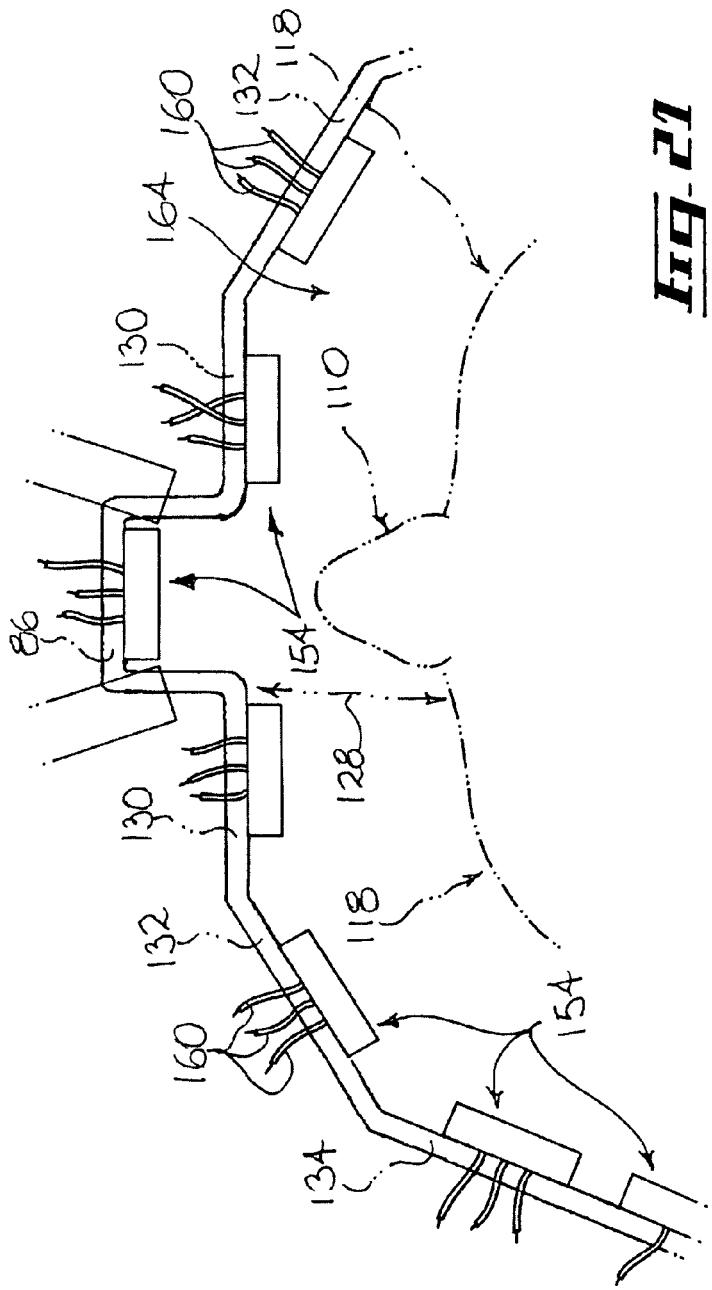

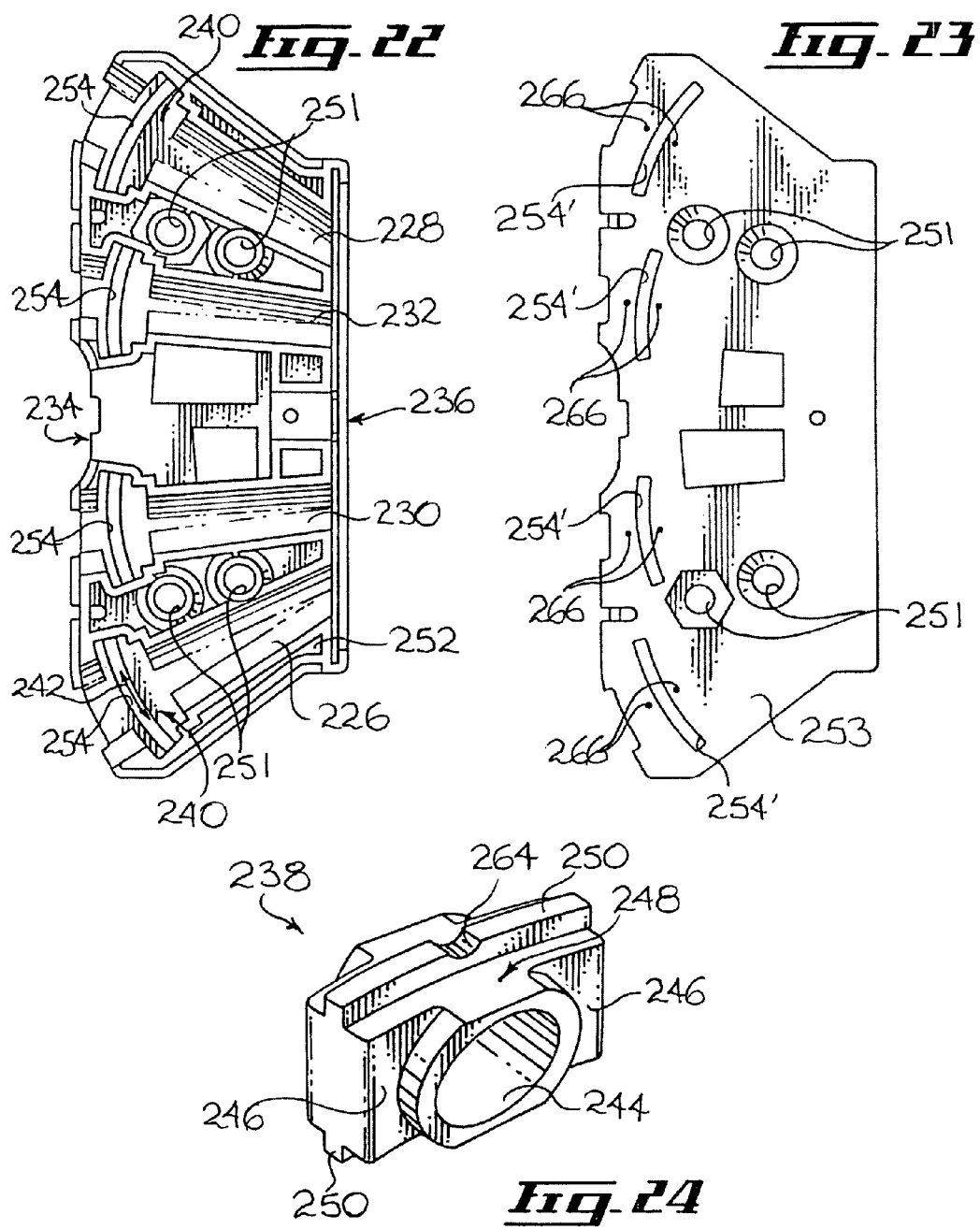

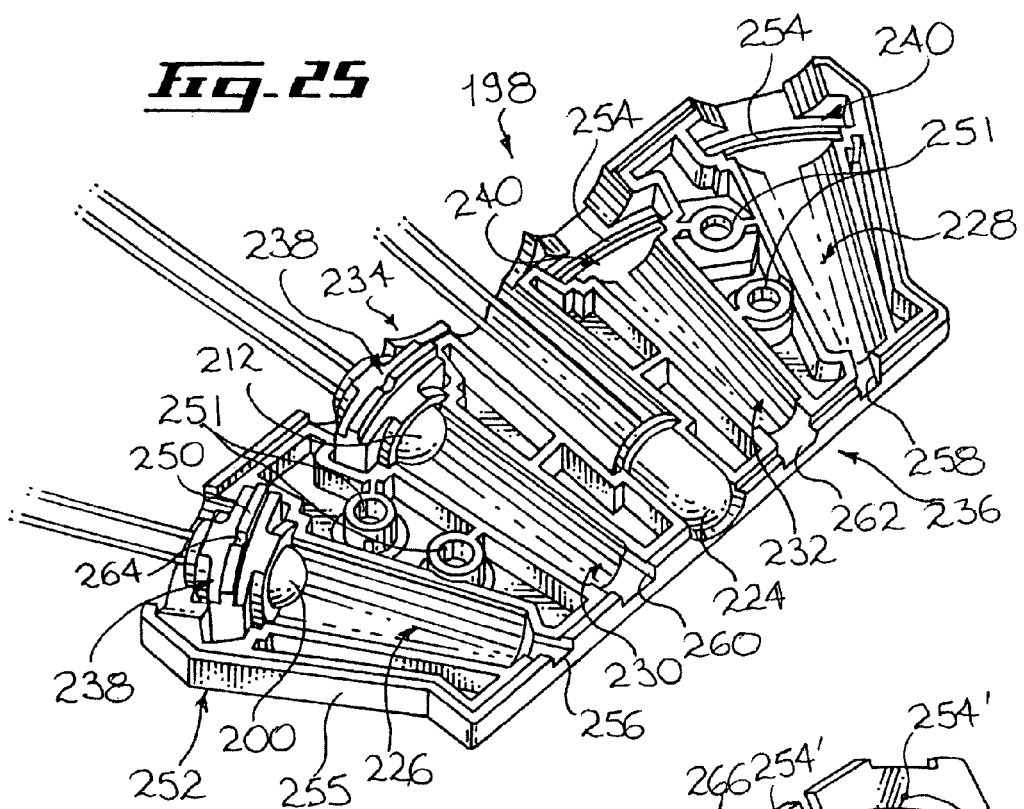
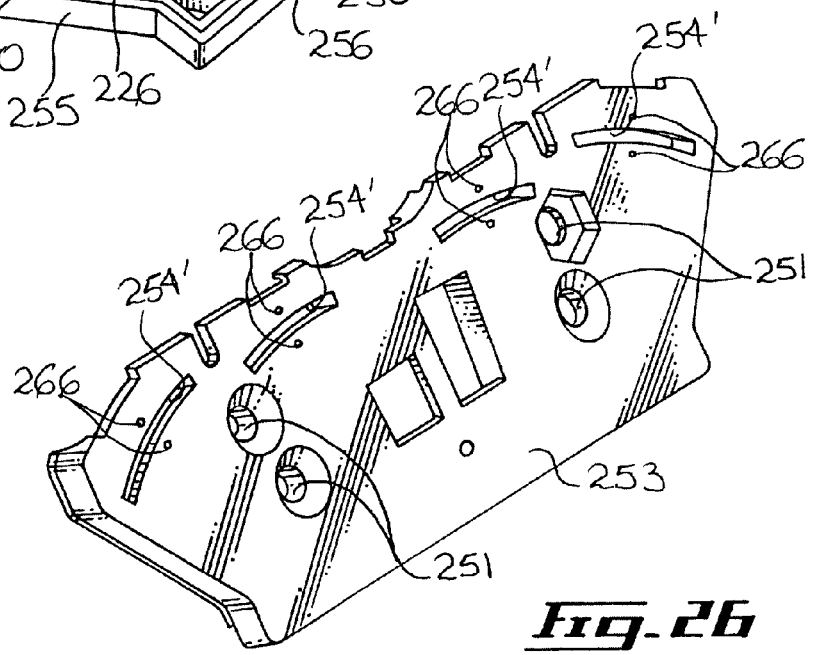

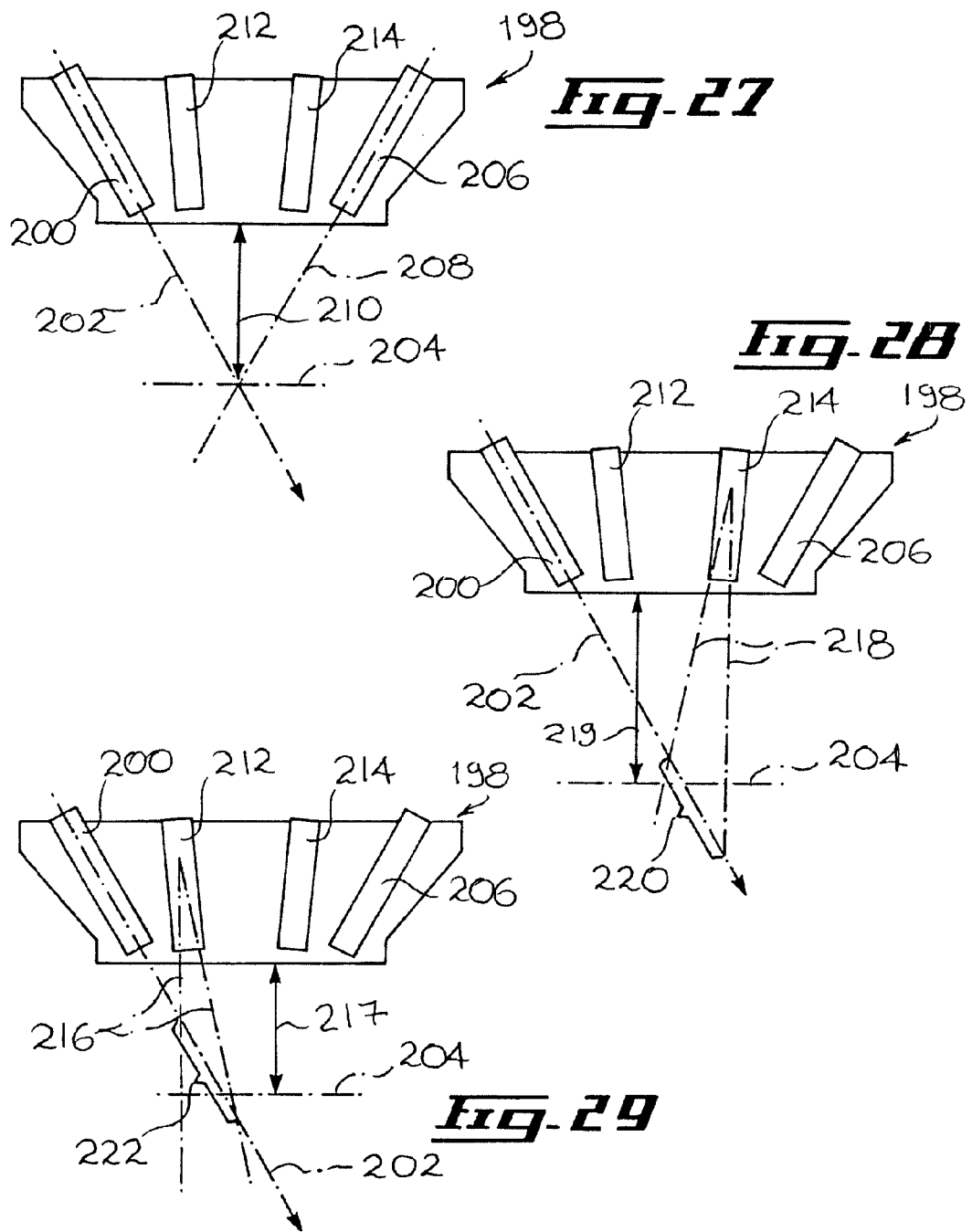

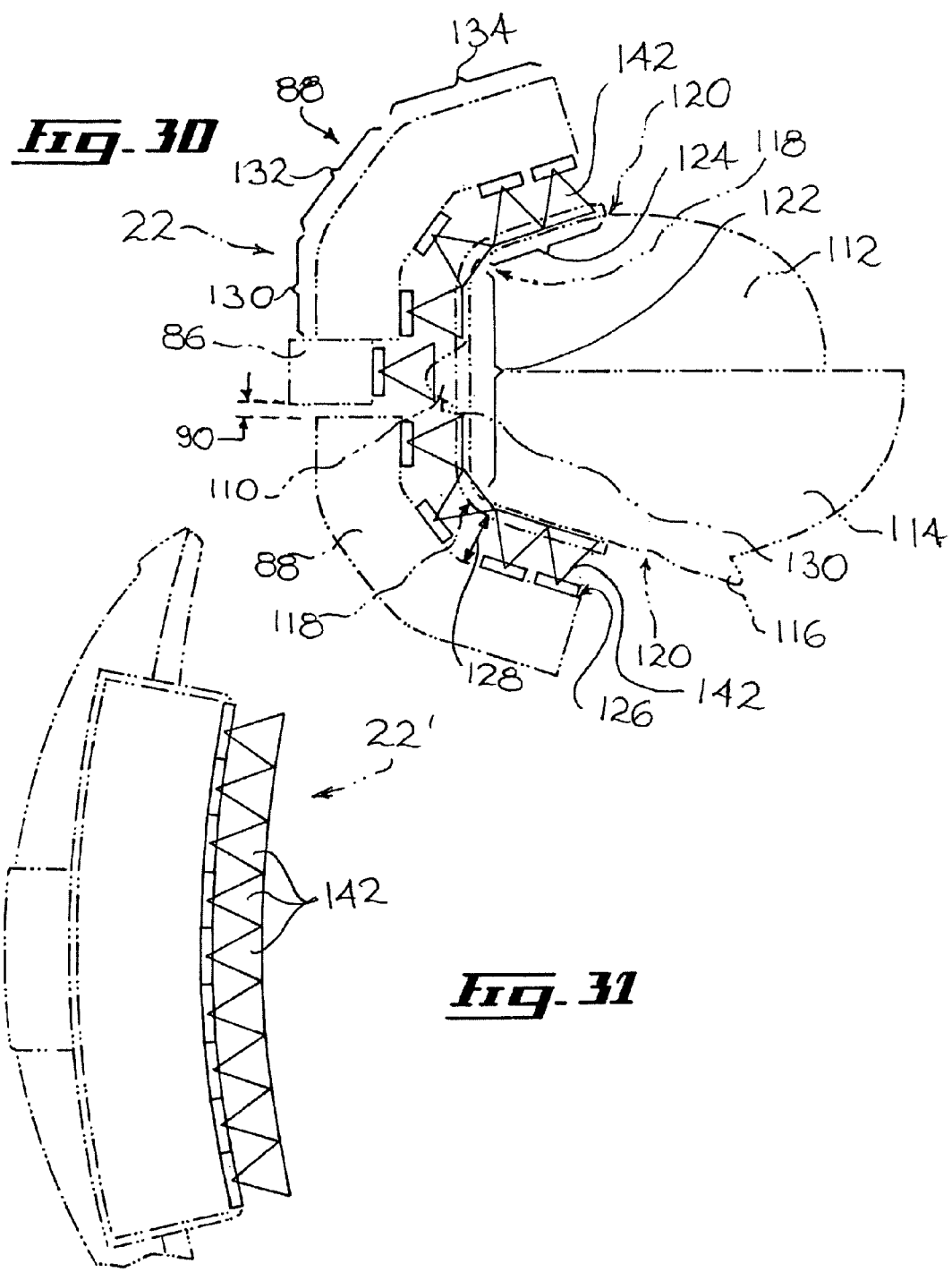

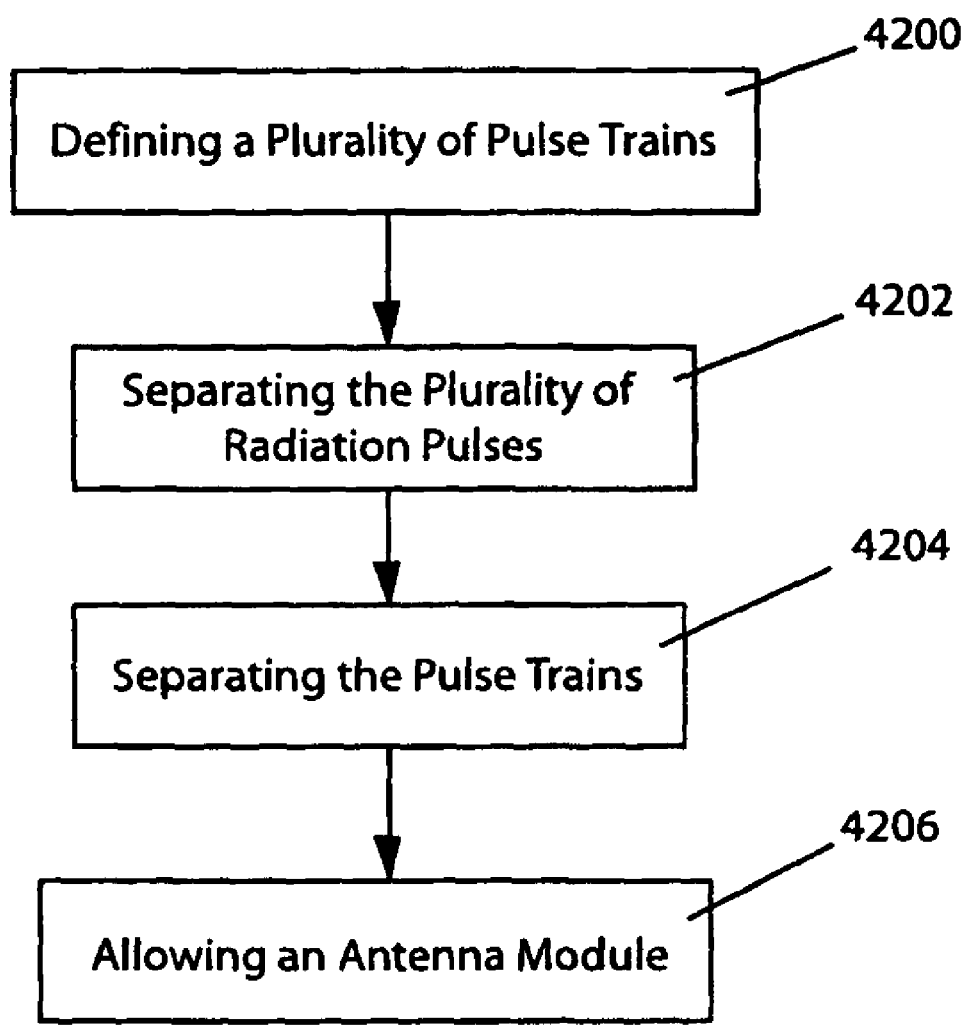

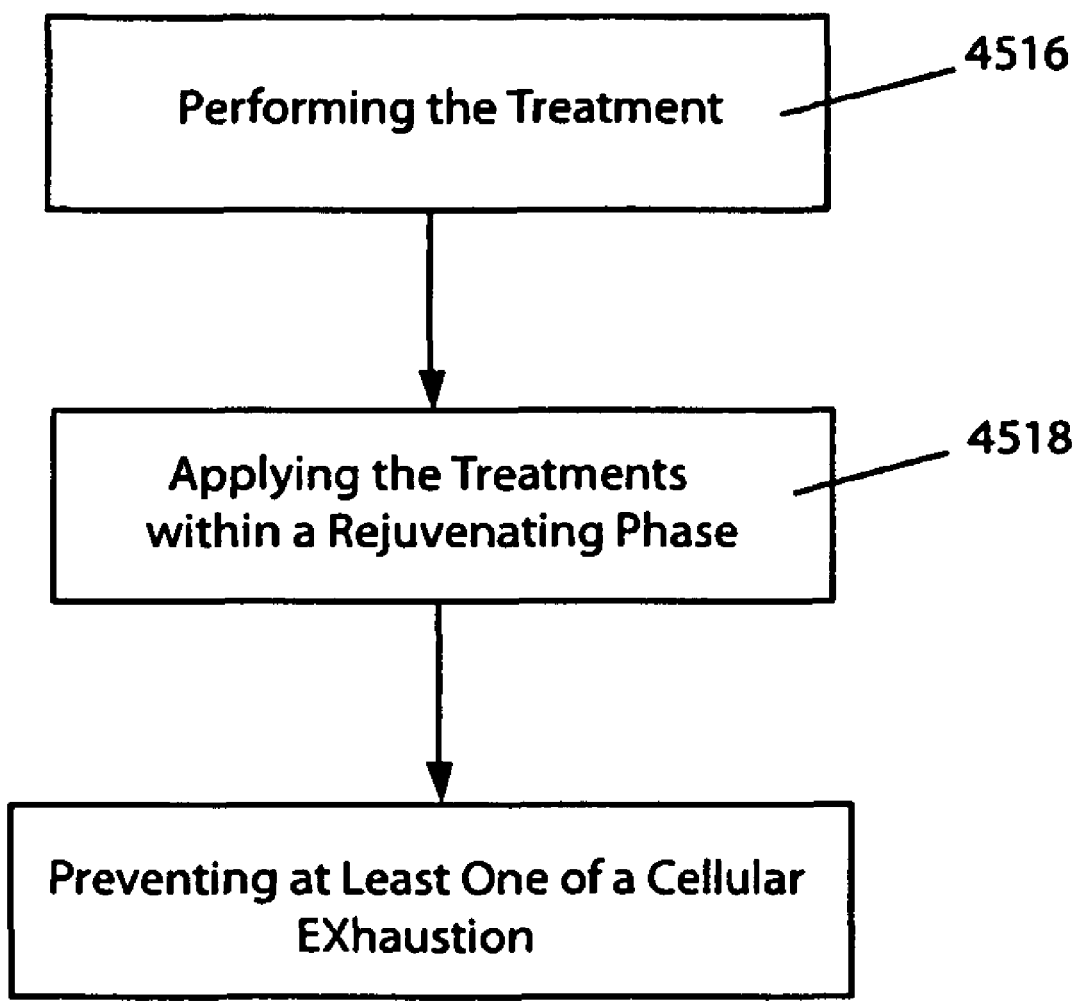

DEVICE FOR THE TREATMENT OF MAMMALIAN TISSUES

The present invention claims priority from Provisional Application Ser. No. 60/541,936 filed on Feb. 6, 2004. This application is also a Continuation of U.S. patent application Ser. No. 11/053,603 filed on Feb. 7, 2005. The contents of these two patent applications are hereby incorporated by reference in their entirety.

FIELD OF THE INVENTION

The present invention relates to the field of treatment of living tissue such as the dermatological treatment of skin, and is particularly concerned with a method and a device for the treatment of mammalian tissues.

BACKGROUND OF THE INVENTION

With aging demographics, dermatological treatments in general and in particular dermatological treatments for slowing the effects of aging are becoming increasingly popular.

It is known that aging of the skin shifts the balance between collagen production and breakdown, which leads to wrinkles, facial sag and rough skin texture. Stimulating skin cells to produce collagen can partly reverse this process. Stimulating collagen synthesis in aged skin is shown to reduce wrinkles and improve skin texture. The benefit of stimulating a person's own collagen production is that collagen is deposited in an orderly, structured manner and that there is no risk of allergy, immune reaction or injection-induced infection.

Some prior art methods for reducing the effects of aging on the skin were based on thermally injuring the skin with associated disadvantages. The first era of a different approach called low level laser radiation therapy and photobioactivation occurred in the 1960s and 1970s. Some lasers available were then tested for a biological effect. Largely anecdotal observations were made at the time.

The second era began in the 1980s. During this period, proper controls were used to discriminate the placebo effect from significant results. People became interested in the wavelengths of the radiation produced by the lasers, and began to investigate the photobiological basis of the therapeutic use of laser radiation.

A third era has recently started. More data on the photobiological basis of existing phototherapies are now available, and more is known about the photoactivation of enzymes and membranes. Some prior art methods and devices of photoinduction have been proposed. However, they have heretofore yielded relatively unsatisfactory results.

In view of the above, there is a need in the industry to provide a novel method and a novel device for the treatment of mammalian tissues.

The present description refers to a number of documents, the content of which is herein incorporated by reference in their entirety.

SUMMARY OF THE INVENTION

In a broad aspect, the invention provides a method for causing a predetermined physiological change in a mammalian tissue. The method includes irradiating the tissue with a radiation having a power density in the tissue substantially larger than an activation threshold power density, the tissue being irradiated under conditions suitable to cause the predetermined physiological change.

Advantageously, the claimed invention is relatively easy to perform and relatively safe. The claimed invention is furthermore relatively painless when performed in vivo and gives clinically significant results in relatively few treatments.

The invention is relatively well adapted to enhance physiological processes and causes relatively few side effects.

In another broad aspect, the invention provides a method for treating a mammalian skin tissue, the method including irradiating the tissue with radiation defining a pulse train including a plurality of radiation pulses, wherein:
 a. the radiation has a wavelength of from about 400 nanometers to about 1500 nanometers;
 b. the pulses each have a duration of from about 1 femtosecond to about 1 hour;
 c. the pulses are separated from each other by an inter-pulse interval, the inter-pulse interval being of from about 1 microsecond to about 10 seconds; and d. the power density of each pulse in the tissue is of from about 0.1 mW/cm2 to about 10 W/cm2.

In yet another broad aspect, the invention provides a method for altering the physiology of a mammalian tissue, the method including irradiating the tissue with radiation defining a plurality of pulse trains, each pulse train including a plurality of radiation pulses having a predetermined pulse duration, the pulses being separated from each other by an inter-pulse time interval, the pulse trains being separated from each other by an inter-train time interval, the inter-train interval being substantially larger than the inter-pulse interval.

In yet another broad aspect, the invention provides a method for altering the physiology of a mammalian tissue, the method including irradiating the tissue with a time-varying radiation according to a power density temporal profile suitable for both activating molecular cascades of events and activating cells contained within the tissue.

In yet another broad aspect, the invention provides a method for regenerating an extracellular matrix in mammalian tissue, the method including irradiating the tissue with radiation under conditions suitable to regenerate the extracellular matrix.

In yet another broad aspect, the invention provides a method for improving tissue integrity in mammalian tissue, the method including irradiating the tissue with radiation under conditions suitable to improve tissue integrity in the mammalian tissue.

In yet another broad aspect, the invention provides a method for reducing damages previously caused to a mammalian skin tissue, the method including irradiating the tissue with radiation presenting a power density temporal profile such that the radiation has a power density within the tissue that is above an activation threshold at least over a predetermined time interval, the predetermined time interval being such that the temperature of the tissue remains below an overheating temperature above which the radiation is ineffective to reduce the damages previously caused to the mammalian skin tissue.

Examples of such damages include damages caused by aging and pathologies, such as eczema, psoriasis and many others.

In accordance with the present invention, there is also provided a photoactivation device for modulating the physiology of a target biological activity by directing a photoactivating beam of light having a predetermined set of photoactivating light parameters on a target surface, the device comprising: a photoactivating light source for emitting the photoactivating beam of light; a positioning means operatively coupled to the photoactivating light source for allowing selective positioning of the photoactivating light source relative to the target surface; a position evaluating means for evaluating the position of the photoactivating light source relative to the target surface.

In accordance with the present invention, there is further provided a photoactivation device for modulating the physiology of a target cellular activity by directing photoactivating light having a predetermined set of photoactivating light parameters on a treatment area of a target human body; the device comprising:

a treatment head, the treatment head including a photoactivating light source for emitting photoactivating light, the treatment head also including a treatment area cooling means for cooling the treatment area.

Typically, the treatment head is spaced from the treatment area by a treatment head-to-treatment area spacing, the treatment area cooling means including a cooling air flowing means for creating a treatment area air flow flowing at least partially in the treatment head-to-treatment area spacing for cooling the treatment area. Conveniently, treatment head also includes a light source cooling means for cooling the photoactivating light source.

In accordance with the present invention, there is further provided a method of photoactivating mammalian tissue using a photoactivating device, the photoactivating device including a photoactivating light source adapted to generate a photoactivating beam of light having a predetermined set of light parameters, the mammalian tissue defining a target surface adapted to be irradiated by the photoactivating beam of light, the method comprising the steps of: positioning the photoactivating light source and the mammalian tissue relative to each other so that the photoactivating light source and the target surface are at a predetermined operational distance relative to each other; irradiating the target surface with the photoactivating beam of light while the photoactivating light source is spaced from the target surface by the operational distance; wherein the operational distance is such that the photoactivating beam of light photoactivates the biological tissue. Typically, the method includes using a distance probe for adjusting the distance between the photoactivating light source and the target surface towards the operational distance.

Conveniently, the method further comprises the step of: using an aiming beam of light emanating from an aiming device operatively coupled to the photoactivating light source for aiming the photoactivating light source towards the target surface prior to using the distance probe for adjusting the distance between the photoactivating light source and the target surface towards the operational distance.

In accordance with the present invention, there is yet still provided a method of photoactivating mammalian tissue using a photoactivating device, the photoactivating device including a photoactivating light source adapted to generate a photoactivating beam of light having a predetermined set of light parameters, the mammalian tissue defining a target surface adapted to be irradiated by the photoactivating beam of light, the method comprising the steps of: irradiating the target surface with the photoactivating beam of light emanating from the photoactivating light source; cooling the target surface so as to maintain the target surface at a temperature below a predetermined thermal threshold. Typically, the cooling of the target surface includes using a cooling flow of air for convectively cooling the target surface.

BRIEF DESCRIPTION OF THE DRAWINGS

Embodiments of the present invention will now be disclosed, by way of example, in reference to the following drawings in which:

FIG. 1, in an elevational view, illustrates a photoactivation device in accordance with an embodiment of the present invention being used for treating the face area of an intended patient;

FIG. 2, in a partial top view with sections taken out, illustrates a photoactivation device in accordance with an embodiment of the present invention being used for treating the face area of an intended patient;

FIG. 3, in a side view, illustrates a photoactivation device in accordance with an embodiment of the present invention, the photoactivation device being shown with its arm assembly in full lines in a raised position and in phantom lines in a lowered position;

FIG. 4, in a partial elevational view with sections taken out, illustrates a photoactivation device in accordance with an embodiment of the present invention being used for treating the back area of an intended patient;

FIG. 5, in a perspective view, illustrates a photoactivation device in accordance with an embodiment of the present invention;

FIG. 6, in a partial perspective view with sections taken out, illustrates the base portion of a photoactivation device in accordance with an embodiment of the present invention, the base portion of the photoactivation device being shown with part of its base casing removed therefrom;

FIG. 7, in a partial cross-sectional view with sections taken out, illustrates part of the base portion shown in FIG. 6 with some of its components removed therefrom;

FIG. 8, in a top view, illustrates a photoactivation device in accordance with an embodiment of the present invention, the photoactivation device being shown with its arm assembly moved between a retracted and an extended position;

FIG. 9, in a partial top view with section taken out, illustrates part of the treatment head of a photoactivation device in accordance with an embodiment of the present invention;

FIG. 10, in a bottom view, illustrates a treatment head part of a photoactivation device in accordance with an embodiment of the present invention;

FIG. 13, in a top view, illustrates a heat sink component part of a photoactivation device in accordance with embodiment of the present invention;

FIG. 14, in a bottom view, illustrates the heat sink component shown in FIG. 13;

FIG. 15, in a schematic elevational view, illustrates the heat sink component shown in FIGS. 13 and 14;

FIG. 16, in a perspective view, illustrates the heat sink component shown in FIGS. 13 through 15 having photoactivating light sources about to be attached thereto, the heat sink component and the photoactivating light sources being part of a photoactivation device in accordance with an embodiment of the present invention;

FIG. 17, in a bottom view, illustrates a lighting module part of a photoactivation device in accordance with an embodiment of the present invention;

FIG. 18, in a schematic top view with sections taken out, illustrates part of a the heat sink shown in FIGS. 13 through 15 with air fan casings mounted thereon;

FIG. 19, in a longitudinal cross-sectional view taken along arrows XIX-XIX of FIG. 18, illustrates the heat sink and air fan casings shown in FIG. 18;

FIG. 20, in a partial bottom view with sections taken out, illustrates a set of lighting modules mounted on a heat sink, the lighting modules and the heat sink being part of a photoactivation device in accordance with an embodiment of the present invention;

FIG. 21, in a schematic and partial transversal cross-sectional view with sections taken out, illustrates the face of an intended patient positioned underneath a treatment head part of a photoactivation device in accordance with an embodiment of the present invention;

FIG. 22, in a top cross-sectional view, illustrates part of the casing of a distance probe, the distance probe being part of a photoactivation device in accordance with an embodiment of the present invention;

FIG. 23, in a bottom view, illustrates a complementary part to the casing shown in FIG. 22;

FIG. 24, in a perspective view, illustrates an attachment component part of a distance probe, the distance probe being part of a photoactivation device in accordance with an embodiment of the present invention;

FIG. 25, in a partial perspective view with sections taken out, illustrates some of the internal components of a distance probe, the distance probe being part of a photoactivation device in accordance with an embodiment of the present invention;

FIG. 26, in a partial perspective view with sections taken out, illustrates a complementary section of the distance probe partly shown in FIG. 25;

FIG. 27, in a schematic elevational view, illustrates a distance probe positioned at a target distance relative to a target tissue;

FIG. 28, in a schematic elevational view, illustrates a distance probe positioned at a greater distance than a target distance relative to a target tissue;

FIG. 29, in a schematic elevational view, illustrates a distance probe positioned closer to a target tissue than a target distance;

FIG. 30, in a schematic cross-sectional view, illustrates a treatment head part of a photoactivation device in accordance with an embodiment of the present invention, the treatment head being shown treating two juxtaposed sagittal half-head sections respectively of a woman in the 5th percentile and of a man in the 95th percentile in terms of size, the women and men sagittal half-head sections being shown transversally sectioned about a mid-plane taken adjacent the level of the nose;

FIG. 31, in a partial schematic elevational view, illustrates an alternative treatment head such as that shown in FIG. 4;

FIG. 42 is a flow chart illustrating a further method of the invention;

FIG. 45b is a flow chart illustrating a further method embodiment;

DETAILED DESCRIPTION

Figure 11:
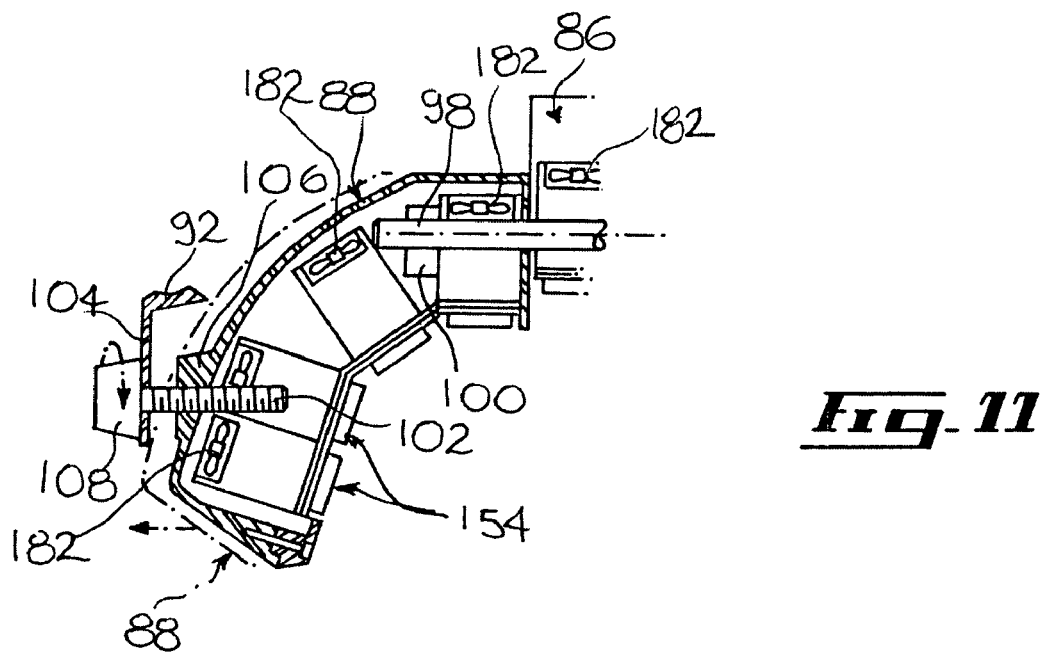
FIG. 11, in a partial transversal cross-sectional view with sections taken out, illustrates some of the components of the treatment head of a photoactivation device in accordance with an embodiment of the present invention.

Referring to FIG. 1, there is shown in a schematic perspective view, a photoactivation device in accordance with an embodiment of the present invention, generally designated by the reference numeral 10. The photoactivation device 10 is adapted to be used mainly for modulating the physiology of a target biological activity by directing photoactivating light having a predetermined set of photoactivating light parameters on a treatment area of a target human body. Although throughout the text the examples of photoactivation result mainly in photoinduction of the physiology of a target biological activity, it should be understood that photoactivation could result in a photoinhibition of the target biological activity without departing from the scope of the present invention In FIG. 1, the photoactivation device 10 is shown being used for treating the face area 12 of an intended patient 14 lying on a treatment bed 16. The photoactivation device 10 is shown being operated by a nearby standing operator 18. It should, however, be understood that the photoactivation device 10 could be used in other contexts such as for treating other treatment areas without departing from the scope of the present invention. For example, FIG. 4 illustrates a photoactivation device 10 being used for treating the upper back region 20 of a sitting patient 14.

Photoactivation device 10 includes a treatment head 22. The treatment head 22, in turn, includes a photoactivating light source for emitting photoactivating light. The photoactivation device 10 also includes a device base 24 for supporting the device 10 on a supporting surface such as a table top, a floor or the like. The device 10 further includes a base-to-head arm assembly 26 for mechanically coupling the treatment head 22 to the device base 24 and allowing selective movement of the treatment head 22 relative to the device base 24.

As shown more specifically in FIGS. 1 through 5 and 8, the base-to-head arm assembly 26 typically includes an assembly first arm 28 and an assembly second arm 30. The assembly first arm 28 defines a first arm first end 32 and a longitudinally opposed first arm second end 34. As shown more specifically in FIG. 2, the assembly first arm 28 is pivotally coupled substantially adjacent the first arm first end 32 to the device base 24 for pivotal movement relative thereto about a substantially vertical first arm rotation axis 36 through a predetermined first arm rotation range 38.

FIG. 2 illustrates the first arm rotation range 38 as having a value of approximately 180 degrees. It should, however, be understood that the first arm rotation range 38 could have other values without departing from the scope of the present invention.

The assembly second arm 30 defines a second arm first end 40 and a longitudinally opposed second arm second end 42. The assembly second arm 30 is pivotally coupled substantially adjacent the second arm first end 40 to the assembly first arm 28 for pivotal movement relative thereto about both a substantially vertical second arm vertical rotation axis 44 and a substantially horizontal second arm horizontal rotation axis 46. Rotation of the assembly second arm 30 about the second arm vertical rotation axis 44 is allowed through a predetermined second arm horizontal rotation range 48 shown in FIG. 2. Rotation of the assembly second arm 30 about the horizontal rotation axis 46 is allowed through a predetermined vertical rotation range 50 illustrated in FIG. 3.

The second arm horizontal rotational range 48 is shown in FIG. 2 as having a value of approximately 225 degrees. The second arm vertical rotation range 50 is illustrated in FIG. 3 as having an overall value of approximately 75 degrees with a first segment 52 thereof spanning generally downwardly approximately 30 degrees from an horizontal reference plane P and a second segment 54 thereof spanning generally upwardly approximately 45 degrees from the horizontal reference plane P.

It should, however, be understood that the second arm horizontal and vertical rotation ranges 48, 50 and the first and second segments 52, 54 of the second arm vertical rotation range 50 could have other values without departing from the scope of the present invention. Also, although the assembly first and second arms 28, 30 typically have a length respectively of approximately 32 cm and 82 cm, the assembly first and second arms 28, 30 could have other dimensional values without departing from the scope of the present invention.

The base-to-head arm assembly 26 typically also includes a weight compensating assembly or means mechanically coupled to the assembly second arm 30 for at least partially compensating for the weight of the treatment head 22 and preventing the assembly second arm 30 from pivoting about the second arm horizontal rotation axis 46 under the weight of the treatment head 22. In the embodiments shown throughout the Figures, the weight compensating means includes a pneumatic cylinder 56. It should, however, be understood that the weight compensating means may take any other suitable form such as that of a resiliently deformable member, strategically positioned compensating weights or the like without departing from the scope of the present invention.

The base-to-head arm assembly 26 typically further includes an arm-to-head universal-type mechanical coupling or swivel 58 extending between the assembly second arm 30 substantially adjacent the second arm second end 42 and the treatment head 22 for mechanically coupling the latter and allowing the treatment head 22 to pivot and rotate relative to the assembly second arm 30. The base-to-head arm assembly 26 typically still further includes an arm-to-head releasable locking assembly or means for releasably locking the treatment head 22 in a head operational position relative to the assembly second arm 30. The arm-to-head swivel and the arm-to-head locking means may take any suitable form without departing from the scope of the present invention. In one embodiment of the invention, the arm-to-head mechanical coupling 58 includes a swivel ball 60 mounted within a corresponding swivel socket 62 so as to form a ball and socket-type joint. A swivel spacing segment 64 extends from the swivel ball 60 for attachment to the treatment head 22.

The arm-to-head mechanical coupling 58 is typically of the universal-type allowing the treatment head 22 to swivel through a three-dimensional swivel range 70. Although the swivel range 70 is shown in 4 has having a value of approximately 115 degrees in one plane, it should be understood that the swivel range 70 also acts across multiple planes wherein the swivel range for each plane can be the same or different values. Thus, treatment head 22 can be swivelled into and out of the plane illustrated in FIG. 4. Additionally, the swivel ranges can have other values without departing from the scope of the present invention. The arm-to-head mechanical coupling 58 typically also allows the treatment head 22 to rotate relative to a head rotational axis extending substantially co-axially with the longitudinal axis of the swivel spacing component 64. Thus, mechanical coupling 58 can allow treatment head 22 to spin on one axis, permitting treatment head 22 to be orientated to any angle in relation to the base 24, as well as second arm 30.

The arm-to-head releasable locking means typically include means for increasing the friction between the swivel socket 62 and the swivel ball 60 through the use of a knob 61 or the like. The arm-to-head releasable locking means may take any other suitable form including the use of temperature-dependent memory alloys adapted to change configuration for selectively frictionally engaging the swivel ball 60.

The device 10 also typically includes an arm-to-head releasable electrical coupling 66 extending between base-tohead arm assembly 26 and the treatment head 22 for releasably electrically coupling the latter. Preferably, the arm-to-head releasable electrical coupling 66 allows for quick, easy and ergonomic coupling of treatment head 22 to a portion of the base-to-head arm assembly 26 such as to the swivel spacing component 64. This, in turn, allows for customisation of the treatment head 22 depending on the area being treated, the desired type of photoactivation effect or other operational parameters.

For example, FIGS. 1, 2, 3, 5, 21 and 30 illustrate a substantially arc-shaped treatment head 22 adapted for treating the face region 12 of an intended patient 14 whereas FIGS. 4 and 31 illustrate a generally concave yet relatively more flattened treatment head 22 adapted for treating the back region 20 of an intended patient 14. Further, the arc shaped treatment head 22 can be used to partially surround and treat appendages such as the arms and legs of the intended patient 14 or other body parts such as the buttocks or individual breasts of the intended patient 14. Further, the "flattened" treatment head 22' can be used for treating the chest and sides of patient 14 and can be sized to treat a larger surface area. It should be understood that other types of treatment heads 22 having other configurations could also be used without departing from the scope of the present invention.

As illustrated more specifically in FIGS. 6 and 7, the device base 24 typically protectively houses at least part of a device power supply generally referred to by the reference numeral 68. The power supply 68 includes at least one and typically four power supply units 72 mounted within a conventional Faraday-type cage 74. The Faraday-type cage 74 also houses at least one and typically four relay components 76.

A device base venting assembly or means is typically provided for venting the components housed within the device base 24. The device base venting assembly or means typically includes at least one and preferably two base venting fans 78 mounted on the Faraday cage 74. The device base fans 78 are adapted to convectively cool the components housed within the device base 24 by drawing air through a base venting grid 80.

An on-off switch 82 and an emergency stop switch 84 typically extend from the device base 24 for allowing an intended user respectively to turn the device 10 on and off and to quickly turn the device 10 off in case of an emergency.

Referring now more specifically to FIGS. 9 through 12, 21 and 30, there is shown, in greater details, some of the features of a treatment head 22 intended for use in treating a human face area. Typically, such treatment head 22 includes at least two and preferably three head sections. Each of the head sections is typically provided with a photoactivating light source 154 for emitting photoactivating light. Typically, at least two of the head sections are movable relative to each other. As will be hereinafter disclosed in greater details, in situations wherein at least two of the head sections are movable relative to each other, each of the movable head sections also includes a section positioning means operatively coupled to a corresponding section photoactivating light source 154 for allowing selective positioning of the corresponding section photoactivating light source 154 relative to a corresponding target surface section.

In other words, the target surface on which photoactivating light is directed is typically dividable into target surface sections and the treatment head is dividable into corresponding head sections each having a corresponding section photoactivating light source 154. Furthermore, the individual head sections and, hence, their corresponding individual section photoactivating light source 154 are allowed to move relative to each other in order to provide optimal treatment to the individual target surface sections.

As illustrated schematically in FIG. 30, the treatment head 22 intended to be used for treating a human face area 12 typically includes a central head section 86 and a pair of lateral head sections 88. The lateral head sections 88 are positioned on each side of the central section 86. Furthermore, at least one of the lateral head sections 88 and preferably both lateral head sections 88 are laterally displaceable relative to the central head section 86. To illustrate the relative movement between the lateral head sections 88 and the central head section 86, the lateral head section 88 appearing in the top part of FIG. 30 is shown as being in a proximal relationship relative to the central head section 86 while the lateral head sections 88 appearing in the lower part of FIG. 26 is shown as being spaced relative to the central head section 86 by a central-to-lateral head section spacing 90. This allows the lateral head sections 88 to maintain the same distance from the face area 12 regardless of the size and/or shape of the patient's 14 face.

As illustrated more specifically in FIGS. 1, 2 and 8 through 12, the treatment head 22 typically includes a head base 92. The head base 92 typically defines a graspable head base handle section. In the embodiments shown throughout the Figures, the graspable head base handle section includes a pair of handle segments 94 delimited, at least in part, by corresponding adjacent handle section apertures 96 positioned on each side of the head base 92. The handle segments 94 are conveniently configured and sized for being graspable by the hand of an intended operator 18 to allow manual positioning of the treatment head 22.

Typically, the central head section 86 is fixedly attached to the head base 92. The central and lateral head sections 86, 88 are typically provided with cooperating lateral guiding assemblies or means operatively coupled therebetween for guiding the lateral movement of the lateral head sections 88 relative to the central head section 86. Also, the treatment head 22 is typically further provided with lateral moving assemblies or means operatively coupled between the head base 92 and the lateral head sections 88 for laterally moving the lateral head sections 88 relative to the central head section 86.

Figure 12:
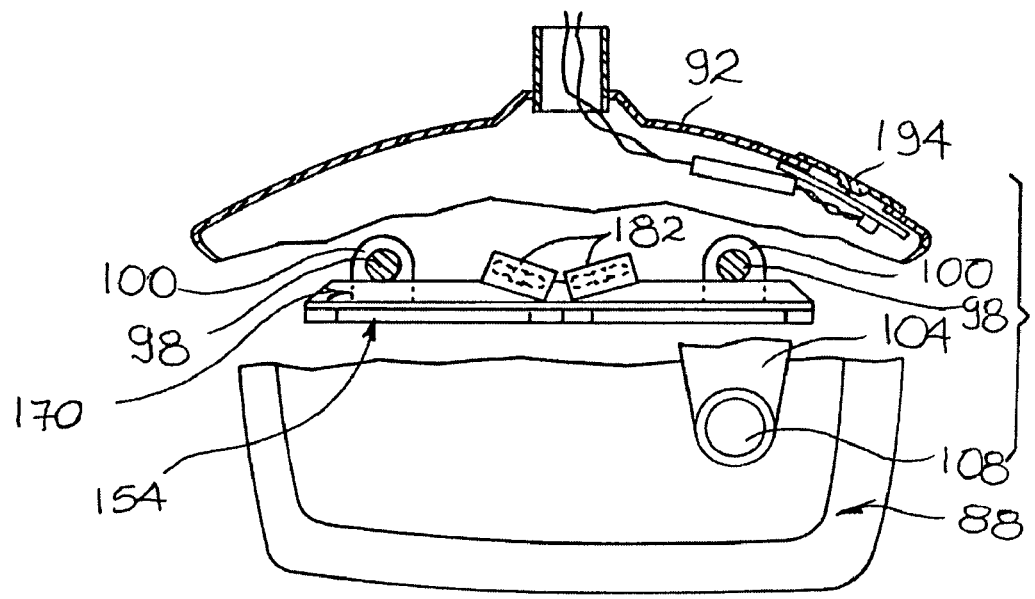
FIG. 12, in a partial longitudinal cross-sectional view with sections taken out, illustrates some of the components of the treatment head of a photoactivation device in accordance with embodiment of the present invention.

As illustrated more specifically in FIGS. 11 and 12, the lateral guiding assembly or means typically include at least one guiding rod 98 and preferably two guiding rods 98 attached to the central head section 86 and extending laterally therefrom on opposite sides of the latter. The lateral guiding assembly or means also includes corresponding guiding sleeves 100 attached to each lateral head section 88. Each one of the guiding sleeves 100 defines a corresponding guiding channel for slideably receiving a corresponding section of a corresponding guiding rod 98.

As illustrated more specifically in FIGS. 10 and 11, the lateral moving assembly or means typically includes a pair of lateral moving screws 102 (only one of which is shown in FIG. 11). Each of the lateral moving screws 102 is mechanically coupled to the head base 92 for rotation relative thereto and threadably coupled to a corresponding lateral head section 88 for moving the latter upon rotation thereof.

As shown more specifically in FIGS. 1, 5, 10 and 11, the head base 92 is typically provided with a pair of screw spacing arms 104 extending therefrom for rotatably receiving one of the lateral moving screws 102. Also, each of the lateral head sections 88 is typically provided with a corresponding lateral threaded section 106 for threadably engaging with a corresponding lateral moving screw 102.

Each lateral moving screw 102 is typically provided with a lateral screw knob 108 for facilitating manual rotation thereof. Upon rotation of a given lateral screw knob 108, the threaded coupling between the corresponding lateral moving screw 102 and the corresponding lateral threaded section 106 causes the corresponding lateral head section 88 to move relative to the corresponding spacing arm 104 and, hence, relative to the central head section 86.

In at least one embodiment of the invention, the treatment head 22 is configured and sized so as to conform substantially to the geometry of a target human face 12. Typically, the treatment head 22 is configured and sized so as to conform substantially to the geometry of a target human face 12 when the target human face 12 has anthropometric or dimensional values located between that of the lower 5th percentile of women and the higher 95th percentile of men.

FIG. 30 schematically illustrates two juxtaposed sagittal half-head sections respectively of a woman in the 5th percentile and of a man in the 95th percentile in terms of size. The women and men sagittal half-head sections 112, 114 are shown transversally sectioned about a mid-plane taken adjacent the level of the nose 110. The women half-head section 112 appears on the top part of FIG. 30 and the men half-head section 114 appears on the lower part of FIG. 30. FIG. 30 hence illustrates the variation of size that needs to be accounted for in order for the treatment head 22 to accommodate size range differences when treating head sizes having a value between that of the 5th percentile of women and the 95th percentile of men.

The human face includes a pair of ears 116 (only one of which is shown in FIG. 30) and a pair of eyes (not shown). Each of the eyes defines a laterally disposed periorbital region 118 while each of the ears 116 defines a corresponding temporal periauricular region 120. Typically, the lateral periorbital region 118 corresponds to the region of the zygomatic process and is the region wherein rhytids or wrinkles commonly referred to as crow's feet typically appear.

For example, with reference to FIG. 30, the human face 12 typically defines a central face region 122 extending substantially in the area located between the lateral periorbital regions 118. The human face also defines a pair of lateral face regions 124, each extending substantially in the region located between one of the lateral periorbital regions 118 and a corresponding temporal periauricular region 120.

As illustrated more specifically in FIGS. 21 and 30, the treatment head 22 typically defines a head proximal surface 126 adapted to face the target human face 12. The head proximal surface 126 is configured and sized so as to be at a substantially constant head surface-to-target surface operational distance 128 relative to the target human face 12 substantially throughout the treatment area thereof.

Typically, the treatment head 22 is configured and sized so that the photoactivating light source 154 is at a substantially constant light source-to-target surface operational distance relative to the target human face 12 substantially throughout the treatment area thereof. Hence, for a photoactivating light source 154 having a relatively constant fluence, the treatment head 22 is configured and sized so as to deliver a photoactivating light having a substantially constant target irradiance (or optical power density) on the treatment area. The lateral movement of the lateral head sections 88 hence typically allows the treatment head 22 to deliver the photoactivating light with substantially constant target irradiance on the target human face 12 when the target human face 12 has anthropometric values located between the 5th percentile of women and the 95th percentile of men.

Further, the central head section 86 is typically adapted to deliver photoactivating light to the nose region and, hence, is typically outwardly offset relative to the lateral head sections 88. Also, typically, at least one of the lateral head sections 88 and preferably both the lateral head sections 88 have a substantially arc-shaped cross-sectional configuration. Each lateral head section 88 is typically configured and sized for delivering photoactivating light to a corresponding area extending laterally from the nose 110 to a corresponding temporal periauricular region 120.

As illustrated more specifically in FIGS. 21 and 30, in at least one embodiment of the invention, each of the lateral head sections 88 defines a lateral head section first segment 130 for delivering photoactivating light to a corresponding lateral face section first segment extending from a first position located laterally substantially adjacent to the nose 110 to a second position located laterally substantially proximal to a corresponding lateral periorbital region 118.

Each lateral head section 88 also defines a lateral head section second segment 132 for delivering photoactivating light to a corresponding lateral face section second segment extending substantially across the corresponding lateral periorbital region 118 from the second position to a third position located laterally to the corresponding lateral periorbital region 118. Each lateral head section 88 further defines a lateral head section third segment 134 (only a portion of which is shown in FIG. 21) for delivering photoactivating light to a corresponding lateral face section third segment extending substantially from the third position to the corresponding temporal periauricular region 120.

Typically, the lateral head section first, second and third segments 130, 132 and 134 are provided with first, second and third segment light sources. The first, second and third segment light sources are positionable at a substantially constant light source-to-target surface operational distance relative to the target human face 12 substantially throughout the treatment area thereof.

In the embodiments shown throughout the Figs, the lateral head section first and second segments 130, 132 are both provided with at least one row of photoactivating light sources 154 and the lateral head section third segment 134 is provided with a pair of laterally adjacent rows of photoactivating light sources 154. Typically, the rows of photoactivating light sources 154 of the lateral head section first, second and third segments 130, 132 and 134 provide a substantially constant fluence with a substantially constant beam size and beam divergence. Optionally, some or all of these and other optical parameters may be customized without departing from the scope of the present invention.

Referring now more specifically to FIGS. 16 and 17, there is shown some of the features of a typical photoactivating light source 154. In at least one embodiment of the invention, the photoactivating light source 154 is of the Chip On Board type (COB) including an electronic light generating component mounted directly on the mounting surface of a corresponding Printed Circuit Board (PCB). Typically, the electronic light generating component includes at least one LED and preferably a substantially elongated LED matrix 138. In FIG. 17 only a pair of LEDs 136 making up the LED matrix 138 is shown. Also, the LEDs 136 are shown enlarged relatively to the remainder of the LED matrix 138. Furthermore, the LEDs 136 are shown having a substantially disc-shaped cross-sectional configuration. It should however be understood that other types of LEDs 136 could be used without departing from the scope of the present invention. For example, typically, the LED matrix 138 consists of a substantially flat LED strip. It should also be understood that other types of light generating components could be used without departing from the scope of the present invention.

In an embodiment, LED matrix 138 consists of rows and columns of LEDs. The matrix can have an equal or unequal number of rows and columns. Additionally, each row and column can have a varying number of LEDs as compared to an adjacent row or column. Each row or column can light simultaneously or light in a "cascade" fashion. The LEDs can cascade so quickly as to be preserved as simultaneously by the human eye. LED matrix can be designed to configure to a specific region or shape of the treatment head 22 to provide light rays without unnecessary exposure. Further, sections of the LED matrix do not necessarily all light for every treatment and alternating rows and columns can light or some not light at all for a specific treatment.

Typically, the photoactivating light source 154 also includes a lens optically coupled to the electronic light generating component 138 for guiding the photoactivating light rays 142 (shown schematically in FIGS. 30 and 31) emitted by the electronic light generating component 138 so that the photoactivating light source 154 emits photoactivating light according to a predetermined light emission pattern. In the example shown throughout the Figures, the lens is used for focusing the photoactivating light rays 142. It should, however, be understood that the lens could also be used for dispersing the photoactivating light rays 142 depending on the type of light generating component being used.

Typically, the lens includes a substantially elongated lens plate 140. The lens plate 140 is typically maintained in a spaced relationship relative to the LED matrix 138 by a Chip On Board casing 143.

The lens plate 140 defines a pair of longitudinally extending lens plate side edges 144. The Chip On Board casing 143 typically has a substantially elongated configuration defining a pair of longitudinally opposed Chip On Board casing longitudinal ends 146. The Chip On Board casing 143 also has a pair of longitudinally extending Chip On Board casing side walls 148.

Each of the Chip On Board casing side walls 148 is typically in a substantially proximal relationship relative to a corresponding lens plate side edge 144. The Chip On Board casing side walls 148 diverge laterally outwardly adjacent the casing longitudinal ends 146 so as to form corresponding Chip On Board casing attachment flanges 150.

The Chip On Board casing attachment flanges 150 are typically provided with attachment apertures 152 extending therethrough for receiving conventional attachment components such as screws adapted to be used for mounting corresponding Chip On Board casing 143 to a suitable supporting surface as will be hereinafter disclosed in greater details.

As illustrated more specifically in FIG. 20, the photoactivating light sources 154 are typically grouped in pairs positioned in side by side and contiguous relationship relative to each other with their respective attachment flanges 150 in a proximal relationship relative to each other. In such a configuration, the remainder of the corresponding adjacent casing side walls 148 of laterally adjacent photoactivating light sources 154 delimit a Chip On Board casing cooling channel 156 therebetween for allowing the flow of a cooling fluid therethrough as will be hereinafter explained in greater details.

Each photoactivating light source 154 typically also includes control electronics 158 typically positioned adjacent one of the Chip On Board casing longitudinal ends 146. Chip On Board cables 160 typically extend from an undersurface of the Chip On Board casing 143 for allowing connection thereof to a suitable connector. Sealing of the photoactivating light source module is typically provided by a self-adhesive tape 162 located at the Chip On Board Casing longitudinal end 146 opposite the electronic controls 158.

Typically, each photoactivating light source 154 is designed for emitting pulsed photoactivating light having a target irradiance of substantially greater than 0.04 W/cm$^2$, a target fluence of approximately between 0.05 and 10 J/cm$^2$ and a predetermined pulsing pattern. More specifically, the target irradiance typically has a value of approximately 0.05 W/cm$^2$ at the centre of LED array and the target fluence has a value of approximately 4 J/cm$^2$. Specifically, an embodiment utilizes a target fluence of 4.5 J/cm$^2$ and greater. Another embodiment is a fluence between 4.5 and 10 J/cm$^2$.

The photoactivating light emitted by the photoactivating light sources 154 typically has a wavelength value of approximately between 600 nm and 700 nm. More specifically, the photoactivating light typically has a peak wavelength value of approximately 660 nm±10 nm.

The pulsing pattern of the photoactivating light sources 154 typically includes a pulse width of approximately 0.0005 seconds and a pulse interval of approximately 0.00015 seconds. The predetermined pulsing pattern also typically includes pulse trains of between approximately 3 and 5 pulses with pulse train intervals of approximately 0.00155 seconds. It should be understood that other pulsing patterns could be used without departing from the scope of the present invention.

Typically, with a target irradiance of approximately 0.05 W/cm$^2$ at the centre of LED array and a target fluence of approximately 4.5 J/cm$^2$, the head surface-to-target surface operational distance 128 has a value of approximately 2.5 cm+/−1 to 3 mm. It should however be understood that the head surface-to-target surface operational distance 128 could have another value without departing from the scope of the present invention.

The above factors are interrelated and all combine to produce different irradiances. For example, an LED array having a power density 0.05 W/cm$^2$, a pulse width of 0.005 seconds, a pulse interval of 0.00015 seconds, having a 4 pulse pulse train with pulse train intervals of 0.00155 seconds for a total of 160 seconds generates a total irradiance of 500 W/cm$^2$. Changing any one of the parameters can alter the irradiance or altering different parameters can result in the same irradiance.

Typically, although by no means exclusively, the photoactivating light source pointing tolerance has a value of approximately ±3 degrees and a beam divergence (FWHM) of approximately 50±5 degrees. The spectral width (FWHM) has a value of approximately 30±5 nm. The lens plate 140 is typically of the cylindrical type, with, for example, UL94 V-2 polycarbonate used as lens material.

Figure 32:
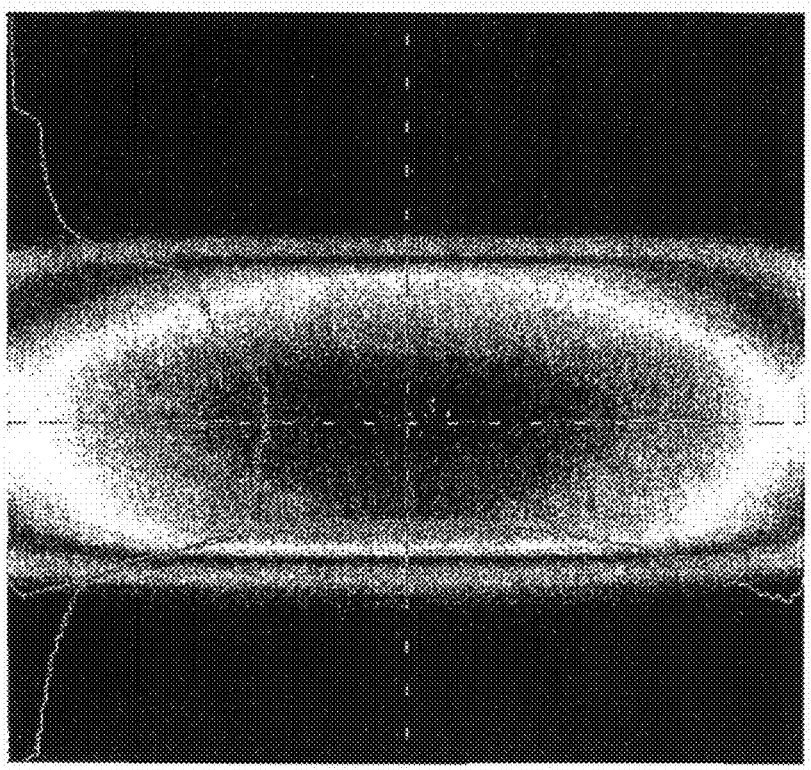
FIG. 32, in a top view illustrates the typical lighting pattern created by a lighting module part of a photoactivation device in accordance with an embodiment of the present invention.
Figure 33:
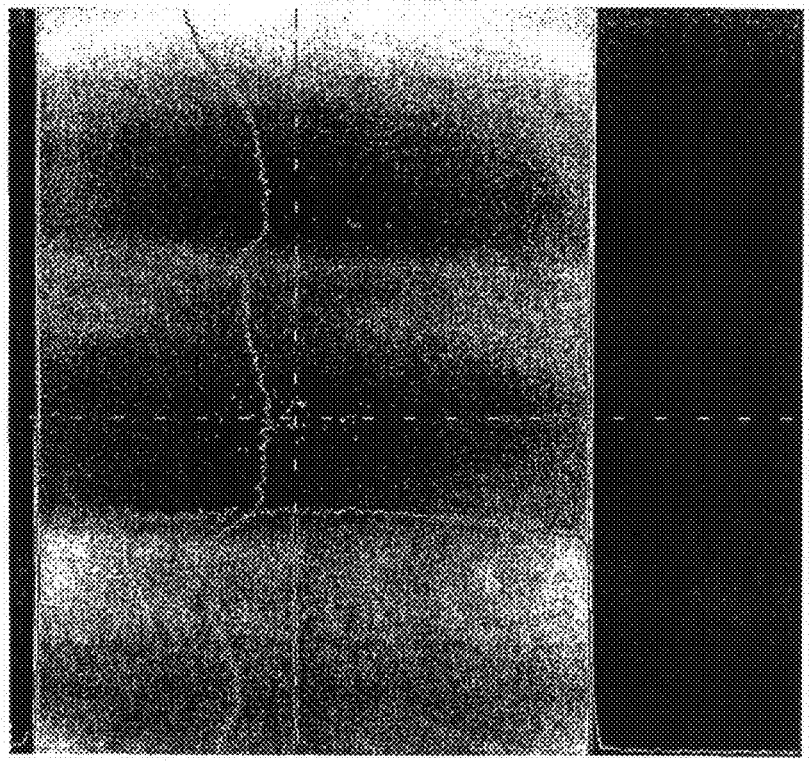
FIG. 33, in a top view, illustrates the lighting pattern typically created by three adjacent lighting modules.
Figure 34:
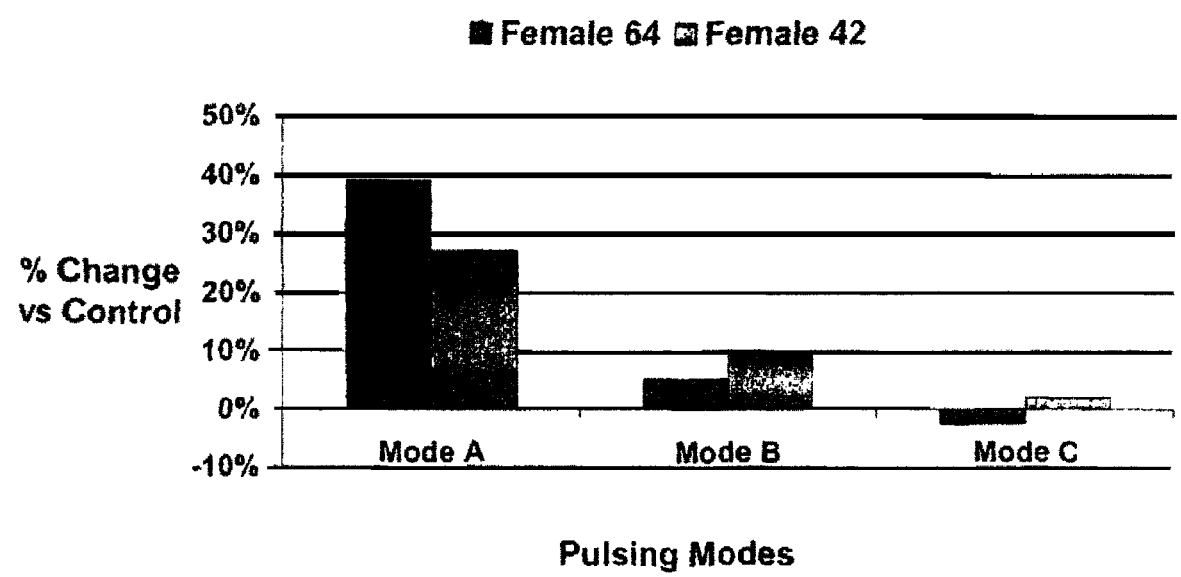
FIG. 34 illustrates a percent change in average procollagen in control experiment compared to over one-month (11 treatments) irradiation for two human reconstructed skin samples further to irradiation with radiation presenting a power density temporal profile according to the invention; in vitro treatment of normal human reconstructed skin was performed by a pulsed LED light source for 3 times a week during 4 consecutive weeks.
Figure 35:
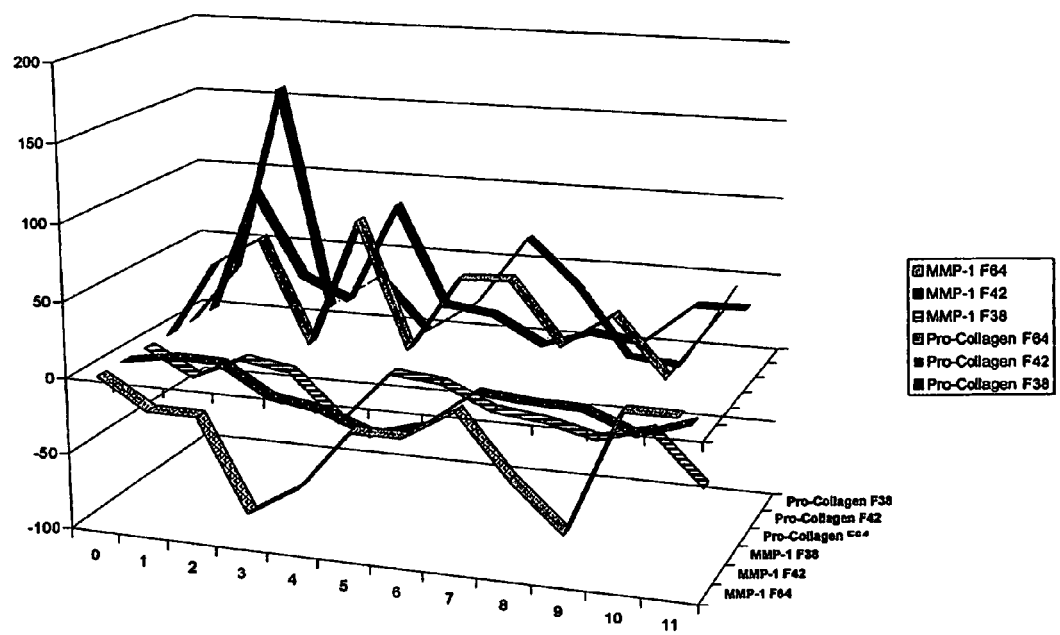
FIG. 35 illustrates a percent variation in procollagen and MMP-1 activity over a one-month period punctuated with the 11 LED treatments relating to FIG. 34.
Figure 36:
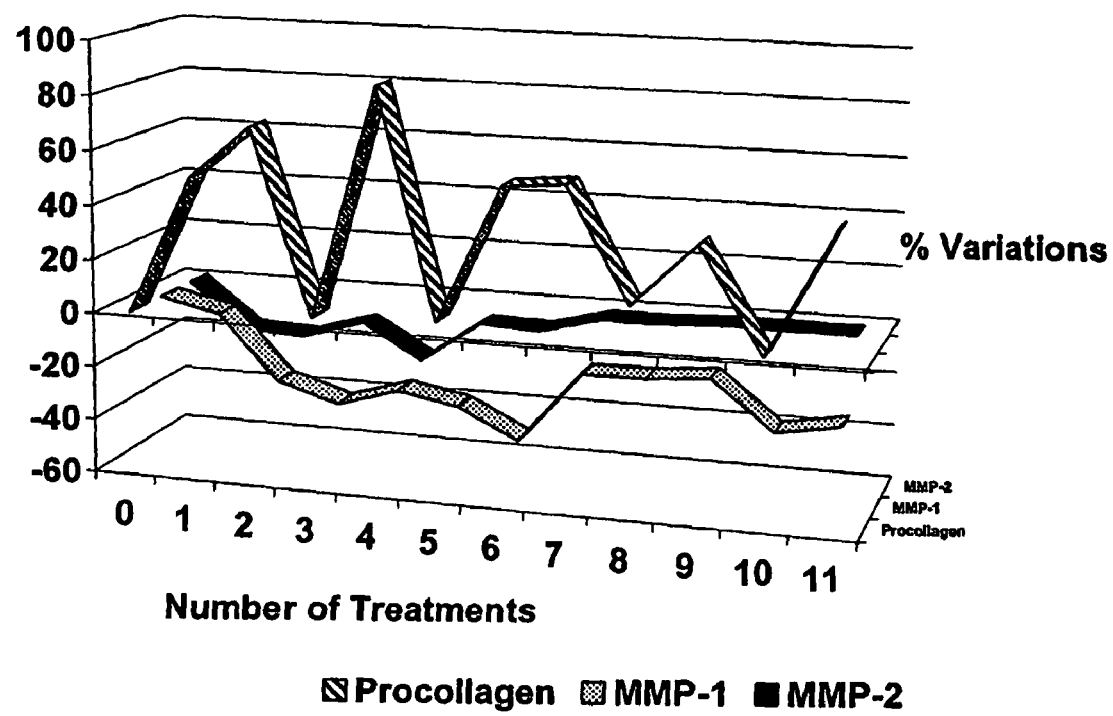
FIG. 36 illustrates a percent variation in procollagen, MMP-1 and MMP-2 activities over a one-month period punctuated with the 11 LED treatments relating to FIG. 34.
Figure 37:
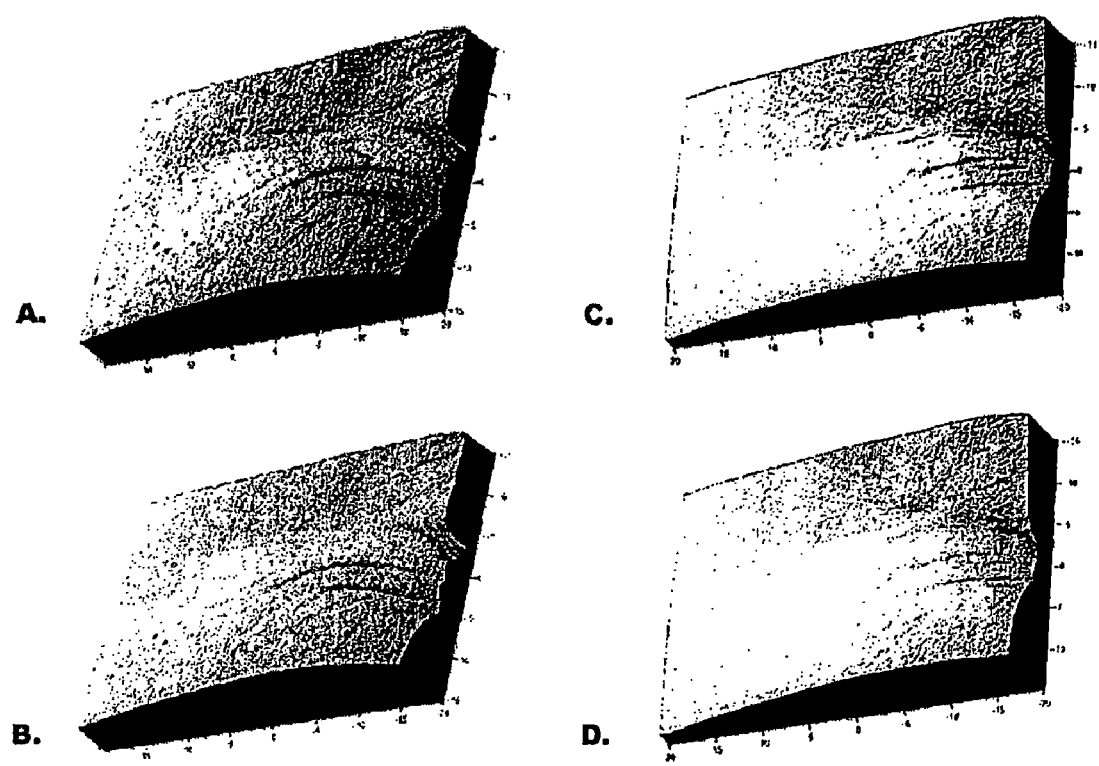
FIG. 37A illustrates PRIMOS computerized pre- and post-treatment pictures of the right crowfeet area of a human subject for in vivo pulsed radiation treatments according to the invention (12 treatments were performed); Pre-treatment picture color-coded topography of the right crowfeet area; Darker areas indicate deeper wrinkle surface.
FIG. 37B illustrates PRIMOS computerized pre- and post-treatment pictures of the right crowfeet area of a human subject for in vivo pulsed radiation treatments according to the invention (12 treatments were performed); In addition to topography, skin texture and pore size can also be appreciated before treatment in phaseshift mode photography of the right crowfeet area.
FIG. 37C illustrates PRIMOS computerized pre- and post-treatment pictures of the right crowfeet area of a human subject for in vivo pulsed radiation treatments according to the invention (12 treatments were performed); Post-treatment color-coded topography after twelve treatments. Improvements in wrinkle depth and number are clearly noticeable when compared with pre-treatment color-coded topography (FIG. 37A)
FIG. 37D illustrates PRIMOS computerized pre- and post-treatment pictures of the right crowfeet area of a human subject for in vivo pulsed radiation treatments according to the invention (12 treatments were performed); Post-treatment phaseshift mode photography after twelve treatments, exhibiting a smoother surface/tighter skin and noticeable reduction in pore size.

FIGS. 32 and 33 illustrate respectively a typical irradiance pattern produced by a single photoactivating light source 154 and three laterally adjacent photoactivating light sources 154 respectively. As can be seen from these Figures, the optical power density or irradiance is substantially constant throughout the lighting range.

Typically, the maximum to minimum deviation is in the order of 15% along the length of the photoactivating light source 154. Also, preferably, the photoactivating light sources 154 are designed so that the irradiance or optical power density remains relatively constant throughout the lifetime thereof. For example, the photoactivating light sources 154 may be designed so that the irradiance does not fall to less than 85% of initial irradiance after 2,000 hours of operation. It should be understood that other types of photoactivating light sources having other optical, mechanical, electrical or interface characteristics could be used without departing from the scope of the present invention.

As mentioned previously, the head proximal surface 126 is typically spaced relative to the target human face 12 by a head surface-to-target surface operational distance 128. As illustrated more specifically in FIG. 19, the treatment head 22 and the treatment area hence typically define a treatment head-to-treatment area spacing 164 therebetween.

Typically, the treatment head 22 also includes a treatment area cooling assembly or means for cooling the treatment area. In one embodiment of the invention, the treatment area cooling assembly or means includes a cooling air flowing assembly or means for creating a treatment area air flow 168 flowing at least partially in the treatment head-to-treatment area spacing 164 for cooling the treatment area. The treatment area air flow 168 is adapted to cool the treatment area by convectively cooling the treatment area and/or evacuating heat from the treatment head-to-treatment area spacing 164. The treatment area air flow 168 is also adapted to allow for evacuation of carbon monoxide and/or other by-products produced by the breathing of the intended patient 14.

In the embodiment shown throughout the Figs. the treatment area air flow 168 is induced by sucking or pulling air away from the treatment head-to-treatment area spacing 164. In an alternative embodiment of the invention, the treatment area air flow 168 is induced by blowing air into the treatment head-to-treatment area spacing 164.

Regardless of whether the treatment area air flow 168 is induced by blowing cooling air into the treatment head-to-treatment area spacing 164 or by sucking or pulling heated air away from the treatment head-to-treatment area spacing 164, the cooling air may optionally be pre-cooled to further enhance its cooling effect. Both blowing cooling air at a patient 14 or pulling heated air away from a patient 14, will result in a cooling effect on the patient's 14 skin. This can comfort the patient as well as cool the skin to prevent overheating or burning the patient 14.

Also, optionally, the cooling air may be mixed with various agents such as therapeutic agents, photoactivation promoting agents or the like. Furthermore, the cooling air may optionally mixed with anaesthetic agents such as sedating agents for at least partially sedating the patient, local anaesthetic agents for at least partially providing a local anaesthesia of the treatment site or the like.

Typically, the treatment head 22 also includes a light source cooling assembly or means for cooling the photoactivating light sources 154. Typically, the light source cooling assembly or means includes a device cooling air flowing assembly or means for creating a light source air flow 166 for convectively cooling the photoactivating light sources 154 and associated components. In the embodiment shown throughout FIGS. 13-20, the device cooling air flowing assembly or means also creates the treatment area air flow 168 for cooling the treatment area. More specifically, the light source air flow 166 creates a vacuum for inducing the treatment area air flow 168. Alternatively, the light source air flow 166 and the treatment area air flow 168 may be induced separately.

As illustrated more specifically in FIGS. 16, 18 and 19, the photoactivating light sources 154 are typically thermally coupled to a heat sink 170. The cooling air flowing assembly or means allows the light source air flow 166 to cool the heat sink 170 and to create a vacuum across the heat sink 170 for inducing the treatment area air flow 168. The heat sink 170 includes a heat sink base plate 172. The heat sink base plate 172 defines a heat sink base plate first surface 174 and an opposed heat sink base plate second surface 176. The heat sink base plate 172 has at least one, and preferably a plurality of air flow apertures 178 extending therethrough. The air flow apertures 178 can be disposed in a predetermined pattern to form a specific air flow or can be randomly placed.

The cooling air flowing assembly or means allows the light source air flow 166 to flow over at least a portion and preferably most of the heat sink base plate first surface 174 so as to create a vacuum drawing the treatment area air flow 168 from the heat sink base plate second surface 176 through the air flow apertures 178.

The heat sink 170 typically also includes heat dissipating fins 180 extending from the heat sink base plate first surface 174. The heat dissipating fins 180 define fin channels 184 therebetween. The cooling air flowing assembly or means allows the light source air flow 166 to flow at least partially between the heat dissipating fins 180. Typically, the cooling air flowing assembly or means includes at least one air fan 182 in fluid communication with the fin channels 184.

As illustrated more specifically in FIGS. 15, 16, 18 and 19, the heat dissipating fins 180 are configured so as to define at least one and preferably two fan receiving recesses 186. The fan receiving recesses 186 are adapted to at least partially receive corresponding venting air fans 182. The fan receiving recesses 186 are typically configured, positioned and sized so that at least one and preferably both air fans 182 are positioned at an angle relative to both the heat sink base plate 172 and the heat dissipating fins 180.

Typically, the treatment head 22 includes a plurality of heat sinks 170 positioned in a side-by-side relationship relative to each other. Each heat sink 170 has a corresponding heat sink base plate 172 and each heat sink base plate 172 has a substantially elongated configuration extending between a pair of longitudinally opposed base plate longitudinal ends 188. The heat dissipating fins 180 extend substantially longitudinally along corresponding heat sink base plates 172.

The fan receiving recesses 186 are typically positioned substantially intermediate the plate longitudinal ends 188. As shown more specifically in FIGS. 18 and 19, the air fans 182 are positioned so as to be in a substantially symmetrically opposite relationship relative to each other. Each air fan 182 is positioned so as to draw a corresponding light source air flow portion from a corresponding base plate longitudinal end 188.

As shown more specifically in FIG. 19, each pair of air fans 182 defines a fan-to-fan spacing 190 therebetween. The air fans 182 are configured, sized and positioned so that a portion of the cooling air that they draw will penetrate in the fan-to-fan spacing 190 according to a flow pattern schematically represented and designated by the reference numeral 192. The flow pattern 192 of the air drawn by the air fans 182 in the fan-to-fan spacing 190 is such that it allows cooling of the portion of the heat sink base plate 172 located thereunderneath. Alternately, air fans 182 can be disposed in base 24 or a separate housing (not illustrated) and placed in fluid communication with the heat sinks 170 and perform the same function as if placed in the fan receiving recesses 186.

As illustrated more specifically in FIGS. 10 and 20, the Chip On Board casings 143 are mounted on the heat sink base plate second surface 176 with the Chip On Board casing cooling channels 156 substantially in register with at least some of the air flow apertures 178 so as to allow the flow of air from the sink base plate first surface 174 to the sink base plate second surface 176. As illustrated more specifically in FIG. 19, when the air fans 182 draw the light source air flow 166 over the heat sink base plate first surface 174, a vacuum is created in the air flow apertures 178. This vacuum draws the treatment area flow 168 from the heat sink base plate second surface 176, through both the Chip On Board casing cooling channels 156 and the corresponding air flow apertures 178 in register therewith so that the treatment area air flow 168 eventually merges with the light source air flow 166 over the heat sink base plate first surface 174.

As illustrated more specifically in FIG. 20, the treatment head 22 typically includes rows 199 of photoactivating light sources 154 in substantially side-by-side and contiguous relationships relative to each other. Each row 199 is typically formed by juxtaposing a pair of photoactivating light sources 154 with their respective longitudinal axis in a substantially co-linear relationship relative to each other. Optionally, an air flowing slot 196 extends through the heat sink base plate 172 between longitudinally adjacent photoactivating light sources 154.

As illustrated more specifically in FIG. 11, the central head section 86 and the lateral head sections 88 are each provided with independent sets of strategically positioned optical probes air fans 182. Air sucked into the casings formed respectively by the central head section 86 and the lateral head sections 88 is adapted to flow through corresponding pairs of longitudinally opposed central and lateral air inlet grids 181, 183 (only one inlet grid 181, 183 part of each pair of air inlet grids 181, 183 is illustrated in FIG. 5).

As illustrated more specifically in FIG. 9, air flowing out of the casing formed by the central head section 86 is adapted to flow through a corresponding central air outlet grid 185 located substantially longitudinally opposite the screen 194. As illustrated more specifically in FIGS. 1, 5 and 9, air flowing out of the casing formed by each lateral head section 88 is adapted to flow through a corresponding substantially radially disposed lateral air outlet grid 187.

In an alternative embodiment of the invention, the heat dissipating assembly or means includes as a so-called heat spreader. The latter pertains to a member which channels heat from a semi-conductor die to leads which exit the die package. A heat sink and a heat spreader may also be used together to cool the device. It should be understood that yet other forms of heat dissipating means could be used without departing from the scope of the present invention.

The photoactivation device 10 typically further includes a position evaluating assembly or means for evaluating the position of the photoactivating light source relative to the target surface. Typically, the photoactivation device 10 also includes an information providing assembly or means for providing information regarding the position of the photoactivating light source relative to the target surface.

As illustrated more specifically in FIGS. 5 and 8, the information providing means typically includes a visual display such as an LCD screen 194 or the like for providing a visual display regarding the position of the photoactivating light source relative to the target surface. It should be understood that other types of visual display means could be used without departing from the scope of the present invention. Also, the information providing assembly or means may use audio, tactile or other sensory modes or combinations thereof to provide information regarding the position of the photoactivating light source relative to the target surface without departing from the scope of the present invention.

In at least one embodiment of the invention, the information providing means includes a direction indicating means for providing information regarding the direction the photoactivating light source should be moved to reach a predetermined target position relative to the target surface. In at least one embodiment of the invention, the direction indicating means includes an electronic circuitry coupled to the position evaluating means for displaying arrows indicating to an intended user the direction in which the treatment head 22 should be moved to reach a predetermined target position relative to the target surface. Typically, optimal positioning of the treatment head 22 is achieved by simply following step-by-step "real time" optical instructions provided on the LCD screen 194.

The treatment head 22 is typically provided with control buttons 195 or the like, conveniently located substantially adjacent the LCD screen 194 for controlling the display parameters, operational parameters or any other suitable parameters. Optionally such parameters could also be controlled using a remote control (not shown). Optionally, the parameters could also be controlled using other type of user interfaces such as through voice command or the like without departing from the scope of the present invention.

In at least one embodiment of the invention, the photoactivation device 10 includes an actuating means for taking a predetermined course of action depending on the position of the photoactivating light source relative to the target surface or other operational parameters. For example, the actuating means may include an automatic positioning means for automatically repositioning the photoactivating light source towards a predetermined target position relative to the target surface.

In at least one embodiment of the invention, the position evaluating means allows for evaluation of the three-dimensional coordinates of the photoactivating light source relative to the target surface. In another embodiment of the invention, the position evaluating means allows for evaluation only of the distance between the photoactivating light source and the target surface.

Typically, the position evaluating means includes at least one and preferably a plurality of non-contacting probes for evaluating the distance between the photoactivating light source and the target surface without contacting the target surface. The non-contacting probes are typically optical probes although other parameters such as temperature, sound waves or the like could be used without departing from the scope of the present invention.

In at least one embodiment of the invention, the photoactivation device 10 also includes an aiming means operatively coupled to the position evaluating means for allowing aiming of the position evaluating means towards a target position located on the target surface. The aiming means may take any suitable form including a visible aiming beam of light for visibly pointing towards the target position.

Referring now more specifically to FIGS. 22 through 29, there is shown in greater details an optical probe 198 part of a typical position evaluating assembly or means in accordance with an embodiment of the present invention. As shown schematically in FIG. 27, the optical probe 198 includes a distance probe light source 200 for projecting a probe light ray along a projection optical axis 202 towards the target surface 204. The optical probe 198 also includes a distance probe target sensor 206 for sensing the probe light ray travelling along a target sensor optical axis 208 once the probe light ray has been reflected by the target surface 204.

The distance probe light source 200 and the distance probe target sensor 206 are configured, sized and positioned so that the projection optical axis 202 and the target sensor optical axis 208 are angled relative to each other and intercept each other on the target surface 204 substantially only when the target surface 204 is spaced from the photoactivating light source by a predetermined target-to-photoactivating light source spacing distance 210. In other words, the distance probe light source 200 and the distance probe target sensor 206 are positioned, configured and sized so that the distance probe target sensor 206 will only receive or be able to sense the probe light ray projected by the distance probe light source 200 and reflected by the target surface 204 when the target surface 204 is spaced from the photoactivating light source 200 by the predetermined target-to-photoactivating light source spacing distance 210 or within a predetermined range thereof.

Hence, the optical probe 198 is configured so that when the photoactivating light source is spaced from the target surface 204 by the predetermined target-to-photoactivating light source spacing distance 210, the target sensor optical axis 208 and the projection optical axis 202 are angled relative to each other and intercept each other substantially on the target surface 204 allowing the distance probe target sensor 206 to sense the probe light ray.

The optical probe 198 typically includes at least one distance probe offset sensor for sensing the probe light ray when the latter travels along an offset sensor optical axis. In the embodiment shown throughout the Figures, the optical probe 198 includes both a distance probe near sensor 212 and a distance probe far sensor 214 for sensing the probe light ray when the latter travels along respectively a near sensor optical axis 216 and a far sensor optical axis 218.

As illustrated more specifically in FIG. 28, the distance probe light source 200 and the distance probe far sensor 214 are configured, sized and positioned so that the probe light ray is reflected from the target surface 204 so as to travel along the far sensor optical axis 218 when the photoactivating light source is spaced from the target surface 204 by a far spacing distance 219 within a predetermined far spacing range. Similarly, as illustrated in FIG. 29, the distance probe light source 200 and the distance probe near sensor 212 are configured, sized and positioned so that the probe light ray is reflected from the target surface 204 so as to travel along the near sensor optical axis range 216 when the photoactivating light source is spaced from the target surface 204 by a near spacing distance 217 located within a predetermined near spacing range.

The near and far sensors 212 and 214 are typically configured so as to be able to sense or be activated by light rays emanating from within predetermined corresponding angular optical range 216, 218 corresponding to the predetermined near and far spacing ranges. Typically, the near, far and target spacing ranges are substantially contiguous relative to each other so as to form a substantially continuous operational spacing range.

Typically, the distance probe light source 200 allows for the emission of a probe light ray having a frequency located within the infra-red spectrum. Accordingly, the distance probe target, near and far sensors 206, 212 and 214 are typically adapted to sense or be activated by light rays in the infra-red spectrum. The infra-red spectrum may be particularly useful for distance probing with darker skinned patients. It should, however, be understood that the distance probe light source 200 could be used for emitting probe light rays within other frequency ranges without departing from the scope of the present invention.

Typically, the optical probe 198 also includes an aiming assembly or means operatively coupled to the position evaluating assembly or means for allowing aiming of the probe light ray towards a target position located on the target surface 204. Typically, the aiming means includes a visible aiming beam of light for visibly pointing towards the target surface. The aiming beam of light may be produced by any suitable means such as an aiming LED 224 shown in FIG. 25.

As illustrated more specifically in FIGS. 22 through 26, the optical probe 198 typically includes an optical probe casing. The optical probe casing, in turn, includes a light source cavity 226 for protectively receiving at least part of the distance probe light source 200, a target sensor cavity 228 for protectively receiving at least part of the distance probe target sensor 206, a near sensor cavity 230 for protectively receiving at least part of the distance probe near sensor 212 and a far sensor cavity 232 for protectively receiving at least part of the distance probe far sensor 214.

The optical probe casing is typically configured and sized for housing the distance probe light source 200, the distance probe near sensor 212, the distance probe far sensor 214 and the distance probe target sensor 206 in sequential side-by-side order and in an angled relationship relative to each other. Typically, the optical probe casing defines a casing input end 234 and a substantially opposed casing output end 236.

The light source cavity 226 has a generally elongated configuration and extends through the optical probe casing substantially from the casing input end 234 to the casing output end 236. The light source cavity 226 typically has a substantially frusto-conical configuration tapering towards the casing output end 236.

Typically, the optical probe 198 further includes a light source alignment assembly or means for allowing adjustment of the direction of the projection optical axis 202 relative to the optical probe casing. Typically, the distance probe target sensor 206, the distance probe far sensor 214 and the distance probe near sensor 212 are also provided with substantially identical or different angle adjustment means.

As illustrated more specifically in FIG. 25, the light source alignment assembly or means typically includes a probe light source mounting component 238 for mounting the distance probe light source 200 on the optical probe casing. Also, the light source cavity 226 typically has a light source mounting section 240 located substantially adjacent the casing input end 234 for receiving the light source mounting component 238 and allowing selective movement thereof within the light source mounting section 240. Typically, the light source cavity 226 defines a cavity longitudinal axis and the light source mounting section 240 is configured and sized for allowing selective movement of the light source mounting component 238 therein along a substantially arc-shaped adjustment trajectory 242.

As shown more specifically in FIG. 24, the light source mounting component 238 typically includes a substantially cylindrical light source receiving channel 244 for receiving the distance probe light source 200 and a pair of substantially radial mounting component guiding flanges 246. The light source mounting component 238 defines a pair of opposed and substantially flat mounting component guiding surfaces 248 (only one of which is shown in FIG. 24). At least one of the mounting component guiding surfaces 248 is provided with a corresponding guiding tongue 250 extending substantially outwardly therefrom.

As illustrated more specifically in FIGS. 22, 23, 25 and 26, the optical probe casing defines a pair of opposed probe casing main walls 252, 253 maintained in a spaced-apart relationship relative to each other by a casing peripheral wall 255 extending therebetween. The casing main walls 252, 253 are adapted to be releasably assembled together using conventional attachment components such as screws, bolts or the like (not shown) extending through corresponding casing wall attachment apertures 251.

As illustrated in FIG. 25, adjacent to the casing output end 236, the casing peripheral wall 255 is provided with a light source output aperture 256 and a casing target aperture 258 both extending therethrough in optical communication respectively with the light source cavity 226 and the target sensor cavity 228. Similarly, the casing peripheral wall is also provided with a near optical slot 260 and a far optical slot 262 extending therethrough in optical communication respectively with the near sensor cavity 230 and the far sensor cavity 232.

At least one and preferably both casing main walls 252, 253 have guiding grooves 254, 254' formed respectively therein for guidingly receiving a corresponding guiding tongue 250. Typically, the guiding grooves 254' formed in the casing main wall 253 extend therethrough so as to allow access to the corresponding guiding tongues 250 without requiring disassembly of the casing main wall 252, 253.

Typically, the guiding tongues 250 that are inserted in corresponding guiding grooves 254' are provided with corresponding tongue notches 264 formed therein. The tongue notches 264 are adapted to allow insertion therein of a substantially pointed object. The substantially pointed object, in turn, is adapted to be used for facilitating the sliding of the guiding tongue 250 along the guiding grooves 254, 254' during adjustment of the alignment of the direction of the projection optical axis 202, the target sensor optical axis 208, the projection optical axis 202, the near sensor optical axis 216 and/or the far sensor optical axis 218 relative to the optical probe casing.

The light source alignment assembly or means typically further includes an alignment locking assembly or means for releasably locking the probe light source mounting components 238 in their respective aligned relationship relative to their respective light source mounting sections 240. The alignment locking assembly or means typically includes locking apertures 266 formed in the casing main wall 253 substantially adjacent the guiding grooves 254'. The alignment locking assembly or means typically also includes locking screws or the like (not shown) threadably insertable in corresponding locking apertures 266.

Each locking screws is configured, sized and positioned so that a distal tip thereof is adapted to frictionally contact a corresponding mounting component guiding surface 248 for frictionally preventing the movement of a corresponding probe light source mounting component 238 in its corresponding light source mounting section 240.

As illustrated more specifically in FIG. 10, the position evaluating assembly or means typically includes a set of strategically positioned optical probes 198. Although the optical probes 198 shown in FIG. 10 are only visible in the central head section 86, typically, the central head section 86 and the lateral head sections 88 are each provided with independent sets of strategically positioned optical probes 198 so as to allow for independent assessment of their respective position relative to the target surface.

Typically, the optical probes 198 are positioned in the casing cooling channels 156. It should however be understood that the optical probes 198 could be otherwise located without departing from the scope of the present invention.

Also, other types of position measuring or evaluating means could be used without departing from the scope of the present invention. In an alternative embodiment of the invention (not shown), the position measuring means includes a light source for directing a measuring beam towards the target surface and a photodetector positioned to receive a portion of the measuring beam reflected from the target surface.

A beam splitter is positioned between the light source and the target surface to reflect a portion of the light source measuring beam to a monitor photodetector. The monitor photodetector receives the reflected beam and provides an output signal representative of the position of the beam splitter reflected beam and, hence, the position of the light source with respect to an idealised position.

In one embodiment, the photodetector develops a monitor output signal representative of the deviation between an idealised centre line and an actual centre line of the light source. The monitor output signal may be employed for display purposes. The monitor output signal may also be employed with positioning means to displace the light source from its actual position towards the ideal position so as to reduce the measurement error associated with the actual position of the light source.

Optionally, the device 10 may further be provided with sensing means for sensing environmental and/or target tissue parameters that may have an influence on the value of the optimal head surface-to-target surface operational distance 128 and/or the optimal power density and/or the optimal value for other operational parameters. For example, the device 10 may optionally be further provided with a temperature sensor, a skin pigmentation or color sensor, a skin thickness sensor or the like.

The device 10 is optionally further provided with means for allowing optimal adjustment of selected operational parameters for achieving a predetermined photoinduced effect. The means for allowing optimal adjustment of selected operational parameters typically allows for global or localised adjustment of the selected operational parameters.

Light-based radiation therapy is effective in a number of clinical situations, but the photobiological basis of this therapy remains, at least in part, misunderstood. Wavelengths both in the visible (380-700 nm (nanometers)) and infrared regions (700-1000 nm) of the electromagnetic spectrum are effective in such therapies, often providing similar clinical results, despite dramatic differences in their photochemical and photophysical properties.

It is established that the amplitude of laser light stimulation in biological tissues depends on a set of at least four parameters, besides the wavelength of light: 1. light intensity threshold (Irradiance or $I_0$), 2. beam cross section (spot size), 3. total irradiation time ($\Delta t_{tot}$) and 4. energy dose (fluence). The relevant parameters for modulation are interrelated according to this equation:

$$\text{Fluence} = I_{stim} \times \Delta t_{tot}$$

where $I_{stim} \geq I_0$

In biological tissues, light intensities lower than threshold values $I_0$ do not produce modulatory effects, even under prolonged irradiation time $\Delta t_{tot}$. Fluence and power density, also referred to as irradiance, are then independent from each other as allowed through the use of non-constant power densities as a function of time. The effective range of fluence in the above equation is given by the Arndt-Shultz curve showing different modes of cell reaction at different levels of energy density (57).

Besides the above-mentioned parameters, beam repetition frequencies in periodic time-varying irradiations also have extended influence on the activation/inhibition of biological tissues. Direct effects of pulse frequency received support on the experimental side from the observation of additional Ca2+ uptake in macrophage (58) and an enhanced chemiluminescence in murine splenocites (59) after irradiation with pulsed semiconductor lasers of suitable pulse duration and repetition frequency. There has also been support from the clinical side (15).

By far, the majority of laser applications in dermatology use laser-induced heating. In contrast to photoactivation/inhibition, heating does not require any particular thermal photon energy. "Selective photothermolysis" uses heat at a higher level. This approach changed the scope of lasers in dermatology over the 15 years since its formulation (56). This term was coined to describe site-specific, thermally mediated injury of microscopic, specific tissue targets by selectively absorbed pulses of light (55, 56). Such confined energy coagulates the target (i.e. oxyhemoglobin in blood vessels, melanin in pigmented cells) without injury to the surrounding skin.

Therefore, exposure duration and relaxation time are relatively important in the well-established selective photothermolysis concept. The so-called thermal relaxation time (TRT) or time required for significant cooling of a small target structure plays a major role in selective photothermolysis. Thermal conduction dominates the cooling of microscopic structures in skin. However, more microscale radiational cooling studies are needed (55). When the laser exposure is less than the TRT, maximal thermal confinement will occur.

The quantum yield of a photochemical reaction is the probability that photochemistry will occur when the energy of light is absorbed by the system. Hence, the true photochemical sensitivity of a system is the product of two probabilities: the probability that light of a given wavelength will be absorbed and the probability that the absorbed light will be responsible of a chemical change. Therefore, once a therapeutic benefit has been found for a given wavelength of light, the optimum energy parameters and the optimum number of treatments to achieve a clinical benefit must be determined.

The light activation of enzymes is one of the fastest growing fields of photobiology, and several reviews on this subject have been published (7-9). Enzymes are catalysts. In principle, one photon can activate one enzyme molecule, which in turn can process many thousands of substrate molecules. The activation of enzymes provides a huge amplification factor for initiating a biological response with light. Such remarkable amplification potential may explain why low level laser radiation therapy is effective. If the effect of one photon can be amplified biologically, then not a lot of photons are required to produce a physiological effect. Proper parameters of light stimulating a given enzyme and leading to the beneficial therapeutic effect must be optimized and established. There are a number of ways suggested, both direct and indirect, to light-activate or inhibit an enzyme.

Activate (Produce) the Substrate

For example, if a cell is exposed to UV radiation, the photochemical damage that occurs in the DNA will be repaired by a set of DNA repair enzymes that have become active due to the presence of their substrates, damaged DNA.

Activate the Enzyme-Substrate Complex

In another example taken from UV radiation photobiology, the photoreactive enzyme (DNA photolyase) recognizes one type of DNA damage as its substrate, i.e., the cyclobutane-type pyrimidine dimer, and combines with these dimers in the dark. Activation occurs when the enzyme-substrate complex becomes exposed to visible light, the energy of the light being then used by the enzyme to split the dimer to yield repaired DNA.

Activate the Enzyme Directly

This is generally accomplished by stimulating a conformational change in the enzyme molecule itself or in an attached photochromic inhibitor of the enzyme. There are many examples of each of these mechanisms (7-9).

Induce the Synthesis of the Enzyme

This would occur by gene activation. For example, when bacteria are UV irradiated, a whole group of DNA repair enzymes are induced. Some of these induced enzymes are not present in detectable concentrations prior to induction, while other enzymes are present in small amounts but are induced to higher amounts by UV irradiation. Laser radiation at 633 nm has been shown to stimulate collagen synthesis in cutaneous wounds by enhancing the synthesis of Type 1 and Type II procollagen mRNA levels (10).

Therefore, the light activation of enzyme can occur by several diverse mechanisms. The first two mechanisms mentioned, i.e., the radiation-triggered production of the substrate, and the irradiation of the enzyme-substrate complex do not result in amplification of the bioresponse since one absorbed photon is needed for each photochemical event to take place. For that reason, a high level of radiation is required for these events.

The last two mechanisms, i.e., the direct activation of an enzyme and the induction of the synthesis an enzyme, result in more chemical changes than the number of photons absorbed, and are produced by lower levels of radiation than the two processes mentioned above. Therefore, these last two mechanisms of enzyme activation are strong candidates for the photobiological basis of low level laser radiation therapy in the visible region of the spectrum.

The absorption of radiation in the infrared region results in molecular rotations (rotation of the whole molecule about some axis) and molecular vibrations (the stretching or bending of bonds resulting in the displacement of atomic nuclei relative to each molecule, but not affecting the equilibrium positions of nuclei). Thus, infrared radiation would not be expected to cause chemical changes in molecules, although reaction rates might be increased due to heating.

If the biological effect of low level visible light therapy is through photochemistry (probably the photoactivation of enzymes), and the biological effect of infrared radiation is through molecular rotations and vibrations, how can light-based radiation therapy produce similar clinical responses when either visible radiation or infrared radiation is used? For example, Abergel and coworkers (12, 13) found that the irradiation of fibroblasts in culture either at 633 nm or at 904 nm stimulated the synthesis of collagen. In separate studies, both 633 nm radiation (14) and 1060 nm radiation (15) were beneficial in reducing the pain of rheumatoid arthritis.

To explain the biostimulation effect of low level radiation at 633 nm; Karu (1) proposed a chain of molecular events starting with the absorption of light by a photoreceptor, which leads to signal transduction and amplification, and finally results in the photoresponse. In Karu's model, light is absorbed by components of the respiratory chain (i.e. flavine dehydrogenases, cytochromes and cytochrome oxidase), which causes an activation of the respiratory chain and the oxidation of the NAS pool, which leads to changes in the redox status of both the mitochondria and the cytoplasm. This in turn has an effect on membrane permeability/transport, with changes in the Na'/H' ratio and increases in Na'/K'-ATPase activity, which has an effect on the Ca++ flux. The Ca++ flux affects levels of cyclic nucleotides, which modulates DNA and RNA synthesis, modulating cell proliferation (i.e. biostimulation).

This also suggests an explanation for why radiation at 904 nm can produce biological effects similar to those produced by radiation at 633 nm. In Karu's model, radiation at 633 nm initiates, probably by photoactivating enzymes in the mitochondria, a cascade of molecular events leading to the photoresponse. Radiation at 904 nm produces the same final response, but initiates the response at the membrane level (probably through photophysical effects on Ca++ channels) at about halfway through the total cascade of molecular events that leads to biostimulation.

Calcium ions are intracellular messengers in many signal-transducing systems. The intracellular levels of Ca++ are advantageously kept low because phosphate esters are prevalent and calcium phosphates are very insoluble. The cytosolic level of Ca++ in unexcited cells is several orders of magnitude less than the extracellular concentration. Thus, the cytosolic Ca++ concentration can be abruptly raised for signaling purposes by transiently opening calcium channels in the plasma membrane or in an intracellular membrane (16-23).

In a recent paper, Karu (1) makes the following statement: "the magnitude of the laser biostimulation effect depends on the physiological state of the cell at the moment of irradiation". This explains why the effect is not always detectable, as well as the variability of the results reported in the literature.

For example, it has been established that irradiation accelerated the proliferation of slowly growing HeLa sub-populations. In medicine, laser treatment appears to work in cases of severe damage (e.g. trophic ulcers), and the effect of light on normally regenerating wounds may be insignificant (if there is any). Light only stimulates cell proliferation if the cells are growing poorly at the time of the irradiation. Thus, if a cell is fully functional, there is nothing for laser radiation to stimulate, and no therapeutic benefit will be observed. A similar analogy is that patients will not show a beneficial effect of vitamin therapy if they already receive an adequate supply of vitamins in their daily diets.

The interaction between living tissue and cells and radiations has been extensively studied. Non-limiting examples of such studies are found in references 1-60, A1-A7 and B1-B7.

The following text proposes a number of mechanisms through which the claimed invention achieves desired effects. However, some embodiments of the invention achieve the desired effect through alternative mechanisms. Accordingly, the proposed mechanisms should not be interpreted to restrict the scope of the appended claims that do not claim such mechanisms.

In a first aspect, the claimed invention includes a method for treating a mammalian tissue, such as for example a mammalian skin tissue, the method including irradiating the tissue with radiation defining a pulse train including a plurality of radiation pulses. The radiation has a wavelength of from about 400 nanometers to about 1500 nanometers, the pulses each have a duration of from about 1 femtosecond to about 1 hour, the pulses are separated from each other by an inter-pulse interval, the inter-pulse interval being of from about 1 microsecond to about 10 seconds, and the power density of each pulse in the tissue is of from about 0.1 mw/cm$^2$ to about 10 W/cm$^2$. All the parameters describing the radiation are either adjusted independently from each other or adjusted in combinations causing synergetic effects within the tissue.

The exact values for the various pulse parameters depend on the effect that is sought. Examples of more specific values and of effects that are sought are given hereinbelow.

In one of these examples, the pulses each have a duration of from about 100 microsecond to about 10 milliseconds. In a very specific example of implementation, the pulses each have a duration of from about 250 microsecond to about 1 millisecond.

In another of these examples, the inter-pulse interval is of from about 10 microseconds to about 10 milliseconds. In a very specific example of implementation, the inter-pulse is of from about 100 microseconds to about 500 microseconds.

While the pulse duration and the inter-pulse intervals may be considered separately from each other, it is also within the scope of the invention to consider synergetic effects related to these two parameters.

For example, the ratio of the pulse duration divided by the pulse interval takes any suitable value. In a specific example of implementation, the ratio of the pulse duration divided by the pulse interval is within the interval of from about 0.1 to about 10. In a very specific example of implementation, the ratio of the pulse duration divided by the pulse interval is within the interval of from about 0.5 to about 2. Within this last interval, and non-limitatively, a ratio of the pulse duration divided by the pulse interval of about 1 has been found to produce desired effects in the skin while being technologically achievable.

A specific example of a suitable power density of each pulse in the tissue is a power density contained within the interval of from about 30 mW/cm$^2$ to about 100 mW/cm$^2$.

In a specific example of implementation, the method includes irradiating the tissue with radiation defining a plurality of pulse trains, each pulse train including a plurality of radiation pulses. For example, each pulse train includes from 2 to 100 pulses. The pulse trains are separated by inter-train time intervals wherein no pulses are produced, the inter-train intervals lasting from about 1 microsecond to about 1 second.

The term pulse is to be broadly interpreted. For example, the pulses need not be of a substantially uniform power density with a substantially total absence of power density within the inter-pulse intervals, even if such pulses are an example of pulses suitable for use in some embodiments of the invention.

Indeed, each pulse may present a time evolution leading to pulses having any suitable time evolution. Also, during the inter-pulse interval, the power density is substantially smaller than a power density within each pulse, but not necessarily zero. Examples of such power density during the inter-pulse intervals are given hereinbelow.

In a non-limiting specific example of implementation, the inter-train intervals last from about 500 microseconds to about 2.25 milliseconds and each pulse train includes from 4 to 10 pulses. The ratio of the inter-train interval to the inter-pulse interval is of from about 2 to about 10, and in a very specific example of implementation, the ratio of the inter-train interval to the inter-pulse interval is of about 3.

As described in further details hereinbelow, the above-described method for treating a mammalian tissue finds applications, among other applications, to the production of desired effects in a mammalian skin tissue. For example, the radiation power density temporal profile causes a predetermined physiological change in a mammalian skin tissue.

In the context of this specific example, it has been found that it is beneficial to pulse treat the skin, i.e. it is valuable that the light source is not energized for the whole duration (continuous wave) of the treatment but is rather pulsed, leaving time for the skin to rest between pulses and intervals. Furthermore, it has been found that it is often necessary to stop the pulsing sequence for a greater amount of time after a predetermined number of light pulses have already been emitted.

In one example, the radiation is produced using Light Emitting Diodes (LEDs) which obey a predetermined duty cycle. Of course, should LEDs not necessitating a predetermined duty cycle be used, many constraints regarding the irradiation are removed.

In addition, it has been found that a specific example of a desired physiological effect, namely an increase in collagen production, is favoured by pulsed radiation such as the pulsed radiation described hereinabove. This beneficial effect of pulsed radiation is also present in many other situations.

More specifically, in the context of increase in collagen production, it has been found that the exposure duration ("time on") is a factor to be relatively closely monitored, but that the component of the sequential pulsing of the present invention is the pulse relaxation time or pulse interval ("time off"). Shorter pulse intervals seem to improve the metabolic pathways resulting in healthier skin cells. Then, after a predetermined number of pulses within the pulse train, it is advantageous in some tissues to provide a downtime to let the light skin rest. This downtime is provided by the inter-train interval.

Target response selectivity is made possible not only by picking the appropriate pulse durations, but also by picking the proper inter-pulse interval assuming that all other established parameters are held constant (fluence, irradiance, treatment time, wavelength, spot size, working distance, etc.). In a specific and non-limiting example of implementation, the target within which a response is sought includes a chromophore, but alternative targets are within the scope of the invention.

In the context of increased collagen production, the pulse train typically includes more than three pulses of substantially equal pulse duration, separated by substantially equal inter-pulse intervals wherein substantially no power is provided within the tissue. Each pulse train is separated from a subsequent pulse train by the inter-pulse interval.

More specifically, and non-limitatively, it has been found interesting to use three or more pulses of 250-1000 μsec (microseconds) by pulse trains separated by 100-500 μsec intervals. Pulse train intervals of suitable durations are used to separate pulse trains, as dictated by the duty cycle of the LEDs used and physiological parameters, both at the cellular and at the molecular level.

While in many embodiments of the invention the pulse durations, inter-pulse intervals, number of pulses within each pulse train and inter-train intervals are substantially constant within each treatment, it is within the scope of the invention to have treatments wherein these parameters are not constant over the whole treatment.

The number of pulses to be administered during a session depends on many parameters such as the power density desired, the energy density delivered by the LEDs or other light source used, the wavelength, and the spot size, for example. As will be apparent to one skilled in the art, the number of pulses by pulse train is variable and depends on the exact effect that is sought.

It has also been found that pulsed radiation similar to the pulsed radiation described hereinabove is usable to treat other skin conditions that are not related to collagen production. For example, it appears possible to treat cheloids by photo-inhibition and atrophic scars through photoactivation. It is also believed possible to treat acne, eczema, psoriasis, vitiligo, rosacea, hair regrowth, exogenous pigments, dermal melanosis, some adnexial tumors and cutaneous hyperpigmentation via the proposed method. Therefore, the above-described irradiation of the skin is usable for many dermatological conditions. A proposed and non-limiting mechanism through which these treatments may work includes modulating a skin cell activity.

In addition, using pulsed radiation defined by suitable pulse and radiation parameters leads to a stimulation of collagen production that is substantially larger than a collagen production produces by a continuous mode stimulation. A proposed, non-limiting, and non-binding, mechanism that may cause this effect includes a reduction in cellular exhaustion and provides optimal dermal fibroblast stimulation as well as collagenase inhibition.

The above-described method for treating a mammalian skin tissue and results obtained therefrom also suggest a method for altering the physiology of a mammalian tissue, the method including irradiating the tissue with radiation defining a suitable radiation power density profile. The radiation power density profile is any suitable power density temporal profile, such as, non-limitatively, a power density temporal profile including a plurality of pulse trains, each pulse train including a plurality of radiation pulses having a predetermined pulse width and being separated from each other by an inter-pulse time interval, the pulse trains being separated from each other by an inter-train time interval, the inter-train interval being substantially larger than the inter-pulse interval.

Examples of suitable values for ratio of the inter-train interval to the inter-pulse interval and the number of pulses within each pulse train have been mentioned hereinabove.

In an example of implementation, a minimal power density of the radiation within the tissue during each pulse is at least about two times as large as a maximal power density of the radiation within the tissue during each inter-pulse interval. In another example, a minimal power density of the radiation within the tissue during each pulse is at least about ten times as large as a maximal power density of the radiation within the tissue during each inter-pulse interval. In yet other examples of implementation, a minimal power density of the radiation within the tissue during each pulse is at least about 100 times or at least about 10000 times as large as a maximal power density of the radiation within the tissue during each inter-pulse interval. Suitable values of pulse duration, power density of each pulse in the tissue, ratio of the pulse duration divided by the pulse interval have also been mentioned hereinabove.

The above-described irradiations also find applications in causing a predetermined physiological change in a mammalian tissue, the tissue being irradiated with a radiation having a power density in the tissue substantially larger than an activation threshold power density, the tissue being irradiated under conditions suitable to cause the predetermined physiological change.

In an embodiment, the activation threshold power density is a power density: below which the predetermined physiological change is substantially absent from the mammalian tissue upon the mammalian tissue being irradiated with the radiation and above which the predetermined physiological change is substantially present in the mammalian tissue upon the mammalian tissue being irradiated with the radiation.

However in alternative embodiments of the invention, an activation threshold is relatively hard to define as the presence of the predetermined physiological change is progressively observed as a function of the power density. In these cases, the activation threshold is a power density above which the predetermined physiological change is observed in the tissue at a level that is large enough to be clinically significant.

In an embodiment of the invention, the power density is below a thermal threshold power density over which a temperature of the irradiated tissue increases to temperature greater that a predetermined overheating temperature. Over the predetermined overheating temperature, the predetermined physiological change is substantially inhibited at least in part, substantially totally inhibited or even substantially reversed.

The definition of a thermal threshold is a consequence, among other factors, of a thermal inertia of the irradiated tissue. Indeed, the irradiated tissue has a thermal diffusion coefficient and a heat capacity that buffer an increase in temperature upon deposition of heat within the tissue.

To achieve a relatively high power density (or intensity), within the limits of a non-thermal treatment, there is a need to generate a relatively high intensity over a relatively short treatment time. Then, the thermal inertia and thermal conduction coefficient of the tissue achieve a relatively high power density without causing a potentially harmful temperature increase in the tissue.

The suggested non-thermal light-based treatment described hereinabove is a therapeutic strategy established with the specific concern that supra-physiologically, a temperature rise potentially reduces or impedes the normal metabolism within the tissue. For example, in mammalian skin tissue, such supra-physiological temperature rises potentially reduce or impede collagen metabolism and potentially promote collagen degradation.

Aside the fact that triple helices of type I collagen melt just several degrees above body temperature (B1, B2), a thermal treatment where a skin temperature increase (for example, superior by 2° C. to the maximal non-pathological temperature of the skin) is maintained, being repeated or not, can enhance the production of collagen degrading-enzymes, collagenases (such as metalloproteinases (MMP)).

If the temperature of the tissue increases sufficiently, a heat shock induces the expression of MMP-1 at the mRNA and protein levels in a temperature-dependent manner (B3). Also, it was found that heat treatment increases MMP-12 mRNA and protein expression in human skin (B4). MMP can trigger dermal collagen degradation to reverse collagen metabolism. Evidence points out that proteolytic enzymes like MMP-1/MMP-2 would add to and already poorer collagen production by degrading collagen at the pace it is newly produced (B5). Moreover, occurring fragmentation of type 1 collagen by collagenases would act as to promote collagen loss both in aged and photodamaged skin, as the damaged protein would down-regulate collagen synthesis by cells naturally able to produce collagen (B6, B7).

In addition, skin hyperthermia has a potential to promote an inflammatory state with increased redness (rubor), heat (calor), swelling (tumor), and pain (dolor). The redness and heat are caused by the increased blood supply to the heated area. Blood vessels and capillaries become vasodilated providing extravasation of various leukocytes involved in the initiation and maintenance of inflammation. It is preferable to substantially minimize these side effects.

Finally, enzymatic activity would be challenged by supra-physiological temperature at the treatment site. Heat sets off protein denaturation, which implies lost of enzymatic function. Collagen synthesis would be compromised with a potential risk of fibrosis. Furthermore, high intensity, or high power density, light sources result in the deoxygenation of tissue and possible hyperthermia.

In an example wherein the tissue is a skin tissue, a relatively high power density brings the targeted tissue to its physiological threshold of activation and triggers a cascade of events leading, for example, to enhanced procollagen production. However, these beneficial effects are cancelled and even reversed if the skin reaches the overheating temperature.

Non-thermal reactions initiate molecular conformational changes and metabolic activation relatively quickly. A suitable fluence (dose or quantity of energy reaching the skin) is delivered, in a relatively short treatment time without any substantial increase in the skin temperature.

In this case, power density and fluence become independent variables. Indeed, there is a need to achieve the power density activation threshold independently of the required total fluence. Only a relatively high power density can provide such high fluence with substantially no heat being delivered to the skin. As already mentioned, the condition of a relatively small increase in skin temperature is advantageous as supra-physiological skin surface temperature has a potential to prevent proper photobiochemical reactions from happening.

In a specific embodiment of the invention, the power density required for cellular activation is between 30 and 100 mW/cm$^2$ at tissue. Since the intensity for a suitable activation of fibroblasts within the skin tissue is relatively sensible to the power density, there is a need for a relatively accurate method of delivering the radiation into the tissue. In a specific example of implementation, a novel optical positioning system, described elsewhere in this document, is used to provide a relatively very precise working distance between the light source and the surface of the skin for optimal beam intensity delivery. However, it is within the scope of the invention to irradiate the tissue using any alternative suitable apparatus.

Prolonged but insufficient power density irradiation will have substantially no physiological benefit since the power density activation threshold is not surpassed. In addition, as described in further details hereinbelow, pulsing patterns must be elaborated to minimize cellular exhaustion.

As also further detailed hereinbelow, no adverse effects have so far been linked to the above-described method, especially in an embodiment of the invention wherein the radiation is produced by Light Emitting Diodes (LEDs). This is probably due to a substantial absence of thermal damage during treatment. Any other suitable interval of power density may be used, depending on the exact tissue and duration of irradiation.

In alternative embodiments of the invention, the activation threshold is about 0.1 mW/cm$^2$. In other alternative embodiments of the invention, the activation threshold is about 10 mW/cm$^2$. In yet other alternative embodiments of the invention, the activation threshold is about 30 mW/cm$^2$.

Also, in alternative embodiments of the invention, the thermal threshold is about 10 mW/cm$^2$, about 100 mW/cm$^2$, about 1 W/cm$^2$, and/or about 1 kW/cm$^2$. The thermal threshold is linked to both the thermal inertia of the tissue and to the power density temporal pattern of the radiation, among other factors.

In a specific embodiment of the invention, the activation threshold power density is about 30 mW/cm$^2$ and the thermal threshold power density is about 100 mW/cm$^2$.

In one embodiment, the overheating temperature is about 2° Celsius over a maximal non-pathological in-vivo temperature of the mammalian tissue. In other embodiments of the invention, the overheating temperature is about 0.5° Celsius over a maximal non-pathological in-vivo temperature of the mammalian tissue. In yet other embodiments of the invention, the overheating temperature is about 0.1° Celsius over a maximal non-pathological in-vivo temperature of the mammalian tissue.

The exact overheating temperature depends on many factors. For example, the overheating temperature depends of a balance between beneficial effects of the radiation and harmful effects of the radiation. Control of the temperature of the skin is achieved at least in part through a suitable temporal pattern of power density. Another manner of controlling skin temperature includes cooling the skin, for example through convection. Another manner of cooling the skin includes vasodilatating the skin blood vessels, for example through the administration of a suitable vasodilatating substance.

The embodiments focus mainly on applications to mammalian skin tissue. However, in alternative embodiments application can be performed on any other suitable tissue.

Also, other parameters of the radiation must be suitably adjusted to achieve an expected photoresponse. For example, the fluence (for example in J/cm$^2$) or total dose of energy released over a definite amount of time is such a parameter. Fluence and power density are independent variables which ought to be considered, especially for medical applications. For instance, bearing in mind equal fluence delivered, irradiance values under the threshold point, even under prolonged irradiation time, would very likely produce minimal results in biostimulatory effects. Consequently, an accurate working distance is required so as to provide the needed irradiance to ensure successful collagen production by targeted dermal fibroblasts.

As mentioned hereinabove, the physiological effect includes for example stimulating collagen production by fibroblasts contained within the skin tissue. In another example, the physiological effect includes reversing skin damages caused by aging, for example by reversing damages caused to an extracellular matrix of the skin by aging. Yet another physiological effect includes modulating an apoptosis response of the skin tissue.

In another aspect of the invention, the above-described radiation temporal power density profile is suitable to provide a method for altering the physiology of a mammalian tissue. More specifically, this method includes irradiating the tissue with a time-varying radiation according to a temporal power density profile suitable for both activating molecular cascades of events and activating cells contained within the tissue.

In specific embodiments of the invention, the power density temporal profile of the radiation is selected so that at least one of the following effects are produced:

initiating molecular-scale events within the tissue leading to the desired physiological effect;

stimulating cell-scale events within the cells of the tissue;

allowing a cellular relaxation so as to prevent cell exhaustion during the irradiation;

allowing a molecular relaxation so as to allow reversible molecular conformational changes to be reversed;

preventing a temperature increase in the tissue above a thermal threshold at which a cascade of events triggered by radiation and leading to the desired alteration of the physiology of a mammalian tissue is reversed; and/or preventing a temperature increase in the tissue above a thermal threshold above which tissue damage occurs.

In other embodiments of the invention, the power density temporal profile of the radiation is selected so that two or more of the above-mentioned effects occur. The reader skilled in the art will readily appreciate that a suitable choice of radiation, including a suitable chaise of radiation power density temporal profile leads to potentially synergetic effects.

In a specific embodiment of the invention, cell-scale events include progressively increasing a mitochondrial activity level within the cells of the tissue while the resting periods substantially prevent cell exhaustion.

An example of a tissue wherein the above-described effects has been observed to occur is a skin tissue wherein the irradiation stimulates collagen production by fibroblasts. However, it is within the scope of the invention to apply radiation to achieve a desired physiological effect in any other suitable tissue. Also, it is within the scope of the invention to irradiate both in vivo tissue and in vitro tissues.

In a specific example relating to skin tissue, experimental results suggest that to successfully enhance dermal collagen production leading to clinically significant results, a combination of the following achieves a suitable activation of dermal fibroblasts by non-thermal, non-coherent LED light.

A sequential pulsing mode with predetermined time on and time off provides resting periods during irradiation of dermal fibroblasts. While preventing cell exhaustion, this pulsing mode contributes to energize the metabolic pathways for optimal signal transduction and amplification.

Pulse duration of between about 250 and about 1000 µsec have been shown to produce interesting results, but other pulse durations are within the scope of the invention. It is hypothesized that such pulse durations meet the necessary time for the antenna molecule to initiate the molecular cascade of events probably taking place within the mitochondria and leading to the cell response. This molecular cascade of events is initiated further to an antenna molecule receiving at least one photon contained within the radiation and likely occurs in the mitochondria of cells of the tissue.

Pulse intervals of about 100 to about 500 µsec have also been shown to produce suitable effects. This order of magnitude of pulse intervals substantially enhances molecular photobiochemical reactions within the mitochondria as it provides resting phases between pulses in order to achieve reversible molecular conformational changes that will ultimately generate signal transduction and amplification leading to an expected gene expression.

Regarding the pulse trains, they each include from 4 to 10 pulses in this example. The number of pulse needed to bring the cell to the needed level of activation within the pulse train seems to be an important parameter. For values larger than 10, the cell probably sees the pulse trains as a quasi-continuous-wave modes and little or no further stimulatory effects are triggered in this particular example.

Pulse train intervals of about 750 µsec to about 2250 µsec are suitable. In a specific example, the inter-pulse interval is at least 3 times the pulse duration. This relatively long lag time between pulse trains seems to have an effect in preventing cell exhaustion through avoidance of mitochondrial depletion that brings the cell to a higher level of gene expression.

The number of pulses within each pulse train is large enough to bring the cells to a suitable level of activation while preventing the cell to each a steady-state of activation.

Another observed effect of pulse trains similar to the above-described pulse trains is a regeneration of an extracellular matrix in mammalian tissue. To that effect, the tissue is irradiated with radiation under conditions suitable to regenerate the extracellular matrix. For example, the tissue is a skin tissue.

In this case, it has been observed that a suitable radiation leads to an at least partial reversal of the effects of aging within the skin tissue. Various mechanisms whereby this reversal is effected include a stimulation in collagen production within the tissue, a stimulation of collagen repair within the extracellular matrix, a downregulation of a matrix metalloproteinase (MMP) gene expression within the cells of the tissue, an upregulation of procollagen production within the cells of the tissue, a reduction in elastin degradation within the extracellular matrix and a reduction fibronectin degradation within the extracellular matrix, among others.

Indeed, a suitable radiation seems to restores extracellular matrix (ECM) equilibrium in the dermis. In aging skin, collagen production decreases while degradation increases. External signs of aging such as uneven pigmentation and wrinkles, thinning skin, lack of firmness and dullness result from a reduction in collagen, a protein that gives the skin its suppleness as well as its ability to repair itself.

Free radicals are known to attack the collagen. As collagen diminishes, the skin's ability to regenerate and heal itself declines. Normally, healthy collagen gives the skin its softness and resiliency. But damaged collagen molecules become stiff and inflexible, making the skin appear old. Besides collagen, other dermal extracellular matrix components like elastin become altered and damaged. Hence the term elastosis describes age and sun related histopathological morphological alterations in the upper dermis.

Free radicals can also stimulate production in the body of collagen-digesting enzymes. When the skin is exposed to ultraviolet light, free radicals activate transcription factors, chemical messenger molecules normally present in the cells.

When activated, the transcription factors migrate to the nucleus of the cell and stimulate DNA to produce collagen-digesting enzymes. These begin to leave tiny defects in the skin, which eventually turn into wrinkles.

Lastly, free radicals also cause inflammation. This occurs at the cellular level and is not visible to the naked eye. Inflammation can happen in a number of ways. It can be the result of the oxidation of enzymes produced as a defense mechanism by the body in response to exposure to trauma such as sunlight or chemicals. Anti-inflammatory effects of suitable irradiation, such as irradiations defined by above-discussed parameters, counteract such skin damage.

In addition, matrix metalloproteinase (MMP) activity is highly regulated in skin tissue. It plays a key role in dermal extracellular matrix turnover. MMPs are a large family of proteolytic enzymes, which are involved in the degradation of many different components of the extracellular matrix. The MMPs have been classified into different groups including collagenases, gelatinases, stromelysins, and others. There is increasing evidence indicating that individual MMPs have important roles in aging skin.

While the above suggests that completely stopping collagen degradation would provide an ideal treatment against aging, controlled degradation of extracellular matrix (ECM) is in fact essential for the homeostasis of the dermis. However, recent evidence suggests that this homeostasis is out of balance in aging and photoaged skin. Downregulation of MMP gene expression combined with upregulation of procollagen production are therefore two components that may lead a successful anti-aging photoinduction.

More specifically, as described in more details in the examples found hereinbelow, the role of MMP-1 or collagen degrading enzyme using a non-ablative non-thermal LED therapy has been thoroughly studied since most dermal extracellular matrix is composed of collagen.

In addition, new research indicates that another matrix metalloproteinase (MMP), MMP-2, is a strong marker for other dermal matrix degrading enzyme activity. MMP-2 or Gelatinase-A is able to degrade elastin, fibronectin, type IV collagen, and gelatins but shows no activity against laminin or interstitial collagens. Also, these enzymes are thought to act co-operatively with the collagenases to effect the complete degradation of interstitial collagens. Gelatinase-A is widely expressed in adult tissues and constitutively expressed in many connective tissue cells with poor regulation by growth factors (GF).

Induction of MMP expression by agonists requires transduction of a signal from the extracellular space to the MMP genes. This is achieved by agonist binding to cell membrane receptors, and in some cases cytoplasmic receptors, activation of cellular tyrosine kinase signal transduction cascades, transcription factor activation and induction of MMP transcription. Conversely, downregulation of MMP gene expression that may be trig erred, for example using the above described tissue irradiation, has a potential to lead to aging reversal in skin tissue.

The above-described irradiation may also be approached as leading to a method for improving cellular integrity in mammalian tissue, the method comprising irradiating the tissue with radiation under conditions suitable to improve cellular integrity in the mammalian tissue. For example, the method comprises stimulating collagen production within the skin tissue.

Briefly, non-coherent, non-thermal visible/near infrared light was observed to restore cellular integrity of aged and photoaged fibroblasts, regaining their full potential and basal metabolic collagen secretion level. A goal of such a therapy is to reverse the constantly declining collagen production level over the years and increase it towards a basal level by using a predetermined number of radiation treatments over a period of time.

More specifically, the claimed invention includes a method wherein a tissue is irradiated over a plurality of treatments and the treatments are provided with an inter-treatment time interval therebetween. Further, within each treatment, the power density temporal profile during the treatment defines a plurality of pulse trains, each pulse train including a plurality of radiation pulses having a predetermined pulse duration and being separated from each other by an inter-pulse time interval. The pulse trains being separated from each other by an inter-train time interval, the inter-train interval being substantially larger than the inter-pulse interval and the irradiation is performed under conditions suitable for substantially reducing damages previously caused to a mammalian skin tissue.

In a specific example the treatments are applied within a rejuvenating phase wherein the tissue is substantially rejuvenated. Optionally, the treatments are further applied during a maintenance phase following the rejuvenating phase, the maintenance phase including treatments that substantially maintain the rejuvenation of the tissue.

In some embodiments of the invention, the inter-treatment time interval during the maintenance phase is substantially larger than the inter-treatment time interval during the rejuvenating phase. Some of these latter embodiments are such that the inter-treatment time interval during the maintenance phase is substantially larger than the duration of the rejuvenating phase.

The inter-treatment time intervals are adjusted in any suitable manner. For example, the inter-treatment time interval during the rejuvenating phase is from about 1 minute to about 1 year. In other examples, the inter-treatment time interval during the rejuvenating phase is from about 1 hour to about 1 month. In yet other examples, the inter-treatment time interval during the rejuvenating phase is from about 1 day to about 1 week. In yet other examples, the inter-treatment time interval during the rejuvenating phase is from about 3 days to about 4 days.

The inter-treatment time interval during the maintenance phase is also adjusted in any suitable manner and is, for example and non-limitatively, from about 1 day to about 5 years. In other examples, the inter-treatment time interval during the maintenance phase is from about 1 month to about 1 year. In yet other examples, the inter-treatment time interval during the maintenance phase is about 1 year.

In some specific embodiments of the invention, the rejuvenating phase includes from 5 to 20 treatments with an inter-treatment time interval during the rejuvenating phase of from about 1 day to about 1 week. In this example, a suitable example of an inter-treatment time interval during the maintenance phase is from about 1 month to about 1 year. Maximizing the inter-treatment interval during the maintenance phase while maintaining the treatment efficiency is advantageous to a patient undergoing the treatment.

Embodiments of the rejuvenating phase include from 2 to 1000 treatments, 2 to 50 treatments, and 5 to 20 treatments. In a specific embodiment of the invention, a rejuvenating phase including 12 treatments has been shown to give acceptable results.

For each treatment, the radiation is provided according to a power density temporal profile similar to the above-described power density temporal profiles. Another parameter that also needs to be determined is the total fluence of each treatment. A fluence of 4.5 J/cm$^2$ or greater has been shown to give acceptable results, especially below 10 J/cm$^2$ but other fluences are also within the scope of the invention. For example, the fluence of each treatment can be from about 1 mJ/cm² to about 20 kJ/cm², about 1 J/cm² to about 50 J/cm², and from about 4 J/cm² to about 10 J/cm².

In a specific example, 3 to 50 treatments, each irradiating the tissue with a fluence having a value of from about 1 to about 30 J/cm² are performed over a period of from about 1 day to about 1 year. Afterwards, maintenance therapy is performed to help preserve skin appearance. In a very specific example of implementation, between 4 and 10 J/cm² are deposited in the skin at a rate of two treatments per week for six week. Afterward, a single similar annual treatment helps in conserving the improvements caused to the skin.

A possible mechanism for this action follows from Karu (1) who stated that the magnitude of the laser biostimulation effect depends on the physiological condition of the cell at the moment of irradiation. Light would only stimulate cell proliferation if the cells are growing poorly at the time of the irradiation. Cell conditions are to be considered since laser/light exposures would restore and stimulate procollagen production, energizing the cell to its own maximal biological potential.

Therefore, a suitable irradiation therapy regenerates at least in part cellular integrity of aged and photoaged fibroblasts, enabling them to eventually regain their full potential and basal metabolic collagen secretion level, or at least to improve these factors. The goal of such therapy is to reverse at least in part the constantly declining collagen production level over the years and bring it back to basal level by using a predetermined number of treatments over a relatively short period of time. Maintenance therapy is then the key to keep the best overall skin appearance.

More generally, the invention provides a method for reducing damages previously caused to a mammalian skin tissue, the method comprising irradiating the tissue with radiation presenting a temporal power density profile such that the radiation has a power density within the tissue that is above an activation threshold at least over a predetermined time interval, the predetermined time interval being such that the radiation causes an increase in temperature within the tissue of at most 20 Celsius.

In a specific example of implementation, the radiation presents a temporal power density profile substantially preventing a cellular exhaustion, the cellular exhaustion being a state of the cells wherein the cells are unable to respond to further irradiation. More specifically, the radiation presents a temporal power density profile substantially preventing mitochondrial exhaustion.

In some embodiments of the invention, the temporal power density profile of the radiation stimulates the skin tissue so as to repair damages to the extracellular matrix of the skin tissue. For example, the mammalian skin tissue is human skin tissue.

Examples of damages previously caused to a mammalian skin tissue include a degradation of extracellular collagen, a degradation of extracellular elastin, a degradation of extracellular fibronectin and a reduction in collagen secretion by fibroblasts contained within the skin tissue, among others.

In yet another aspect of the invention, non-thermal, non-coherent close/near Infrared (IR) light therapy is effective against apoptosis. Indeed, a substantially rejuvenated tissue includes cells that are less likely to experience apoptosis than the cells were prior to the irradiation. The diminution in the likelihood of apoptosis is caused at least in part by a reversal of an aging process or at least in part by a reversal of damages caused by environmental factors.

With regards to the an application of the invention to reversal of aging, it is known that aging of the skin shifts the balance between collagen production and breakdown, which leads to wrinkles, facial sag and rough skin texture. Stimulating skin cells to produce collagen can partly reverse this process. Stimulating collagen synthesis in aged skin was shown to reduce wrinkles and improve skin texture. The benefit of stimulating a person's own collagen production is that collagen is deposited in an orderly, structured manner and that there is no risk of allergy, immune reaction or injection-induced infection.

It has been found that it is possible to stimulate the collagen production by subjecting the skin to light in the 635-805 nm (nanometers) range. It has also been found that by using a non-thermal light source, such as for example a Light Emitting Diode (LED), it is possible to minimize the risks of leaving treatment marks. Furthermore, it has been found that light can be shone directly onto the skin without necessity of removing a skin layer, thereby yielding a non-ablative method.

It has also been found that the production of collagen is a natural photobiochemical reaction similar to plant photosynthesis. To maximize benefits of LED therapy on skin, a topical formulation may optionally be used during treatment, such as a specially formulated topical formulation may be used as an adjunct therapy to promote collagen synthesis with powerful antioxidants to inactivate free radicals including vitamins (A, $B_5$, C, E) and essential nutrients.

Thirdly, it has also been found that it is beneficial to pulse treat the skin, i.e. it is valuable that the light source is not energized for the whole duration (continuous wave) of the treatment but is rather pulsed, leaving time for the skin to rest between pulse and intervals. Furthermore, it has been found that it is often necessary to stop the pulsing sequence for a greater amount of time after a predetermined number of light pulses have already been emitted. Indeed, as will be obvious to one skilled in the art, LEDs must obey a predetermined duty cycle. Of course, should LEDs not necessitating a predetermined duty cycle be used, the train of pulses could be repetitive, as will be described hereinbelow.

It has also been found that the sequential pulsing mode described hereinabove may be used to treat other skin conditions that are not related to collagen production. For example, it appears possible to treat cheloids by photoinhibition and atrophic scars through photoactivation. It is also believed possible to treat acne, eczema, psoriasis, vitiligo, rosacea, hair regrowth, exogenous pigments, dermal melanosis, some adnexial tumors and cutaneous hyperpigmentation via the proposed method. It is therefore believed that the Sequential Pulsing Mode according to the present invention, by turning skin cells on and off and its effects on the skin may be used for many dermatologic conditions.

Even though wavelength is an important parameter in irradiation of tissues, it is less specific to activate the fibroblast. Several known absorption peaks can activate the fibroblast. 660 nm wavelength is one of the peak absorption spectrum of the fibroblast (49).

The present invention also relates to a non-ablative, non-thermal method for the treatment of skin by photoactivation of procollagen and/or photoinhibition of collagenase (such as MMP-1). The method involves projecting photoinduction light having predetermined photoinduction light parameters on a target treatment area of the skin and, hence, using photons to trigger photobiochemical reactions within the skin.

Typically, the photoinduction light has wavelength values between 600 and 700 nm, for example with a peak at 660 nm. Indeed, reported evidence shows that normal and abnormal human fibroblast cell lines exhibit higher cell counts when exposed to a 660 nm light source. The 660 nm wavelength is also associated with photosynthesis in plants wherein the latter use chlorophyll to convert sun light into cellular building blocks. Furthermore, 660 nm provides a relatively optical penetration into the skin. The increased depth of penetration of higher wavelengths provides differences in specific protein expression and greater proliferating capacity by dermopapillary vs. deeper reticular fibroblast. In human skin, a penetration depth at 660 nm is 2.23 mm, enough to reach the dermis.

It should, however, be understood that other wavelengths could be used for overall increased collagen synthesis or other applications without departing from the scope of the present invention.

In some embodiments of the invention, the above-described irradiations are performed using a suitable laser-based device. However, LED light therapy is an effective alternative to lasers. LEDs are available in multiple wavelengths, can be arranged in large, flat arrays (allowing treatment of large areas) and produce no thermal effects (no pain and virtually no side effects for the patient). Furthermore, LED therapy is considered low risk therapy by the FDA as opposed to laser therapy that can actually damage the eye with their pinpoint beam of laser light (15).

EXAMPLE 1

This example describes in further details an the use of an innovative non-ablative, non-thermal LED system for skin rejuvenation in an in vitro model using human reconstructed skin.

Benefits associated with the enhancement of homologous collagen production with a light source for the treatment of aging skin in healthy patients involve the stimulation of specific subcellular photoreceptors located in the mitochondria of mammalian cells like dermal fibroblasts. The mitochondrial target or antenna molecule seems to be the last enzyme of the respiratory chain, the cytochrome c oxidase. Medical literature covering the use of light to activate dermal fibroblast collagen synthesis remains sparse, although stimulation of the fibroblast would result in a clinically relevant effect. Hence, critical parameters must be considered to boost collagen secretion using pulsed LED light source. For instance, specific wavelengths were suggested to induce increased growth characteristics in fibroblasts. Normal and abnormal human fibroblast cell lines exhibit significantly higher cell counts when exposed to 660 nm wavelengths (A1).

The fluence, or total dose of energy distributed over a given amount of time, is another important characteristic influencing light therapy, as well as irradiance or the total light intensity reaching the cell. In fact, cellular threshold irradiance must be exceeded in order to induce a proper physiological stimulation, in this case, collagen synthesis.

Fluence and irradiance are independent variables to be considered in order to generate a specific physiological effect. Even prolonged but insufficient irradiance exposure will have no physiological benefit since the irradiance threshold is not surpassed. In addition, pulsing patterns must be elaborated to avoid possible cellular exhaustion, implying that required patterns of sequential exposures must be rigorously tested, to allow resting time to fibroblasts in between stimulations, over the entire treatment span. Finally, very precise positioning or working distance is mandatory to assure optimal beam delivery intensity covering the treatment area, so as to achieve maximum physiological effects. Therefore, many variables will influence the success and efficacy of LED therapy.

In vitro testing of pulsed sequence parameters and monitoring of procollagen and MMP-1 secretion on multi-age human primary fibroblasts monolayer and human reconstructed skin are reported hereinbelow. Also, the results are obtained and discussed in the context of seeking an optimization of an innovative non-thermal and relatively powerful pulsed LED light source for skin rejuvenation.

The fibroblast is the major dermis cell type, producing and secreting procollagen and elastic fibers (A2, A3). Procollagen is terminally cleaved by proteolytic enzymes into collagen that aggregates and becomes cross-linked, these tightly cross-linked collagen fibers providing tensile strength and resistance to shear and other mechanical forces.

LED therapy offers an innovative strategy to optimize the capacity of the cell to produce collagen and promote dermal softness, resiliency, suppleness, and increased skin repair ability, while also triggering the basic energy process in mitochondria to activate colour sensitive cytochrome systems playing a central role in the bioenergetics of the cell (12, 32, 54, 50).

Karu (A8) stated that the magnitude of the laser biostimulation effect depends on the physiological condition of the cell at the moment of irradiation. Light would only stimulate cell proliferation if the cells were growing poorly at the time of the irradiation. Cell conditions are to be considered since laser/light exposures would restore and stimulate procollagen production, energizing the cell to its own maximal biological potential. No adverse effect has so far been linked to LED therapy, most probably due to absence of thermal damage during treatment.

An objective of the present study is to evaluate the efficacy of an innovative LED technology on in vitro stimulation of normal human reconstructed skin. Eleven (11) LED exposures of determined sequential pulsing rates were performed over a one-month period on fibroblasts from reconstructed skin from three adult females of 38, 42 and 64 years old (F38, F42, F64).

Procollagen dosages increased while percentages of total activity of matrix metalloproteinase-1 (MMP-1) decreased proportionally. Hence, pulsed LED light exposures seem to significantly reverse photoaging damage while boosting collagen production and reducing collagenase (MMP-1) activity.

The pulsed LED light source tested in this study is an innovative non-ablative non-thermal light source using photons to trigger photobiochemical reactions, stimulating skin collagen. Critical light pulsing parameters impacting on the success of LED therapy have been evaluated and determined during the in vitro development process on human reconstructed skin of this high power density, new light therapy device. Therefore, examples of power density temporal profiles that are suitable to achieve the desired results were determined.

II. Protocol

In Vitro Experiments: Human Fibroblast Monolayer and Human Reconstructed Skin Model Cell culture media. Keratinocytes were grown in complete DME-HAM medium: a combination of Dulbecco-Vogt modification of Eagle's medium (DME) with Ham's F12 in a 3:1 proportion (Gibco), supplemented with 5% Fetal Clone II serum (FCSII) (HyClone, Logan, United States), 10 ng/mL epidermal growth factor (Austral biologicals, San Ramon, United States), 24.3 µg/mL adenin (Sigma), 5 µg/mL insulin (Sigma), 5 µg/mL transferrin (Roche), $2 \times 10^{-9}$ M 3,3'5' tri-iodo-L-thyronin (Sigma), 0.4 µg/mL hydrocortisone (Calbiochem, La Jolla, United States), 100 IU/mL penicillin G (Sigma), and 25 µg/mL gentamycin (Schering, Pointe-Claire, Canada). Fibroblasts were cultured in DME containing 10% fetal calf serum (FCS) (HyClone), 100 IU/mL penicillin G, and 25 µg/mL gentamycin.

Cell isolation. Human epidermal keratinocytes and dermal fibroblasts were isolated from normal skin specimens; keratinocytes are mainly found in the epidermis while fibroblasts are localized in the dermis. Skin specimens were collected from healthy adult females of 38, 42 and 64 years old during either reductive breast surgery (F38, F42) or face-lift (F64). Procedures for cell isolation were initiated within three hours following the surgery according to previously published methods (A5, A6). Briefly, skin specimens were washed five times with a phosphate buffer saline supplemented with 100 IU/ml penicillin G and 25 µg/ml gentamicin. Specimens were then cut in 3 mm wide strips and kept overnight at 4° C. in Hepes buffer containing 500 µg/ml thermolysin. The epidermis was mechanically separated from the dermis with forceps; keratinocytes dissociated from the epidermis though incubation of the epidermal fragments under agitation at 37° C., for 30 minutes, with 0.05% trypsin-0.1% EDTA in PBS. Following trypsin inactivation (addition of culture medium containing 10% serum and centrifugation), keratinocytes were expanded in the presence of irradiated 3T3 fibroblasts in T75 flasks and subsequently frozen until further use. Fibroblasts were dissociated from the remaining dermis fragments following incubation in a collagenase H solution, at 37° C., under agitation. After centrifugation, fibroblasts were also plated in T75 flasks for expansion and subsequently frozen until further use. Three different fibroblast primary cell lines (F34, F42, and F64) and one keratinocyte cell line were used in this study.

Light source. The various light sources tested were supplied by OPUSMED inc. and were gas sterilized prior to handling in the tissue culture laboratory. Herein, three different low energy LED light sources (wavelengths of 635, 660 and 805 nm) and six different sequential pulsing modes, for each light source reaching a total of 18 distinct tested modes were investigated. During this study, total fluence was kept steady at 4 J/cm$^2$. Light intensity or irradiance delivered to the skin was also kept constant at 50 mW/cm$^2$, for a total exposure time of 160 seconds, including various time on and time off sequences (pulsed pattern). Modes A, B and C are also referred-to as modes 1, 4 and 6 hereinbelow.

flasks for four weeks to form sheets. Two fibroblast sheets were then superimposed to form a reconstructed dermal equivalent, after which human epidermal keratinocytes were expanded and seeded on top of the dermal equivalent and cultured for 1 week under submerged conditions. Cultivation of the cell system at the air/liquid interface took place for an additional 4 weeks. Finally, LED treatments were performed over reconstructed skin 3 times a week, for 4 consecutive weeks. Supernatants were collected prior to each treatment and 24 hours after the final treatment. Experiments were done using different normal human reconstructed skin and each test point was performed in triplicate. Determination of procollagen and MMP-1 concentrations in harvested supernatants was respectively assessed with specific ELISA and activity assay systems.

LED Treatment Parameters. From previous initial preliminary results obtained from in vitro tests performed on human primary fibroblasts monolayer (data not shown), eighteen (18) well-responding pulsing LED modes were kept for further testing on complete normal human reconstructed skin (dermis and epidermis). Subsequently, in vitro response regarding procollagen and MMP-1 secretions were evaluated using eleven (11) consecutive LED exposures performed with the best sequential mode A (at a determined pulse sequence already tested and optimized in vitro, over a one-month period, on human reconstructed skin from, among others, three healthy 38, 42 and 64 year old females (F38, F42, F64). Duration of treatment was determined by total fluence.

Cell culture media: Keratinocytes were grown in complete DME-HAM: a combination of Dulbecco-Vogt modification of Eagle's medium (DME) with Ham's F12 in a 3:1 proportion (Gibco), supplemented with 5% Fetal Clone II serum (HyClone, Logan, United States), 10 ng/mL epidermal growth factor (Austral biologicals, San Ramon, United States), 24.3 µg/mL adenin (Sigma), 5 µg/mL insulin (Sigma), 5 µg/mL transferrin (Roche), 2×10$^{-9}$ M 3,3'5' tri-iodo-L-thyronin (Sigma), 0.4 µg/mL hydrocortisone (Calbiochem, La Jolla, United States), 10–10 M cholera toxin (ICN biomedicals), 100 IU/mL penicillin G (Sigma), and 25 µg/mL gentamycin (Schering, Pointe-Claire, Canada). Fibroblasts

TABLE 1

| TESTED PARAMETERS | TESTING RANGE | Mode 1 | Mode 2 | Mode 3 | Mode 4 | Mode 5 | Mode 6 |
| --- | --- | --- | --- | --- | --- | --- | --- |
| Pulse duration | 0 to 10$^6$ µsec | 500 | 500 | 500 | 500 | 250 | 250 |
| Inter-pulse interval (time off) | 0 to 10$^6$ µsec | 150 | 100 | 50 | 100 | 100 | 50 |
| # Pulse per Train | 1 to 100 Units | 4 | 4 | 4 | 8 | 4 | 4 |
| Inter-train Interval | 0 to 10$^6$ µsec | 1550 | 1700 | 1850 | 3300 | 700 | 850 |
| Power density | 3 to 600 W/m$^2$ | 500 | 500 | 500 | 500 | 500 | 500 |
| Total Treatment Time | 0 to 999 sec | 160 | 160 | 160 | 160 | 160 | 160 |

During the course of this experiment, six light pulsing patterns were tested. For each mode, key parameters combined altogether, including time on and time off intervals, sequential pulsing train characteristics, irradiance and total treatment time are described.

Photoinduction of Human Fibroblasts

Briefly, dermal fibroblasts isolated from normal human skin specimens were expanded and seeded in 25 cm$^2$ culture were cultured in DME, 10% fetal calf serum (HyClone), 100 IU/mL penicillin G, and 25 µg/mL gentamycin.

Cell isolation: The skin is composed of two important layers: the epidermis mainly composed of keratinocytes and the dermis that is composed of fibroblasts in a connective tissue matrix. Human epidermal keratinocytes and dermal fibroblasts were isolated from normal skin specimens. The skin specimens were removed during reductive breast surgery of two healthy adult females (F38 and F42), a face-lift (F64) and during the circumcision of a healthy newborn. The isolation procedures were initiated within three hours following the surgery according to previously published methods elaborated in our laboratory. Briefly, the skin specimens were washed five times with a phosphate buffer saline supplemented with 100 IU/ml penicillin G and 25 µg/ml gentamicin. The specimens were then cut in 3 mm wide strips and kept overnight at 4° C. in Hepes buffer containing 500 µg/ml thermolysin. The epidermis was mechanically separated from the dermis with forceps. The keratinocytes were dissociated from the epidermis by incubating the epidermal fragments under agitation at 37° C. for 30 minutes with 0.05% trypsin-0.1% EDTA in PBS. After the inhibition of the trypsin by addition of medium containing 10% serum and centrifugation, keratinocytes were expanded in the presence of irradiated 3T3 fibroblasts in T75 flasks and subsequently frozen until further use. Fibroblasts were dissociated from the remaining dermis fragments by incubation in a collagenase H solution at 37° C. under agitation. After centrifugation, the fibroblasts were plated in T75 flasks for expansion, subsequently frozen until further use. Production of tissue-engineered reconstructed skin equivalent. Dermal fibroblasts were cultivated in fibroblast medium containing 50 µg/mL of sodium ascorbate (Sigma) for four weeks to form sheets. After the fibroblast sheets were peeled from the bottom of the dishes, two of these sheets were then superimposed and cultured; the surface area of the construct was maintained by stainless anchoring ring for one week. After a week of dermal equivalent maturation, $1\times10^6$ keratinocytes were seeded on top of the reconstructed dermal equivalents. After 7 days of maturation under submerged conditions, the cell system was then brought to the air-liquid interface and cultivated in complete DME-HAM with 5% serum and 50 µg/mL of sodium ascorbate, and without EGF for an additional three weeks. Culture medium was changed three times a week.

Cell count and viability: The cells were counted manually (hemacytometer) and/or electronically (Coulter counter). Cell viability was determined using the trypan blue exclusion test.

Histological analysis: Biopsies of untreated and treated skin equivalents were fixed at least 24 hours in a Bouin solution (ACP, Canada) and embedded in paraffin. Five µm thick cross-sections were stained with Masson's trichrome. Pictures were taken at the 40× objective with a digital camera (CoolSnap RS Photometrics, Roper Scientific, Munich, Germany) for each condition.

III. Results

LED sequential pulsing modes for ideal in vitro reconstructed skin stimulation were evaluated. Several modes were tested, with sequential time on and time off to provide cell resting periods in between pulses. Various pulsed LED light durations as well as intervals distanced by a short resting gap were applied to human reconstructed skin, which generated diverse procollagen and MMP-1 productions profiles. Three final modes (A, B and C) were selected from among the most efficient pulsing modes tested in vitro. Clinical response seems to be wavelength dependent with increased depth of penetration at higher wavelengths relating to differences in specific protein expression and greater proliferating capacities by dermal papillary versus deeper reticular fibroblasts (A2, A3). In human skin, penetration depth at 660 nm is 2.23 mm, enough to reach the whole papillary layer in the dermis (A7).

Certain pulsing modes stimulated some reconstructed skin with predilection, leaving others without physiological effect. Tests were conducted to find the sequencing pulsing mode offering the best procollagen secretion over control, for a wide proportion of tested human reconstructed skin. FIG. 1 shows the representative average procollagen secretion versus control obtained after 11 pulsed LED light source treatments, achieved over a one-month period, at three different sequential pulsing modes, for two selected reconstructed skins, F42 and F64. Demonstrating a strong stimulation power over procollagen production for 2 reconstructed skins of different age, the sequential pulsing mode designated mode A was selected for further coming in vitro collagen synthesis analysis. This pulsed pattern proved to be optimal for all reconstructed skin tested. Procollagen production and inhibition of MMP-1 activity were also assessed over a one-month period, after 11 LED treatments in Mode A. FIG. 2 shows inversely proportionate patterns of total secretion following comparison of procollagen and MMP-1 concentrations during pulsed LED light therapy for F38, F42 and F64 reconstructed skin. All experiments were performed in triplicate.

IV. Discussion and Conclusion

Many parameters ought to be considered for efficacious stimulation of collagen synthesis. First, non thermal LED high-power density maximizes new collagen production by dermal fibroblasts by promoting procollagen synthesis. Collagenase (MMP-1) inhibition patterns, which could appear inversely proportional to procollagen synthesis events, are also observed on human reconstructed skin. This, combined with increased procollagen production, decreased MMP-1 activity supports the accumulation of additional dermal collagen. The cell becomes energized by such light treatments and accumulation of new collagen is possible.

As seen in FIG. 1, selected pulsing modes could suggest an age dependent response. The biological potentiality of the targeted cells seems to influence final results. As stated by Karu, the magnitude of biostimulation effect depends on the pre-treatment physiological conditions of the cell. The sequential pulsing mode selected for further analysis corresponds to the pulsing pattern promoting procollagen secretion for the widest tested population sample. Modes B and C generated procollagen production in the younger skin equivalent (F42), but no procollagen secretion was noticed for the oldest skin specimen, F64. Mode A increased procollagen synthesis in both reconstructed skins and generated an increase in procollagen synthesis of up to 40%.

Clinical response is thought to be wavelength dependent with increased depth of penetration at higher wavelengths. A deeper skin penetration may lead to differences in specific protein expression. In vitro, dermal papillary fibroblasts exhibit better growth potentials than dermal reticular fibroblasts (A2). At 660 nm, with increased depth of penetration, the stimulation covers the whole dermal papillary layer, providing the expected biological response in papillary fibroblasts. Other than wavelength, augmentation in protein synthesis seems to be associated with a combination of key parameters, as stated earlier.

Moreover, while such LED treatment increase type I procollagen production, it appears to inhibit in an inversely proportional manner the production of metalloproteinase (MMP), collagen degrading enzyme found in aging skin. Indeed, as free radicals are known to attack the collagen. As collagen diminishes, the skin's ability to regenerate and heal itself declines. The term elastosis describes age and sun related histopathological morphological alterations in the upper dermis. Free radicals can stimulate production in the body of collagen-digesting enzymes, such as collagenase and metalloproteinase (MMP).

Matrix metalloproteinase (MMP) activity is highly regulated. It plays a key role in dermal extracellular matrix turnover. Matrix metalloproteinases (MMPs) are a large family of proteolytic enzymes, which are involved in the degradation of many different components of the extracellular matrix. The MMPs have been classified into different groups including collagenases, gelatinases, stromelysins, and others. There is increasing evidence indicating that individual MMPs have important roles in aging skin. Controlled degradation of extracellular matrix (ECM) is essential for the homeostasis of the dermis. Recent evidence suggests that this homeostasis is out of balance in aging and photoaged skin. Downregulation of MMP gene expression combined with upregulation of procollagen production are key components for successful anti-aging photoinduction. The role of MMP-1 or collagen degrading enzyme using such non-ablative non-thermal LED therapy has been thoroughly studied since most dermal extracellular matrix is composed of collagen. Another matrix metalloproteinase, MMP-2, is a strong marker for other dermal matrix degrading enzyme activity. MMP-2 or Gelatinase-A is able to degrade elastin, fibronectin, type IV collagen, and gelatins but shows no activity against laminin or interstitial collagens. Also, these enzymes are thought to act co-operatively with the collagenases to effect the complete degradation of interstitial collagens. Downregulation of MMP gene expression is triggered by the above-described treatments (FIGS. 1 and 2).

Furthermore, both efficacy and safety of LED therapy were confirmed in vivo with a clinical study involving 53 patients. In fact, twelve (12) treatments led to a significant improvement in the appearance of wrinkles, skin tone and texture.

EXAMPLE 2

This example relates to a periorbital rhytid improvement by non-ablative, non-thermal led photoinduction.

Stimulating skin cells to produce collagen can partly reverse wrinkles, facial sag, rough skin texture, and external signs of aging such as thinning skin, lack of firmness and dullness resulting from a reduction in collagen. Healthy collagen gives the skin its softness, resiliency, suppleness as well as its ability to repair itself (50, 54). On the other hand, damaged collagen molecules become stiff and inflexible, and the skin appears old. Increasing stimulation of collagen synthesis in aging skin is realistic and can substantially improve the appearance of fine lines and even deeper wrinkles when performed correctly. However, this procedure requires a comprehensive approach for which there is little reported clinical experience to date. A review of the literature indicates that the efficacy of LLLT (Low Level Laser Therapy) for skin rejuvenation has not been established. Experiments using light-emitting diodes (LEDs) to invigorate in vitro fibroblast proliferation, growth factor synthesis, collagen production and angiogenesis suggest faster wound healing. Indeed, non-ablative LED therapy induces extracellular matrix changes, amplifies procollagen I and collagen I expressions, while structural protein changes are also observed in fibroblast tissue cultures, skin biopsies and open wounds (A1, 12, 32). Those metabolic modulations are thought to correlate with clinical improvement in photoaged skin. As stated in EXAMPLE 1, following eleven (11) LED exposures of determined pulse sequences performed over a one-month period on dermal fibroblast skin equivalents from healthy 38, 42 and 64 year old females (F38, F42, F64), it was observed that procollagen dosages augmented while total activity of matrix metalloproteinase-1 (MMP-1) decreased proportionally. Hence, pulsed LED light exposures seem to significantly catalyze resistance to photoaging damages by amplifying collagen production and decreasing collagenase (MMP-1) activity, resulting in overall increased collagen synthesis.

The tissue irradiation method tested is performed with a non-ablative non-thermal light source using photons to induce photobiochemical reactions, triggering skin collagen synthesis. The pulsed LED light source combines relatively high-power density and critical parameters that must be considered for successful collagen formation. For example, wavelength is a key parameter ensuring proper biological stimulation.

Reported evidence shows that normal and abnormal human fibroblast cell lines exhibit significantly higher cell counts when exposed to 660 nm light source (A1). Likewise, the fluence or total dose of energy released over a definite amount of time is another important determinant of efficacious LED therapy. Light intensity or irradiance delivered to the skin is also a leading factor to induce the anticipated stimulatory effects. In fact, threshold intensity must be exceeded to promote collagen production.

Biologically, fluence and irradiance are independent variables which ought to be considered, especially for medical applications. For instance, bearing in mind equal fluence delivered, irradiance values under the threshold point, even under prolonged irradiation time, would never produce biostimulatory effects. In addition, LED pulsing patterns may be thought to avoid cellular exhaustion leading to cell unresponsiveness or even apoptosis, which implies that specific triggering pulsing features must be rigorously tested and established.

Finally, optical positioning is another key requirement to precisely monitor an accurate working distance so as to provide the needed irradiance to ensure efficacious collagen production by dermal fibroblasts, as light energy propagation is carefully oriented and delivered over the skin surface.

An objective of the present example is to evaluate the efficacy and safety of an LED technology for non-ablative wrinkle reduction, focused on periorbital rhytides. LED therapy, either used alone or in combination with topical therapy improved significantly the appearance of skin tone and texture and reduced the appearance of wrinkles.

Clinical Study: IRB Services (FDA approved independent ethical review committee) reviewed the ethical aspects of the study. Informed consent was obtained after explanation of potential risks involved. Fifty-three (53) patients were recruited, selected according to the Fitzpatrick Classification of Wrinkling and Degree of Elastosis.

TABLE 2

| Mild Elastosis Class I (Subtype 1) | Mild Elastosis Class I (Subtype 2) | Mild Elastosis Class I (Subtype 3) | Moderate Elastosis Class II (Subtype 4) | Moderate Elastosis Class II (Subtype 5) | Moderate Elastosis Class II (Subtype 6) |
| --- | --- | --- | --- | --- | --- |
| n = 5 | n = 21 | n = 16 | n = 6 | n = 1 | n = 0 |

Table 2 outlines the patient distribution according to Fitzpatrick Classification.

Class I: Mild Elastosis Subtype 1-2-3: Fine textural changes with subtly accentuated skin lines.

Class II: Moderate Elastosis Subtype 4-5-6: Distinct papular elastosis, dyschromia.

A double-blind, side-by-side comparison study with photoaged patients (mean age=44.4 years old, for n=40), Fitzpatrick skin types I, II, and III, treated 12 times over a 4-week period with an LED device on periorbital rhytides was performed (Table 2). Patients were evaluated by digital photographs and PRIMOS profilometry performing Phaseshift Rapid In-Vivo Measurements of Skin (3D in-vivo optical skin imaging) to quantify precise clinical improvements (60).

To maximize the benefits of the treatment, a topical regular moisturizer without active ingredients was applied daily, combined with LED treatment.

Treatment Parameters:

Treatment site: Periorbital area (crowfeet)

Treated side: Randomly assigned, with no cooling method: sequentially pulsed LED treatment of a few seconds with total fluence>4 J/cm$^2$ on one side.

Untreated control side: Randomly assigned, with no cooling method: few minutes total fluence of 0 J/cm$^2$ on the contralateral (sham) side.

Schedule: A total of 3 treatments per week, for 4 consecutive weeks (12 treatments in total).

The parameters relating to irradiation are summarized in Table 3.

TABLE 3

| PARAMETERS | UNITS | MODE 1 |
|---|---|---|
| Pulse duration (time on) | Microseconds (μsec) | 500 |
| Inter-pulse Interval (time off) | Microseconds (μsec) | 150 |
| # Pulse per Pulse Train | Units | 4 |
| Inter-train Interval | Microseconds (μsec) | 1550 |
| Power density | W/m$^2$ | 500 |
| Total Treatment Time | Seconds | 160 |

The parameters above combined altogether to achieve the optimal light pulsing mode.

The measurements taken during and after the experiment were 3D surface topography (PRIMOS: GFM Germany) readings were taken at Week 0 (pre-treatment), 4 and 12. Surface pre-treatment topography measurements compared to post-treatment measurements (Resolution+/−1 micron ($10^{-6}$ m)). Before and after pictures were computer-matched prior to results analysis. Further, the pictures were review at quartile scale blinded observer clinical analysis of digitalized pictures at Week 0, 4 and 12 (week 0=pre-treatment pictures). Before and after assessment of the degree of clinical improvement: 0-25% Fair, 26-50% Good, 51-75% Very good, 76-100% Excellent.

Results

Most subjects involved in the clinical study reported subjective improvement in the quality and visual aspect of their skin. An overall enhancement of 58% was obtained in the global appearance of the skin, 8 weeks after the final treatment. Other clinical results included reduction in skin roughness, pore size and redness. No adverse effect or discomfort has been linked to the treatment, most probably due to the absence of thermal damage during treatment. A light redness could have occurred following treatment, usually vanishing an hour post-treatment. Moreover, no allergy, immune reaction or infection was noticed. Enhancement of skin appearance was lightly noticeable right after LED exposure, but enhancement in wrinkle reduction and improved pore size, firmness, softness, resiliency and suppleness were observed up to 4 months post-treatment.

An objective method providing more accurate quantification of facial wrinkles was used in this study. PRIMOS Software analysis was performed on pre- and post-treatment matched pictures (prior to analysis, all pictures were matched either manually or with the software application, ensuring rigorous comparison). Afterward, the average maximum height for a given profile, the Rz value ($Rz=(1/N)*[(H1+H2+\ldots H_N)-(L1+L2+\ldots L_N)]$), was calculated as the mean peak-to-valley height, highs and lows (H and L) from the profile lines, providing a measurement of wrinkle severity (B6).

After twelve treatments, the mean improvement of the Rz value reaches 24.6 μm for 41 patients (n=41, results of 8 remaining participants are currently being analyzed), implying that the average wrinkle depth of the studied crowfeet area is reduced by 24.6 μm (data not shown).

Compared pre- and post-treatment Rz values reached up to a 225.2 μm variation for one study participant (age=46 years old), proving an important wrinkle reduction after therapy. A representative sample of PRIMOS pre- and post-treatment pictures are shown in FIGS. 4A to 4D.

Table 4 gives more specific details regarding the study cohort average percent improvement following treatment of the right crowfeet area with the following the 12 treatments). Quantitative improvements are measures by comparison of both pre and post treatment PRIMOS Ra and Rz values.

TABLE 4

| Patient ID | Age | Gender | Fitzpatrick wrinkle classification system | Fitzpatrick phototype classification system | Post-treatment improvements in wrinkle score | Rz (%) | Ra (%) | Overall Skin Improvement (%) |
|---|---|---|---|---|---|---|---|---|
| P1 | 39 | F | I.1 | 2 | Y | 25 | 14 | 70 |
| P2 | 38 | M | I.2 | 3 | Y | 17 | 31 | 80 |
| P3 | 41 | F | I.2 | 2 | Y | 17 | 22 | 40 |
| P4 | 48 | F | II.5 | 2 | Y | −14 | −7 | 40 |
| P5 | 45 | F | I.3 | 2 | N | 8 | 7 | 30 |
| P6 | 40 | F | I.2 | 3 | Y | 29 | 14 | 40 |
| P7 | 40 | F | I.2 | 2 | Y | 9 | 4 | 40 |
| P8 | 41 | M | I.3 | 3 | Y | 26 | 14 | 80 |
| P9 | 59 | F | II.4 | 1 | Y | 40 | 30 | 40 |
| P10 | 61 | F | II.4 | 1 | Y | 21 | 22 | 45 |
| P11 | 44 | F | I.2 | 2 | N | 14 | 24 | 60 |
| P12 | 44 | M | I.3 | 3 | Y | 30 | 23 | 70 |
| P13 | 62 | F | I.3 | 2 | Y | 16 | 9 | 40 |
| P14 | 48 | F | II.4 | 2 | Y | −8 | 2 | 60 |
| P15 | 53 | F | I.3 | 2 | Y | 37 | 31 | 90 |
| P16 | 37 | F | I.2 | 1 | N | 30 | 22 | 45 |

TABLE 4-continued

| Patient ID | Age | Gender | Fitzpatrick wrinkle classification system | Fitzpatrick phototype classification system | Post-treatment improvements in wrinkle score (%) | Rz (%) | Ra (%) | Overall Skin Improvement (%) |
|---|---|---|---|---|---|---|---|---|
| P17 | 40 | F | I.2 | 3 | N | 30 | 48 | 40 |
| P18 | 43 | F | I.2 | 3 | N | 0 | 0 | 20 |
| P19 | 44 | F | I.1 | 3 | Y | 40 | 44 | 80 |
| P20 | 46 | F | I.1 | 2 | Y | 10 | 5 | 40 |
| P21 | 44 | F | I.2 | 3 | Y | 33 | 34 | 70 |
| P22 | 40 | F | I.2 | 3 | N | 10 | 11 | 30 |
| P23 | 49 | F | I.3 | 2 | N | 11 | 16 | 35 |
| P24 | 43 | F | I.3 | 3 | Y | 11 | 19 | 80 |
| P25 | 43 | F | I.3 | 2 | Y | 14 | 11 | 45 |
| P26 | 52 | F | II.4 | 2 | Y | 6 | 1 | 40 |
| P27 | 39 | F | I.3 | 3 | Y | −13 | −7 | 20 |
| P28 | 45 | F | I.2 | 2 | Y | 20 | 19 | 70 |
| P29 | 57 | F | II.4 | 3 | Y | 49 | 56 | 70 |
| P30 | 33 | F | I.2 | 2 | N | 6 | 7 | 55 |
| P31 | 53 | F | I.3 | 3 | N | 23 | 27 | 55 |
| P32 | 41 | F | I.3 | 2 | N | 38 | 42 | 60 |
| P33 | 46 | F | I.3 | 3 | Y | 51 | 38 | 100 |
| P34 | 41 | F | I.2 | 3 | N | 20 | 12 | 35 |
| P35 | 39 | F | I.3 | 3 | N | 12 | 8 | 40 |
| P36 | 41 | F | I.2 | 1 | N | 20 | 19 | 35 |
| P37 | 41 | F | I.3 | 1 | Y | 15 | 11 | 80 |
| P38 | 37 | F | I.1 | 1 | N | 13 | 12 | 35 |
| P39 | 58 | F | II.4 | 2 | N | −7 | −2 | 80 |
| P40 | 42 | F | I.3 | 2 | N | 3 | 1 | 20 |
| AVERAGE IMPROVEMENT (%) | | | | | | | | 52 |

Table 4 illustrates that the study cohort average percent improvement following treatment of the right crowfeet area with the LumiPhase-R (12 treatments). Quantitative improvements are measures by comparison of both pre and post treatment PRIMOS Ra and Rz values.

This example shows that LED therapy goes beyond the concept of thermal injury to achieve a clinical response. The tested therapy was shown to promote new collagen formation and improvement in skin tone, texture and fine lines, noticeably enhancing overall appearance by 58% in a significant number of patients (n=49). In addition, lack of adverse effects confirms that this new non-ablative non-thermal light source is safe and efficacious.

The therapy can be used alone or in combination with skin rejuvenation regimens. Thus, it can serve as a complementary treatment to other skin rejuvenation therapies or topical agents that also enhance collagen production. Indeed, topical cosmeceutical agents have been observed to act as adjuncts to non-ablative rejuvenation. A potent synergy between LED therapy and topical agents seems to increase skin resiliency and firmness. During the course of this study, regular moisturizing cream without active ingredients was applied daily before bedtime on the crowfeet area.

The main advantages of the tested therapy are numerous when compared to low-level lasers. First, this device allows for treatment of larger surfaces with more accuracy, using several LED arrays. Moreover, the optical positioning system ensures, through optimal and uniform beam delivery over the skin surface, a relatively precise light release so a suitable quantity of photons are then reaching the targeted cells.

Furthermore, the tested treatment head has been designed like a facial mask, allowing for more adequate matching of the facial contours, thereby increasing the system's overall performance and convenience. In addition, a greater clinical response is to be anticipated from tested light therapy since photons are delivered via a unique sequential mode that seems to prevent fibroblast exhaustion by providing different resting intervals between pulses. This, in turn, favours a potent cell response during the complete treatment. Finally, wrinkle reduction and other skin improvements obtained within this study can be related to therapy's relatively high-power density which maximizes procollagen synthesis by dermal fibroblasts. Over a very short treatment time, a high intensity is delivered, generating an optimal physiological effect, in a relatively safe and relatively painless manner. It is important to note that the tested is effective for a wide range of skin colours, even for dark complexion patients. However, phototypes V & VI would probably loose much irradiance through interference with their high melanin content at the dermo-epidermal junction.

Herein, average reduction of wrinkle depth is evaluated at 24.6 μm for n=41 patients, which suggests in vivo that new collagen secretion is filling fine lines and moderate wrinkles. A great clinical response is achieved following treatments on the crowfeet area, and additional improvement is likely after more treatment sessions, in a cumulative manner. Treatment of contiguous facial areas could intensify overall skin improvements. A significant increase in skin firmness and resiliency is also to be expected for the periorbital area.

Figure 38:
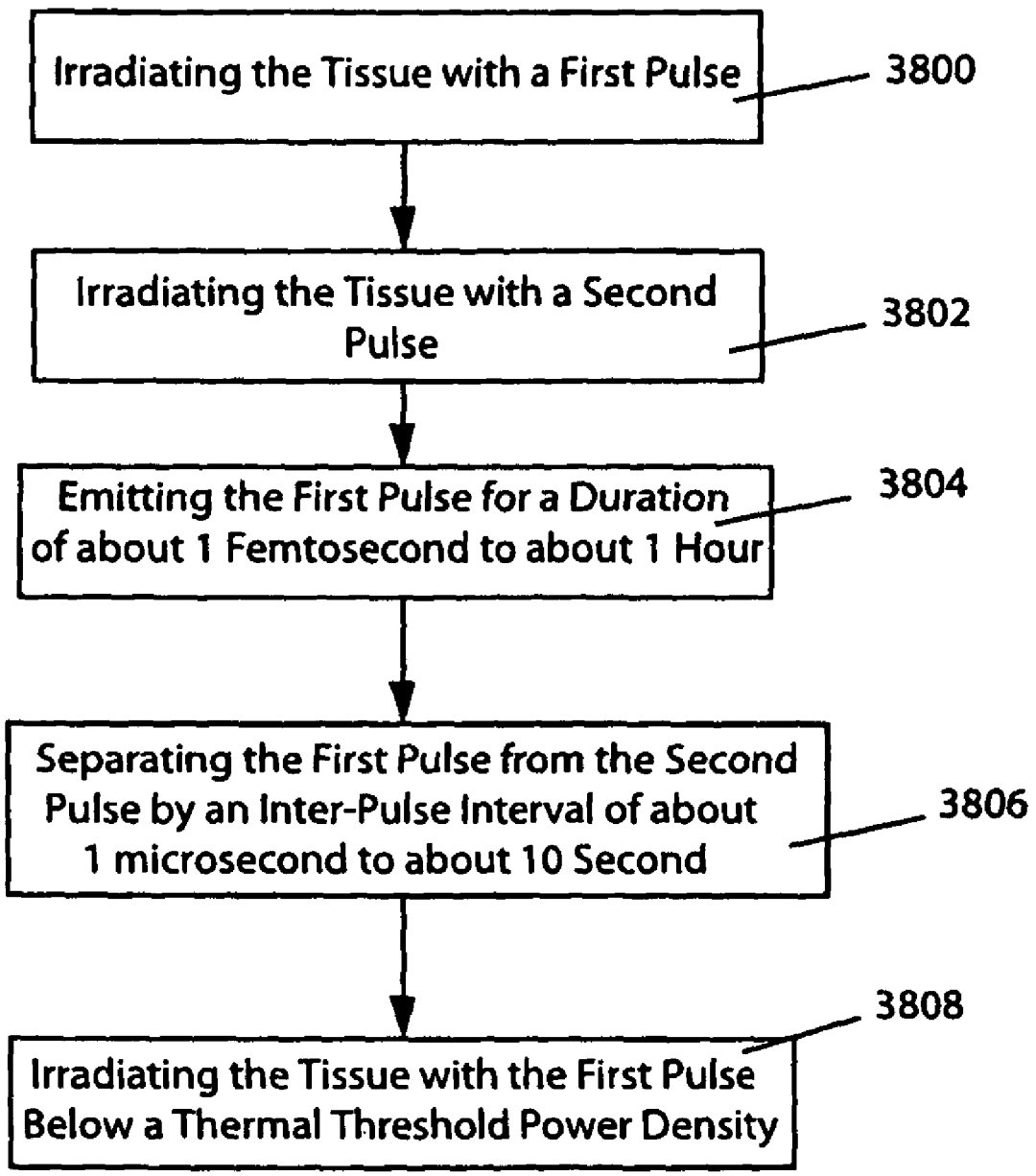
FIG. 38 is a flow chart illustrating a method of the present invention.

Referring to FIG. 38, a method of photoactivating mammalian tissue causing a predetermined physiological change is illustrated. The steps include irradiating the tissue with a first pulse having a power density above an activation threshold power density (step 3800). The activation threshold power density is a power density below which the predetermined physiological change is substantially absent from the mammalian tissue upon the mammalian tissue being irradiated with the radiation Further, above which the predetermined physiological change is substantially present in the mammalian tissue upon the mammalian tissue being irradiated with the radiation.

The tissue is irradiated with a second pulse (step 3802) and the first pulse is emitted for a duration of about 1 femtosecond to about 1 hour (step 3804). The first and second pulses are separated by an inter-pulse interval of about 1 microsecond to about 10 seconds (step 3806). Typically the first and second pulses have a wavelength of about 400 nanometers to about 1500 nanometers and a power density of about 0.1 mW/cm$^2$ to about 10 W/cm$^2$, and more specifically about 30 mW/cm$^2$ to about 100 mW/cm$^2$.

In further embodiments, the activation threshold power density can be about 0.1 mW/cm$^2$, about 10 mW/cm$^2$, and/or about 50 mW/cm$^2$. The inter-pulse interval can be about 10 microseconds to about 5 milliseconds or about 100 microseconds to about 0.5 milliseconds. Duration of the first and subsequent pulses can be about 100 microseconds to about 5 milliseconds or about 250 microseconds to about 1 millisecond. Typically, all the pulses are emitted by at least one light emitting diode (LED). Another embodiment includes the step of emitting the first pulse for about 250 microseconds to about 1 millisecond and the inter-pulse interval is from about 100 microseconds to about 0.5 millisecond.

The physiological effect of the photoactivation method can include at least one of stimulating collagen production by fibroblasts contained within the skin tissue, substantially reversing at least in part skin damages caused by aging, reversing at least in part damages caused to an extracellular matrix of the skin by aging, and modulating an apoptosis response of the skin tissue.

An embodiment utilizes ratios of key factors, including a ratio of the duration divided by the inter-pulse interval can be about 0.1 to about 10 and about 0.5 to about 2. Another embodiment is the power density of radiation within the tissue is below one of about 10 percent and about 1 percent of the activation threshold power density during the inter-pulse interval.

Furthermore, a minimal power density of the radiation within the tissue during each pulse can be about two times, about ten times, about 100 times, and about 10,000 times as large as a maximal power density of the radiation within the tissue during the inter-pulse interval.

Another method of photoactivation included the steps of irradiating the tissue with a first pulse having a power density below a thermal threshold power density (step 3808). The thermal threshold power density is a value over which a temperature of the irradiated tissue increases to a temperature greater than a predetermined overheating temperature. The thermal threshold power density can be about 10 mW/cm$^2$, about 100 mW/cm$^2$, about 1 W/cm$^2$, and about 1 kW/cm$^2$. The overheating temperature can be about 2° C., about 0.5° C., and about 0.1° C. over a maximal non-pathological in-vivo temperature of the mammalian tissue. Further, the activation threshold power density is about 30 mW/cm$^2$ and the thermal threshold power density is about 100 mW/cm$^2$.

Figure 39:
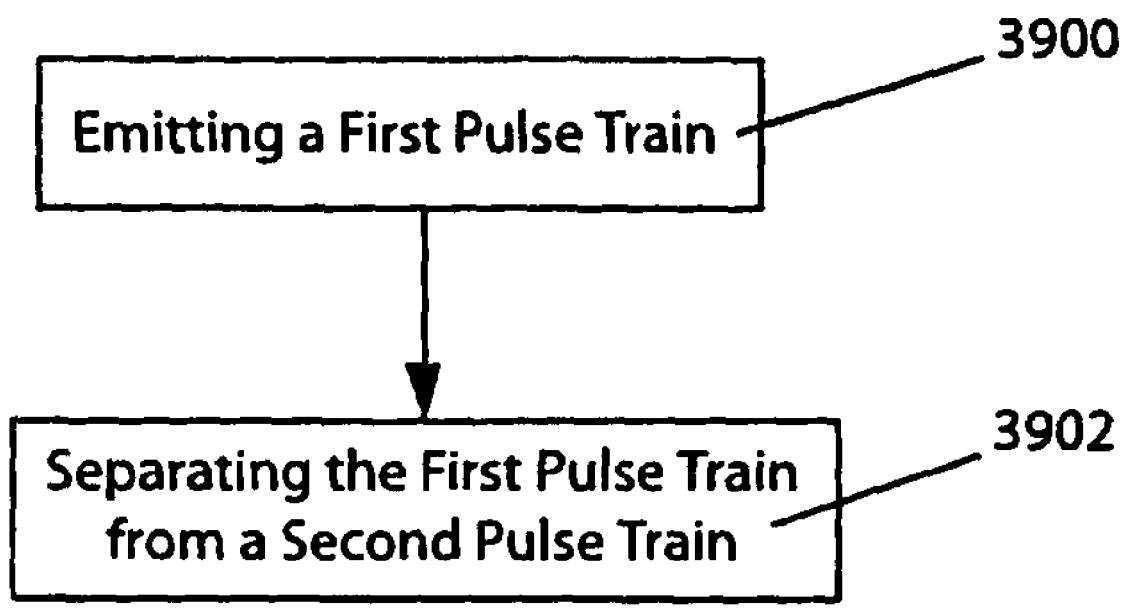
FIG. 39 is a flow chart illustrating another method of the present invention.

FIG. 39 illustrates a method wherein at least two pulse trains are utilized. Each pulse train includes a first pulse and a second pulse. The method includes emitting a first pulse train (step 3900) and separating the first pulse train from a second pulse train by an inter-pulse train interval of about 1 microsecond to about 1 second (step 3902). The inter-pulse train interval is one of 500 microsecond to about 1 second, about 750 microseconds to about 2,250 microseconds, and about 500 microseconds to about 2.25 milliseconds. Other embodiments of the inter-pulse train interval are about 2 to about 10 and specifically, about 3.

A number of pulses emitted within each pulse train can be 2 to 100 pulses, 4 to 10 pulses, and 3 to 10 pulses, all of which are within the duty cycle of the light source, specifically the LED.

Figure 40:
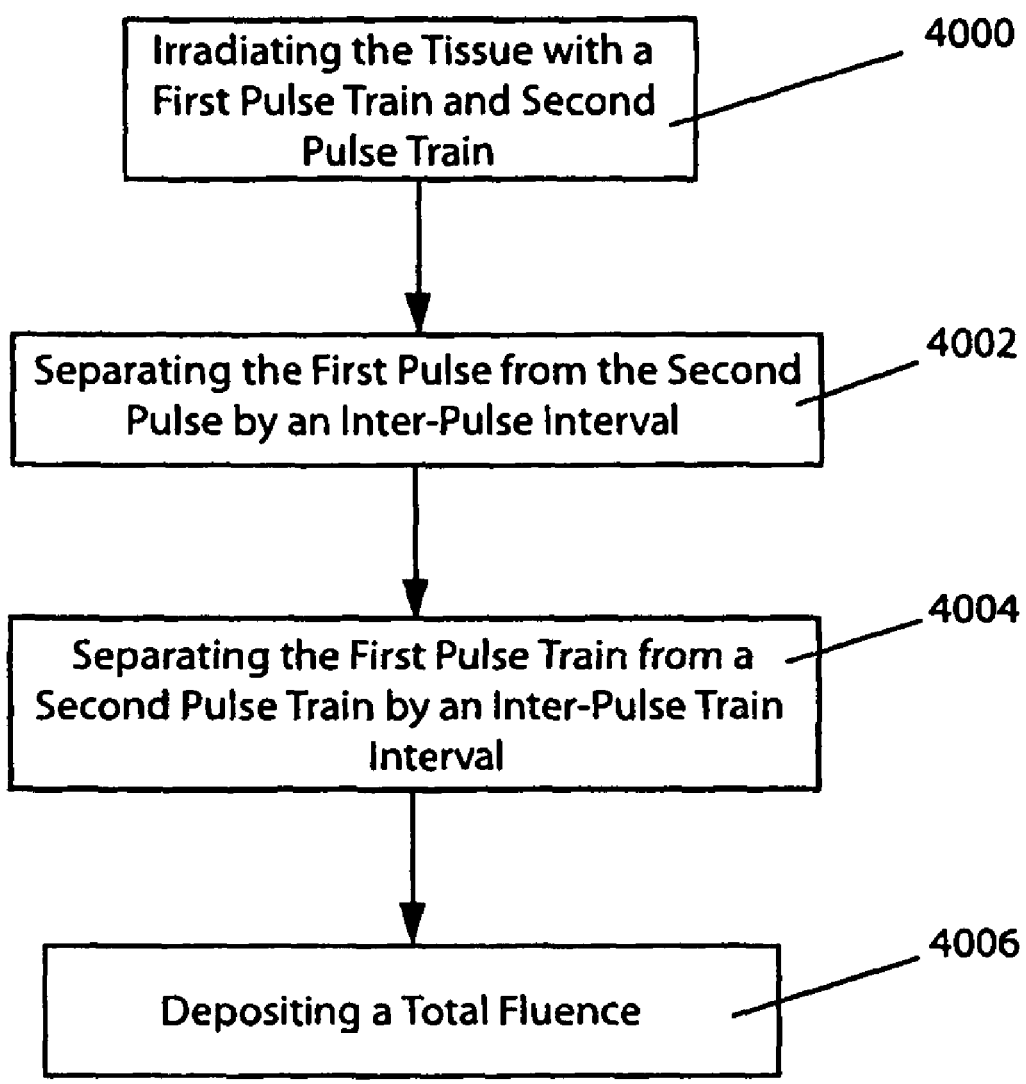
FIG. 40 is a flow chart illustrating a further embodiment of a method of the present invention.

Another method of photoactivating mammalian tissue causing a predetermined physiological change is illustrated in FIG. 40. The tissue can be irradiated with a first pulse train and a second pulse train, each pulse train having at a first pulse and a second pulse (step 4000). The first pulse can be separated from the second pulse by an inter-pulse interval (step 4002) and the first pulse train can be separated from a second pulse train by an inter-pulse train interval (step 4004). In embodiments, the inter-pulse train interval can be about 1 microsecond to about 1 second, 500 microsecond to about 1 second, about 750 microseconds to about 2,250 microseconds, or about 500 microseconds to about 2.25 milliseconds. Further, a ratio of the inter-pulse train interval to the inter-pulse interval is about 2 to about 10, and specifically the ratio of the inter-train pulse interval to the inter-pulse interval is about 3. Other embodiment include a number of pulses within each pulse train is one of 2 to 100 pulses, 4 to 10 pulses, and 3 to 10 pulses.

Other steps include of depositing a total fluence from the first and second pulse trains to the tissue of about 0.001 J/cm$^2$ to about 20,000 J/cm$^2$ (step 4006). Alternately, the total fluence can be about 4 J/cm$^2$ to about 10 J/cm$^2$.

Figure 41A:
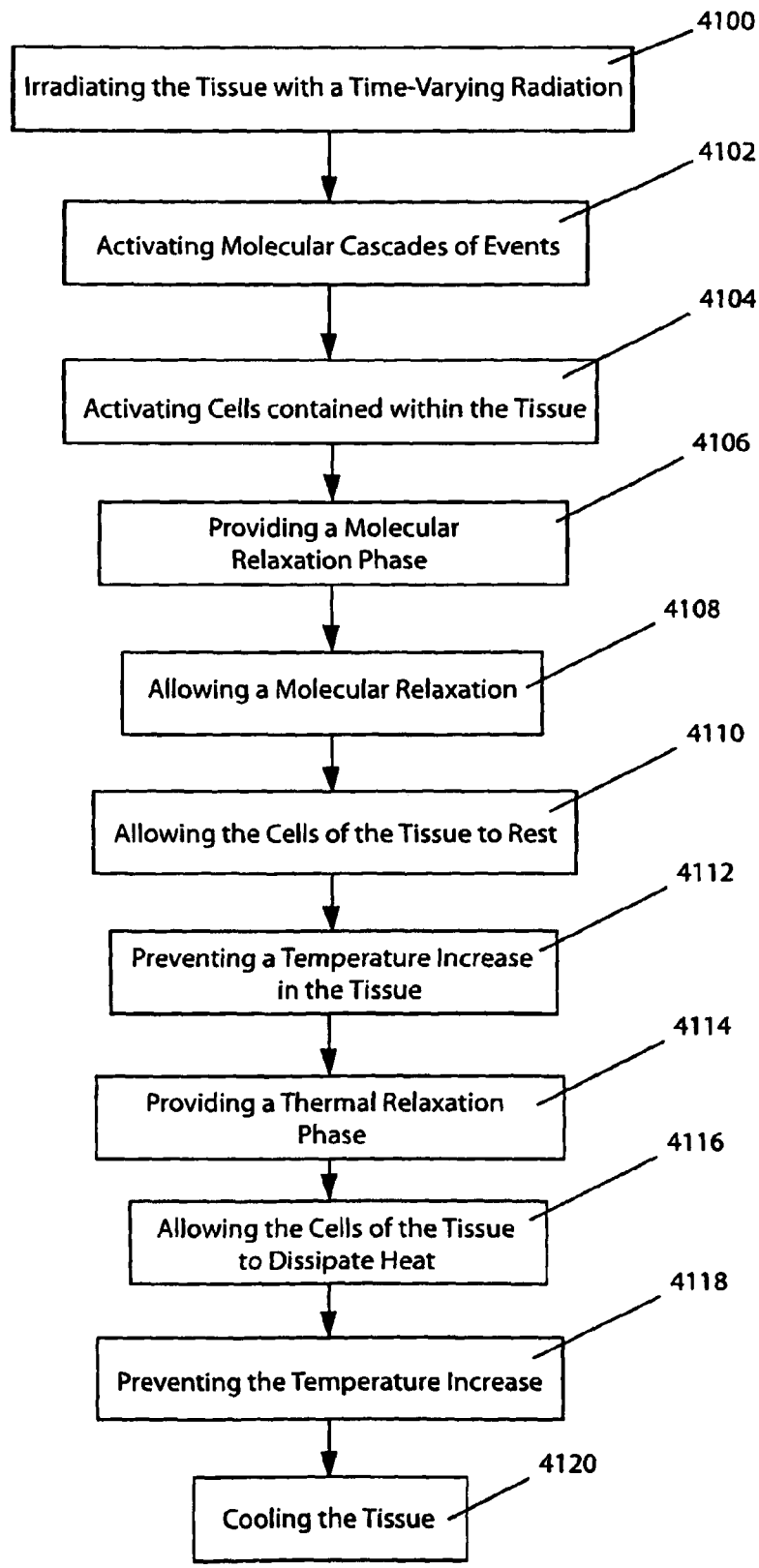
FIG. 41a is a flow chart illustrating another method of the present invention.
Figure 41B:
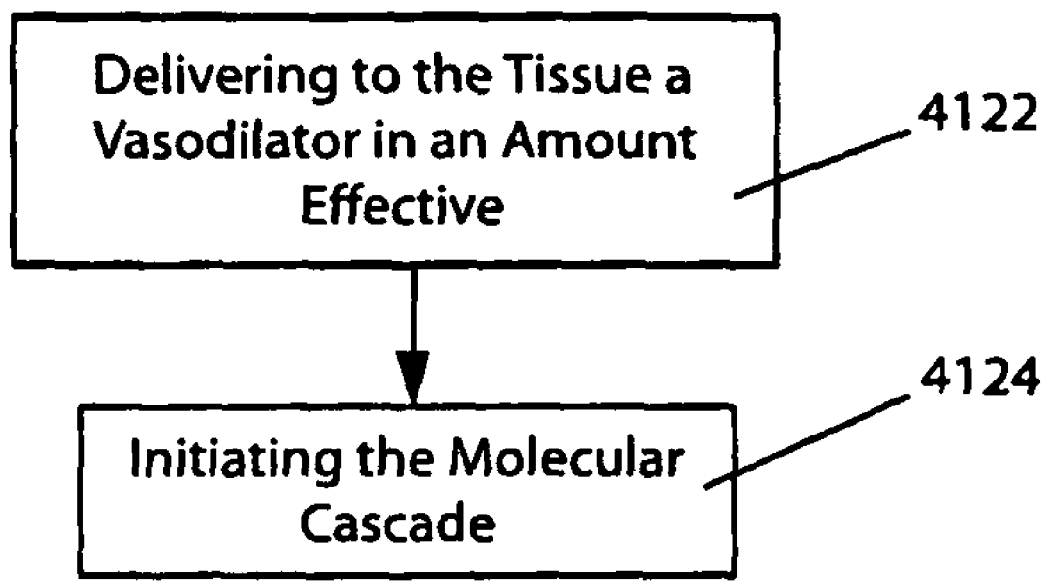
FIG. 41b is a flow chart illustrating another method of the present invention.

Turning to FIG. 41, a method of photoactivating mammalian tissue causing a predetermined physiological change is illustrated. The steps include irradiating the tissue with a time-varying radiation including a power density temporal profile (step 4100) The irradiating step can include activating molecular cascades of events (step 4102) and activating cells contained within the tissue (step 4104). A molecular relaxation phase can be provided (step 4106) and includes additional methods. Molecular relaxation can be allowed wherein a reversible molecular conformational changes are reversed at least in part so that the molecular cascades of events are reactivatable (step 4108) and allowing the cells of the tissue to rest so as to prevent at least in part cell exhaustion during the irradiation (step 4110).

Further embodiments include preventing a temperature increase in the tissue above an overheating temperature (step 4112) at which the cascade of events triggered by the radiation are substantially reversed. A thermal relaxation phase can be provided (step 4114) that includes allowing the cells of the tissue to dissipate heat (step 4116) so as to remain substantially below the overheating temperature. Further, temperature increases can be prevented by one or more methods (step 4118), including by a thermal inertia of the tissue, cooling the tissue (step 4120) which can include active convective cooling and delivering to the tissue a vasodilatator (step 4122) in an amount effective to cause a vasodilatation within the tissue.

Embodiments include power density temporal profiles remaining below a thermal threshold above which the temperature within the tissue is likely to increase above the overheating temperature. Additionally, the molecular cascade of events can be initiated by receiving, by an antenna molecule, least one photon contained within the radiation (step 4124). Further, the molecular cascade of events occurs partly in the mitochondria of the cells of the tissue and include reversible conformational changes that are reversed during the molecular relaxation phases. Activating the cells can also include progressively increasing a mitochondrial activity level within the cells of the tissue.

Further to the above embodiments FIG. 42 illustrates a method of defining a plurality of pulse trains (step 4200), each pulse train including a plurality of radiation pulses having a predetermined pulse duration. The plurality of radiation pulses can be separated by an inter-pulse interval (step 4202) and the pulse trains can be separated by an inter-pulse train interval (step 4204), the inter-pulse train interval being substantially larger than the inter-pulse interval. Another step can be allowing an antenna molecule to initiate the molecular cascades of events (step 4206).

An embodiment configures the plurality of pulses within each pulse train to a number of pulses to bring the cells to a suitable level of activation. Alternately, or in addition, the number of pulses within each pulse train can be a number preventing the cells from substantially reaching a steady state of activation (i.e. 4 to 10 pulses). The inter-train interval can provide cellular relaxation phases and allows the cells of the tissue to rest so as to prevent at least in part at least one of cell exhaustion and mitochondrial exhaustion during the irradiation. Specifically, an example of an inter-train interval is about 750 microseconds and about 2,250 microseconds.

Figure 43:
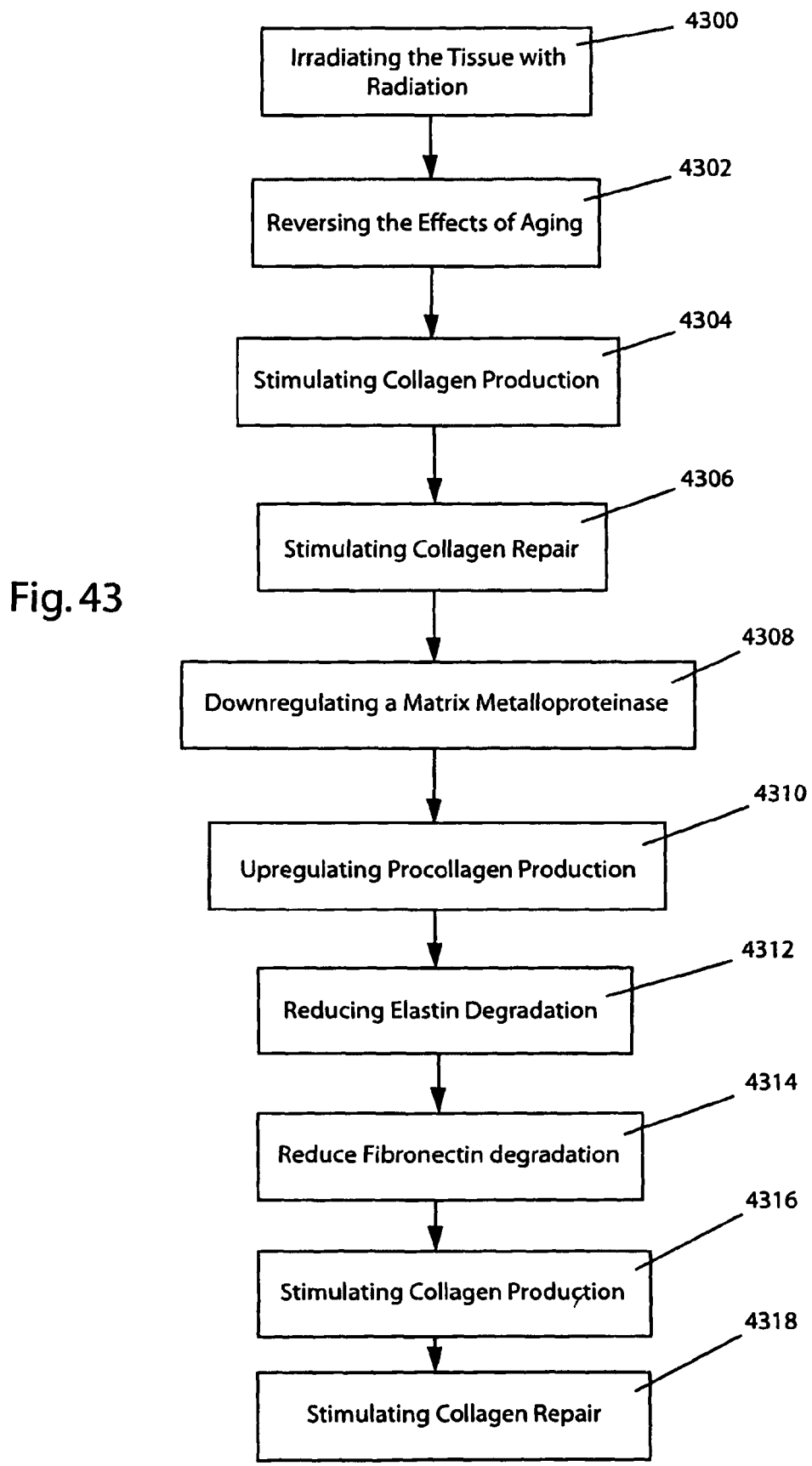
FIG. 43 is a flow chart illustrating an embodiment of the method.

Another method is illustrated in FIG. 43, and is a method for regenerating an extracellular matrix in mammalian tissue by irradiating the tissue with radiation to regenerate the extracellular matrix (step 4300). The radiation can perform at least one of partially reversing the effects of aging within the skin tissue (step 4302), stimulating collagen production within the tissue (step 4304), stimulating collagen repair within the extracellular matrix (step 4306), downregulating a matrix metalloproteinase (MMP) gene expression within the cells of the tissue (step 4308), upregulating procollagen production within the cells of the tissue (step 4310), reducing elastin degradation within the extracellular matrix (step 4312), reducing fibronectin degradation within the extracellular matrix (step 4314), stimulating collagen production within the tissue (step 4316) and stimulating collagen repair within the extracellular matrix (step 4318).

Figure 44:
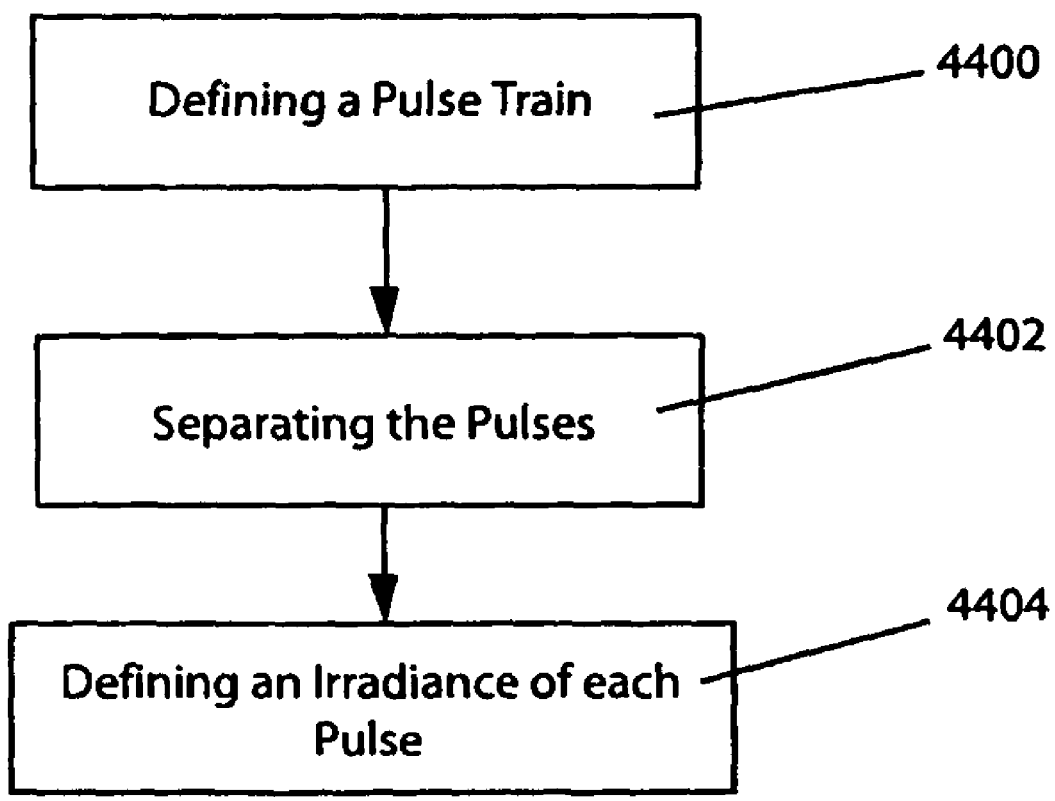
FIG. 44 is a flow chart illustrating another embodiment.

FIG. 44 illustrates defining a pulse train (step 4400) including a plurality of radiation pulses wherein the pulses each have a duration of from about 250 microsecond to about 1 millisecond, separating the pulses from each other by an inter-pulse interval (step 4402), the inter-pulse interval is about 100 microseconds to about 500 microseconds; and defining an irradiance of each pulse in the tissue of about 30 mW/cm$^2$ to about 100 mW/cm$^2$ (step 4404).

Figure 45A:
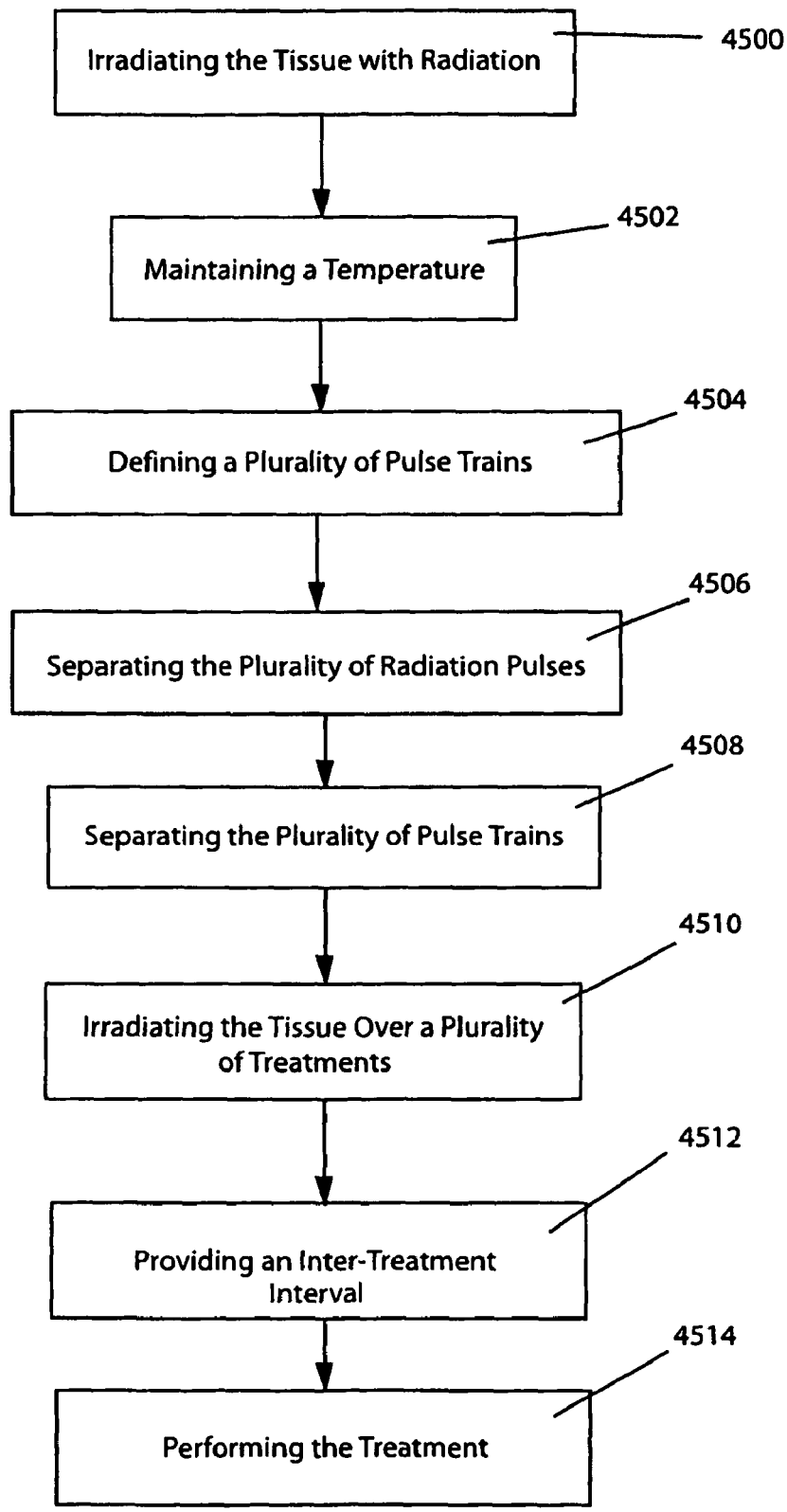
FIG. 45a is a flow chart illustrating a further method embodiment.

Turning now to FIG. 45, a method for reducing damages previously caused to a mammalian skin tissue, include the steps of irradiating the tissue with radiation having a power density temporal profile having a power density within the tissue greater than an activation threshold over a predetermined time interval (step 4500), and maintaining a temperature of the tissue below an overheating temperature by selecting the predetermined time interval (step 4502). In an embodiment, the overheating temperature is about 5° C. above a maximal non-pathological in-vivo tissue temperature.

Further, steps of defining a plurality of pulse trains, each pulse train including a plurality of radiation pulses having a predetermined pulse duration (step 4504), separating the plurality of radiation pulses by an inter-pulse interval (step 4506) and separating the plurality of pulse trains by an inter-train interval, the inter-train interval being substantially larger than the inter-pulse interval (step 4508). These steps are similar to the similar steps above. The embodiment can also include irradiating the tissue over a plurality of treatments, wherein a treatment includes one or more pulse trains (step 4510), providing an inter-treatment time interval between treatments (step 4512) and performing the treatment to substantially reduce damages previously caused to the mammalian skin tissue (step 4514).

A further embodiment includes applying the treatments within a rejuvenating phase wherein the tissue is substantially rejuvenated (step 4516). A maintenance phase can follow the rejuvenating phase and including steps of substantially maintaining the rejuvenation of the tissue (step 4518). Alternate embodiments include the inter-treatment time interval during the maintenance phase is larger than an inter-treatment time interval during the rejuvenating phase. Also, the inter-treatment time interval during the maintenance phase can be larger than the duration of the rejuvenating phase. In specific embodiments, the inter-treatment time interval during the rejuvenating phase is one of about 1 minute to about 1 year, about 1 hour to about 1 month, about 1 day to about 1 week, and about 3 days to about 4 days. Another embodiment can be where the inter-treatment time interval during the maintenance phase is from about 1 day to about 5 years, about 1 month to about 1 year, and about 1 year.

The rejuvenating phase includes at least one of 2 to 1000 treatments, 2 to 50 treatments, 5 to 20 treatments, and 12 treatments. The inter-treatment time interval during the rejuvenating phase can be about 1 day to about 1 week and wherein the inter-treatment time interval during the maintenance phase is about 1 month to about 1 year. Another embodiment of the method includes substantially preventing at least one of a cellular exhaustion and a mitochondrial exhaustion (step 4520).

As above, in FIG. 43, radiation can partially reverse the effects of aging within the skin tissue, stimulate collagen production within the tissue, stimulate collagen repair within the extracellular matrix, downregulate a matrix metalloproteinase (MMP) gene expression within the cells of the tissue, upregulate procollagen production within the cells of the tissue, reduce elastin degradation within the extracellular matrix, reduce fibronectin degradation within the extracellular matrix, stimulate collagen production within the tissue, and stimulate collagen repair within the extracellular matrix.

Pulse train embodiment include the same features as above, including about 4 to about 10 pulses, the pulses within each pulse train lasting about 250 microseconds to about 1 millisecond, the inter-pulse interval is about 100 microseconds to about 0.5 millisecond, and he inter-train interval is about 500 microseconds to about 1 second. The fluence of each treatment is one of about 1 mJ/cm$^2$ to about 1 kJ/cm$^2$, about 1 J/cm$^2$ to about 50 J/cm$^2$, and about 4 J/cm$^2$ to about 10 J/cm$^2$.

The substantially rejuvenated tissue can include cells that are less likely to experience apoptosis than the cells were prior to the irradiation. Reducing a likelihood of apoptosis can be performed by at least one of reversing an aging process, and reversing environmental factors.

Another method includes applying an active topical formulation to the skin prior to irradiation. The active topical formulation promotes collagen synthesis and can include antioxidants and a vitamin selected from the set consisting of vitamins A, B$_5$, C and E.

The radiation described in the embodiments above can be suitable for treating at least one of cheloids by photoinhibition, atrophic scars through photoactivation, acne, eczema, psoriasis, vitiligo, rosacea, promoting hair regrowth, removing at least in part exogenous pigments in the skin, dermal hypermelanosismelanosis, an adnexial tumor, cutaneous hyperpigmentation, smoothing wrinkles, reducing a thinning skin, reducing a lack of firmness of the skin, and reducing dullness of the skin.

Figure 46:
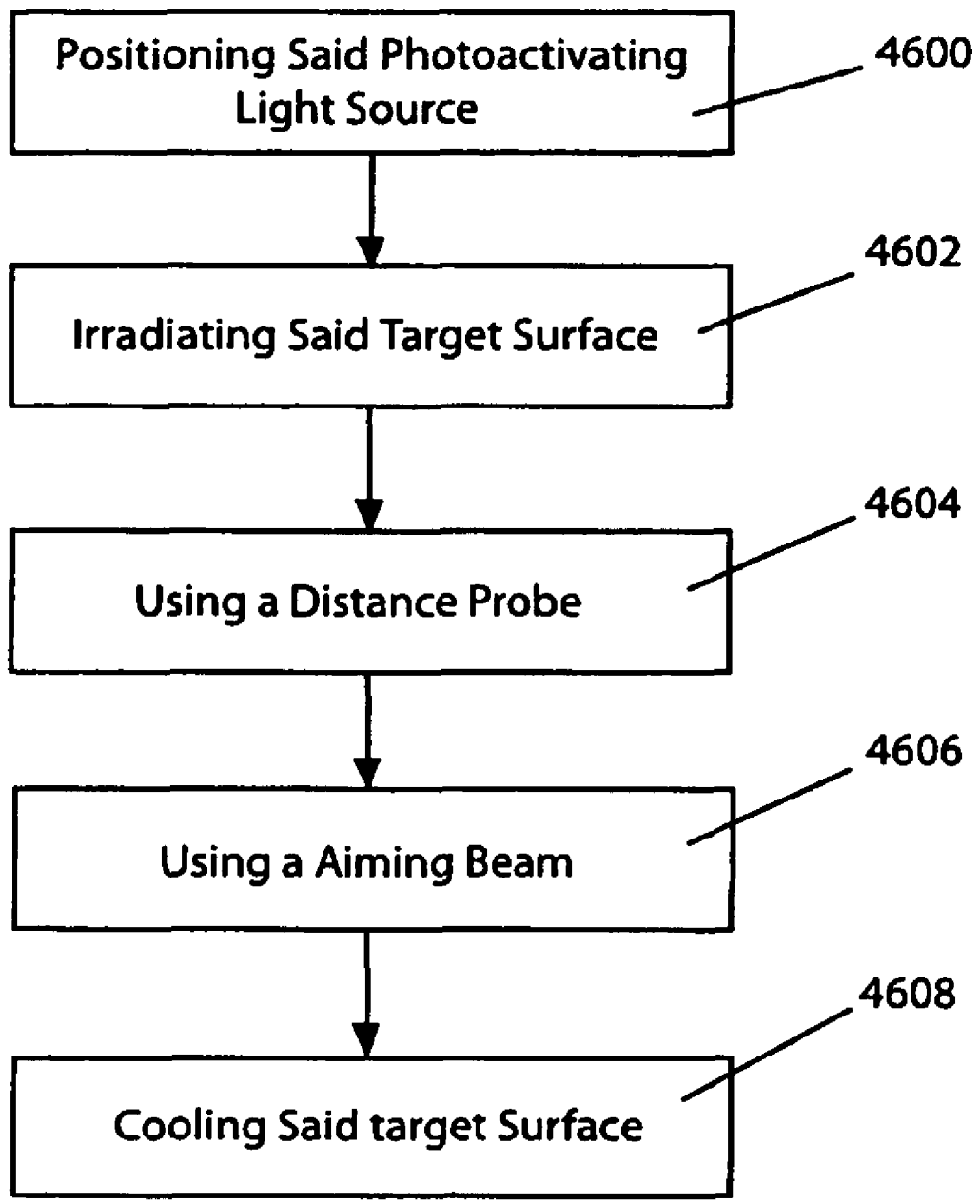
FIG. 46 is a flow chart illustrating a method of use of the present device.

FIG. 46 illustrates method of photoactivating mammalian tissue using a photoactivating device. The photoactivating device includes a photoactivating light source adapted to generate a photoactivating beam of light having a predetermined set of light parameters. All of the parameters are discussed above in detail. The mammalian tissue defines a target surface adapted to be irradiated by the photoactivating beam of light. The method includes the steps of positioning the photoactivating light source and the mammalian tissue relative to each other so that the photoactivating light source and the target surface are at a predetermined operational distance relative to each other (step 4600). Once positioned, irradiating the target surface with the photoactivating beam of light while the photoactivating light source is spaced from the target surface by the operational distance (step 4602). Typically, the operational distance is such that the photoactivating beam of light photoactivates the biological tissue.

Another embodiment includes using a distance probe for adjusting the distance between the photoactivating light source and the target surface towards the operational distance (step 4604). Alternately or in conjunction with, an operator can use an aiming beam of light emanating from an aiming device operatively coupled to the photoactivating light source for aiming the photoactivating light source towards the target surface prior to using the distance probe for adjusting the distance between the photoactivating light source and the target surface towards the operational distance (step 4606).

Further embodiments include cooling the target surface so as to maintain the target surface at a temperature below a predetermined thermal threshold (step 4608). The cooling step can also use a cooling flow of air for convectively cooling the target surface (step 4610). Additionally, the cooling step can also cool the photoactivating light source (step 4612).

Figure 47:
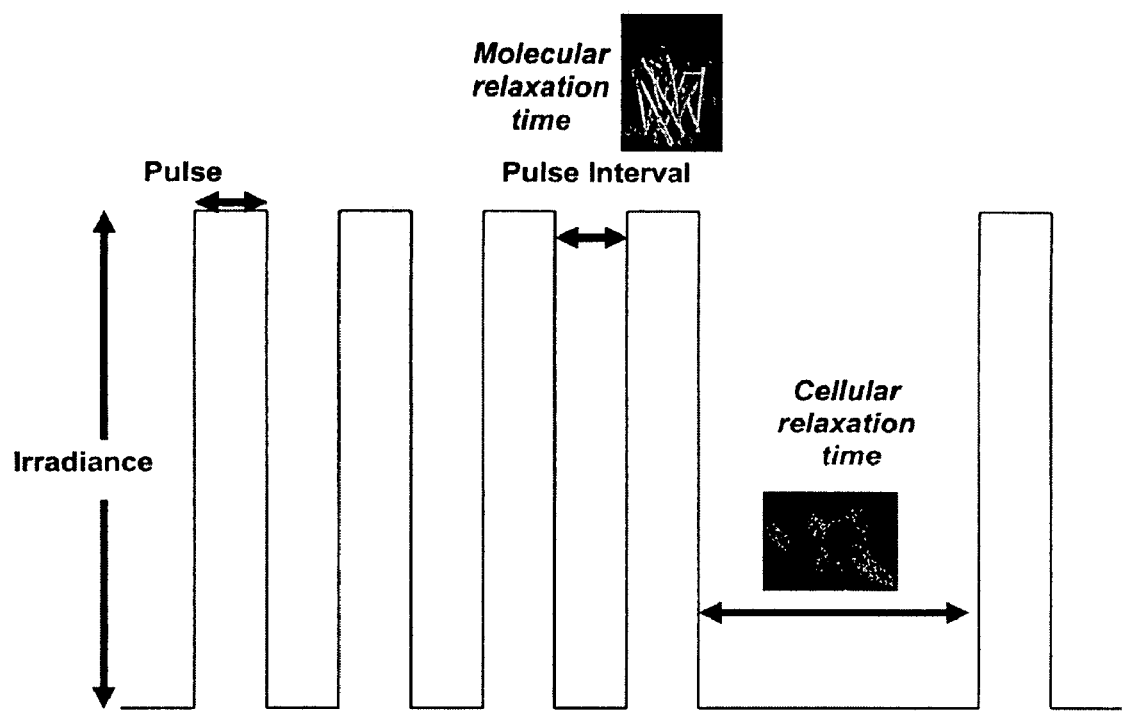
FIG. 47 is a graph of irradiance vs. time illustrating the occurrence of molecular and cellular relaxation during a typical pulsing pattern in accordance with the present invention.

FIG. 47 illustrates an irradiance verses time graph of pulse intervals. The figure illustrates the pulse duration, pulse interval and, importantly, the cellular relaxation time.

Although the present invention has been described hereinabove by way of preferred embodiments thereof, it can be modified, without departing from the spirit and nature of the subject invention as defined in the appended claims.

ENDNOTES

1. Karu, T. (1988). Molecular mechanism of the therapeutic effect of low-intensity laser radiation. Lasers in Life Science 2, 53-74
2. Smith, K. C. (ed.) (1989). The Science of Photobiology, 2nd edn. Plenum Press, NY
3. Walker, J. B., Akhanjee, L. K., Cooney, M. M., Goldstein, J., Tamayoshi, S. and Segal-Gidan, F. (1988). Laser therapy for pain of trigeminal neuralgia. Clinical Journal of Pain 3, 183-187
4. Moore, K. C., Hira, N., Kumar, P. S., Jayakumar, C. S. and Ohshiro, T. (1988). A double blind crossover trial of low level laser therapy in the treatment of postherpetic neuralgia. Laser Therapy 1, 7-9
5. Walker, J. (1983). Relief from chronic pain by low power laser irradiation. Neuroscience Letters 43, 339-344
6. Tyce, G. M., (1985). Biochemistry of serotonin. Serotonin and the Cardiovascular System (ed Canhoutte, P. M.) pp. 1-13, Raven Press, NY
7. Hug, D. H., (1978). The activation of enzymes with light. Photochemical and Photobiological Reviews 3, 1-33
8. Hug, D. H., (1981). Photoactivation of enzymes. Photochemical and Photobiological Reviews 6, 87-138
9. Hug, D. H., (1991). Photobioinduction of enzymes. Journal of Photochemistry and Photobiology in press
10. Saperia, D., Glassberg, E., Lyons, R. F., Abergel, R. P., Baneux, P., Castel, J. C., Dwyer, R. M., and Uitto, J. (1986). Demonstration of elevated Type I and Type II procollagen mRNA levels in cutaneous wounds treated with helium-neon laser. Proposed mechanism for enhanced wound healing. Biochemical and Biophysical Research Communications 138, 1123-1128
11. Smith, K. C. and Hanawalt, P. C. (1969). Molecular Photobiology, Academic Press, NY
12. Abergel, R. P., Meeker, C. A., Lam, T. S., Dwyer, R. M., and Uitto, J. (1984). Control of connective tissue metabolism by lasers: recent developments and future prospects. Journal of the American Academy of Dermatology 11, 1142-1150
13. Lam, T. S., Abergel, R. P., Meeker, C. A., Castel, J. C., Dwyer, R. M., and Uitto, J. (1986). Laser stimulation of collagen synthesis in human skin fibroblast cultures. Lasers in Life Science 1, 61-77
14. Walker, J. B., Akhanjee, L. K., Cooney, M. M., Goldstein, J., Tamayoshi, S. and Segal-Gidan, F. (1987). Laser therapy for pain of rheumatoid arthritis. Clinical Journal of Pain 3, 54-59
15. Goldman, J. A., Chiapella, J., Casey, H., et al. (1980). Laser therapy of rheumatoid arthritis. Lasers in Surgery and Medicine 1, 93-101
16. Whitfield, J. F., Boynton, A. L., MacManus, J. P., Rixon, R. H., Sikorska, M., Tsang, B., Walker, P. R., and Swierenga, S. H. H. (1980). The roles of calcium and cyclic AMP in cell proliferation. Growth Regulation by Ion Fluxes (ed. Leffert, H. I.) Annals of the New York Academy of Sciences 339, 216-240
17. Watson, J. D., Hopkins, N. H., Roberts, J. W., Steitz, J. A., and Weiner, A. M. (1987). Molecular Biology of the Gene 4th edn, Vol II, Chapter 25, The Control of Cell Proliferation, pp. 962-1005. Benjamin/Cummings, Menlo Park, Calif.
18. Agency for Health Care Policy and Research. Treatment of pressure ulcers; clinical guideline number 15. *AHCPR Publication No.* 95-0652 1994; 1-125.
19. Basford J R. Low intensity laser therapy: still not an established clinical tool. *Lasers in Surgery & Medicine* 1995. 1995(16):331-42.
20. Bihari I, Mester A R. The biostimulative effect of low level laser therapy of long-standing crural ulcers using helium neon laser, helium neon plus infrared lasers, and noncoherent light: preliminary report of a randomized double-blind comparative study. *Laser Therapy* 1989; 1(2):97-8.
21. Bradley M, Nelson E A, Petticrew M, et al. Wound dressings for the treatment of pressure sores (Protocol for a Cochrane Review). In *The Cochrane Library*, Issue 2, 1999. Oxford: Update Software.
22. Cambier D C, Vanderstraeten G. Low-level laser therapy: The experience in Flanders. *European Journal of Physical Medicine & Rehabilitation* 1997(7):102-5.
23. Cho C Y, Lo J S. Dressing the part. *Dermatology Clinics* 1998(16):25-47.
24. Crous L, Malherbe C. Laser and ultraviolet light irradiation in the treatment of chronic ulcers. *Physiotherapy* 1988 (44):73-7.
25. Cullum N, Roe B. *Leg ulcers.* Jan. 1, 1995: 1$^{st}$ edition. Scutari Projects, Royal College of Nursing. Middlesex, U.K.
26. Falanga V. Special issue on wound healing: An overview. *Journal of Dermatologic Surgery & Oncology.* 1993(19): 689-90.

27. Flemming K, Cullum N. Laser therapy for the treatment of venous leg ulcers (Cochrane Review). In *The Cochrane Library*, Issue 1, 1999. Oxford: Update Software.
28. Galletti G. Low power laser therapy: a non-invasive highly effective therapeutic modality. *Laser Therapy* 1997; 9: 131-36.
29. Gogia P P. Physical therapy modalities for wound management. *Ostomy Wound Management* 1996; 42(1):46-8.
30. Gogia P P. Physical therapy intervention in wound management. In: *Chronic Wound Care* 2nd ed. Wayne, Pa.: Health Management Publications, Inc. 1997:251-59.
31. Gogia P P, Marquez R R. Effects of helium-neon laser on wound healing. *Ostomy Wound Management* 1992; 38(6): 38-41.
32. Gupta A K, Filonenko N, Salansky N, et al. The use of low energy photon therapy (LEPT) in venous leg ulcers: a double-blind, placebo-controlled study. *Dermatologic Surgery* 1998; 24(12):1383-86.
33. Jovell A J, Navarro-Rubio M D. Evaluacion de la evidencia cientifica. *Medicina Clinica* 1995(105):740-43.
34. Kane D, Krasner D. Wound healing and wound management. In: *Chronic Wound Care* 2nd ed. Wayne, Pa.: Health Management Publications, Inc. 1997:1-4.
35. Keast D H, Orsted H. The basic principles of wound care. *Ostomy Wound Management* 1998; 44(8):24-31.
36. Kleinman Y, Simmer S, Braksma Y, et al. Low level laser therapy in patients with venous ulcers: early and long-term outcome. *Laser Therapy* 1996(8):205-8.
37. Landau Z. Topical hyperbaric oxygen and low energy laser for the treatment of diabetic foot ulcers. *Archives of Orthopaedic & Trauma Surgery* 1998(117):156-58.
38. Lundeberg T, Maim M. Low-power HeNe laser treatment of venous leg ulcers. *Annals of Plastic Surgery* 1991:27(6): 537-39.
39. Malm M, Lundeberg T. Effect of low power gallium arsenide laser on healing of venous ulcers. *Scandinavian Journal of Plastic & Reconstructive Surgery & Hand Surgery* 1991; 25(3):249-51.
40. Mitton C, Hailey D. *Hyperbaric oxygen treatment in Alberta*. Edmonton. Alberta Heritage Foundation for Medical Research, April 1998.
41. Nussbaum E L, Biemann I, Mustard B. Comparison of ultrasound/ultraviolet-C and laser for treatment of pressure ulcers in patients with spinal cord injury. *Physical Therapy* 1994(74):812-23.
42. Ovington L G. Dressings and adjunctive therapies: AHCPR Guidelines Revisited. *Ostomy Wound Management* 1999; 45(1A (Suppl)):94S-106S.
43. Regional Wound Care Guidelines Working Group CHA. Regional wound care guidelines. Edmonton. Capital Health Authority, 1998.
44. Scottish intercollegiate guidelines network (SIGN). The care of patients with chronic leg ulcer. *A National Clinical Guideline* 1998. Edinburgh, U.K. SIGN Secretariat, Royal College of Physicians.
45. Shuttleworth E, Banfield K. Wound care. light relief, low-power laser therapy. *Nursing Times* 1997(93):74-78.
46. Singer A J, Clark R A F. Cutaneous wound healing. *New England Journal of Medicine* 1999; 341(10):738-46.
47. Telfer J, Filonenko N, Salansky N. Low energy laser therapy for leg ulcers [Abstract]. *Lasers in Surgery & Medicine*. 1993.
48. University of Delaware PTGs. Lasers and physical therapy care. http://copland.udel.edu/~17179/index1.htm Aug. 1, 1999.
49. Webb C, Dyson M, Lewis W H. Stimulatory effect of 660 nm low level laser energy on hypertrophic scar-derived fibroblasts: possible mechanisms for increase in cell counts. *Lasers in Surgery and Medicine* 1998(22):294-301.
50. Wheeland R G. Lasers for the stimulation or inhibition of wound healing. *Journal of Dermatologic Surgery & Oncology* 1993(19):747-52.
51. Zhang C and Wong-Riley M. Depolarization stimulation upregulates GA-binding protein in neurons: a transcription factor involved in the bigenomic expression of cytochrome oxidase subunits. Eur J Neurosci 12, 1013-1023 (2000a).
52. Zhang C and Wong-Riley M. Synthesis and degradation of cytochrome oxidase subunit mRNAs in neurons: Differential bigenomic regulation by neuronal activity. J Neurosci Res 60, 338-344 (2000b).
53. Wong-Riley, M. T. Bai, X. Buchmann, E. Whelan, H. T. "Light-emitting diode treatment reverses the effect of TTX on cytochrome oxidase in neurons" Neurochemistry. 12(14):3033-7, 2001.
54. Whelan, H. T. Smits, R. L. Buchmann, E. V. Whelan, N. T. Turner, S. G. Margolis, D. A. Cevenini, V. Stinson, H. Ignatius, R. Martin, T. Cwiklinski, J. Philippi, A. F. Graf, W. R. Hodgson, B. Gould, L. Kane, M. Chen, G. Caviness, J. "Effect of NASA light-emitting diode (LED) irradiation on wound healing" Journal of Clinical Laser Medicine & Surgery. 19(6):305-13, 2001.
55. Goldman, M., Cutaneous laser surgery: The art and science of selective photothermolysis. 2nd edition, Mosby, pp. 8-9.
56. Anderson R R, Parrish J A: Selective photothermolysis: precise microsurgery by selective absorption of pulsed radiation, Science 220:524, 1983.
57. Sommer A P et al., Biostimulatory windows in low-intensity laser activation: Lasers, Scanners, and NASA's Light-Emitting Diode Array System, J of Clin Laser Med & Surg, vol 19:1; 2001, pp 29-33.
58. Young S R et al., Effect of light on calcium uptake by macrophages, Laser Ther. 1991: 3, 1-5.
59. Karu T et al., Changes in oxidative metabolism of murine spleen following laser and superluminous diode (660-950 nm) irradiation: effects of cellular composition and radiation parameters. Lasers Surg. Med., 193:13, 453-462.
60. Friedman P M, Skover G R, Payonk G, et al. 3D in-vivo optical skin imaging for topographical quantitative assessment of non-ablative laser technology. Dermatol Surg. 2002 March; 28(3):199-204.
A1) Webb C, Dyson M, Lewis W H. Stimulatory effect of 660 nm low level laser energy on hypertrophic scar-derived fibroblasts: possible mechanisms for increase in cell counts. Lasers Surg Med 1998; 22(5):294-301.
A2) Harper R A, Grove G. Human skin fibroblasts derived from papillary and reticular dermis: differences in growth potential in vitro. Science 1979 May 4; 204(4392):526-7.
A3) Schonherr E, Beavan L A, Hausser H, et al. Differences in decorin expression by papillary and reticular fibroblasts in vivo and in vitro. Biochem J 1993 Mar. 15; 290 (Pt 3):893-9.
A4) Karu, T. Molecular mechanism of the therapeutic effect of low-intensity laser radiation. Lasers in Life Science 1988; 2, 53-74.
A5) Auger F. A., Rémy-Zolghadri M., Grenier G., Germain L.: "A truly New Approach For Tissue Engineering The LOEX Self-Assembly Technique". In: Stem cell transplantation and tissue engineering, A. Haverich, H. Graf, eds, Springer-Verlag, Berlin. Chapter 6: 73-88, 2002.
A6) Germain L., Moulin V., Berthod F., Lopez C. A., Goulet F., Auger F. A.: "Multiple applications of tissue-engineered human skin". In: Cultured human keratinocytes and tissue engineered skin substitutes R. E. Horch, A. M. Munster, B. M. Achauer, eds. Georg Thieme Verlag, Stuttgart, Germany. pp. 91-98, 2001.

A7) Simpson C R, Kohl M, Essenpreis M, Cope M. Near infrared optical properties of ex-vivo human skin and subcutaneous tissues measured using the Monte Carlo inversion technique. Phys Med Biol 1998 43: 2465-2478.

B1) Privalov P L. Stability of proteins. Proteins which do not present a single cooperative system. Adv Protein Chem. 1982; 35:1-104.

B2) Piez K A. Structure and assembly of the native collagen fibril. Connect Tissue Res. 1982; 10(1):25-36.

B3) Chi-Hyun P., Min J L., Jungmi A., Sangmin K., Hyeon H K, Kyu H K., Hee C E., and Jin H C. Heat Shock-Induced Matrix Metalloproteinase (MMP)-1 and MMP-3 Are Mediated through ERK and JNK Activation and via an Autocrine Interleukin-6 Loop J Invest Dermatol 2004, 123: 6, 1012-1019.

B4) Chen Z, Seo J Y, Kim Y K, Lee S R, Kim K H, Cho K H, Eun H C, Chung J H. Heat modulation of tropoelastin, fibrillin-1, and matrix metalloproteinase-12 in human skin in vivo. J Invest Dermatol. 2005 January; 124(1):70-8.

B5) Chung J H, Seo J Y, Choi H R, Lee M K, Youn C S, Rhie G, Cho K H, Kim K H, Park K C, Eun H C. Modulation of skin collagen metabolism in aged and photoaged human skin in vivo. J Invest Dermatol. 2001 November; 117(5): 1218-24.

B6) Varani J, Spearman D, Perone P, Fligiel S E, Datta S C, Wang Z Q, Shao Y, Kang S, Fisher G J, Voorhees J J. Inhibition of type I procollagen synthesis by damaged collagen in photoaged skin and by collagenase-degraded collagen in vitro. Am J Pathol. 2001 March; 158(3):931-42.

B7) Fligiel S E, Varani J, Datta S C, Kang S, Fisher G J, Voorhees J J. Separation of retinoid-induced epidermal and dermal thickening from skin irritation. J Invest Dermatol. 2003 May; 120(5):842-8.

We claim:

1. A photoactivation device for modulating the physiology of a target biological activity by directing a photoactivating beam of light having a predetermined set of photoactivating light parameters on a target surface, said device comprising:
   a treatment head defining a central head section and a pair of laterally disposed lateral head sections, said central head section and each of said lateral head sections comprising rows of corresponding substantially elongated photoactivating light sources, in substantially side-by-side and contiguous relationships relative to each other, and emitting said photoactivating beam of light;
   wherein said photoactivating beam of light is a pulsed photoactivating beam of light having a target irradiance of at least about 10 mW/cm$^2$ and at most about 1000 mW/cm$^2$ and configured to be pulsed according to a pulsing scheme stimulating collagen production in said target, said target irradiance being substantially constant throughout a lighting range over which said target is illuminated;
   said treatment head further comprising:
      a positioning element operatively coupled to said photoactivating light sources for allowing selective positioning of said photoactivating light sources relative to said target surface; and
      a position evaluating element for evaluating the position of said photoactivating light sources relative to said target surface, by allowing for an evaluation of the distance between said photoactivating light sources and said target surface, said position evaluating element comprising:
         a non-contacting distance probe light source projecting a probe light ray along a projection optical axis towards said target surface; and
         a non-contacting distance probe target sensor sensing said probe light ray traveling along a target sensor optical axis once said probe light ray has been reflected by said target surface;
         wherein said distance probe light source and said distance probe target sensor are configured, sized and positioned so that said projection optical axis and said target sensor optical axis are angled relative to each other and intercept each other on said target surface substantially only when said target surface is spaced from said photoactivating light sources by a predetermined target-to-photoactivating light source spacing distance; and
         wherein, according to the position of said photoactivating light sources relative to said target surface evaluated with said position evaluating element, said positioning element is operable to selectively position said photoactivating light sources relative to said target surface to achieve a predetermined operational characteristic of said photoactivating light sources resulting in said target irradiance; and
      an information providing element for providing information regarding the position of said photoactivating light sources relative to said target surface, said information providing element including a visual display component for providing a visual display indicative of the position of said photoactivating light sources relative to said target surface.

2. A device as recited in claim 1 wherein said information providing element includes a direction indicator for providing information regarding the direction in which said photoactivating light sources should be moved to reach a predetermined target position relative to said target surface.

3. A device as recited in claim 1 further comprising an actuator for taking a predetermined course of action depending on the position of said photoactivating light sources relative to said target surface, said actuator including a positioner for automatically repositioning said photoactivating light sources towards a predetermined target position relative to said target surface.

4. A device as recited in claim 1 further comprising an aiming element operatively coupled to said position evaluating element for allowing aiming of said position evaluating element towards a target position located on said target surface.

5. A device as recited in claim 1 further comprising:
   a distance probe offset sensor for sensing said probe light ray when said probe light travels along an offset sensor optical axis;
   wherein said distance probe light source and said distance probe offset sensor are configured, sized and positioned so that said probe light ray is reflected from said target surface so as to travel along said offset sensor optical axis when said photoactivating light sources are spaced from said target surface by an offset spacing distance substantially different from said predetermined target-to-photoactivating light source spacing distance; and
   wherein when said photoactivating light sources are spaced from said target surface by said offset spacing distance, said offset sensor optical axis and said projection optical axis are angled relative to each other and intercept each other substantially on said target surface allowing said distance probe offset sensor to sense said probe light ray.

6. A device as recited in claim 1 further comprising:
a distance probe near sensor for sensing said probe light ray when said probe light ray travels along a near sensor optical axis; and
a distance probe far sensor for sensing said probe light ray when said probe light ray travels along a far sensor optical axis;
wherein said distance probe light source and said distance probe near sensor are configured, sized and positioned so that said probe light ray is reflected from said target surface so as to travel along said near sensor optical axis when said photoactivating light sources are spaced from said target surface by a near spacing distance substantially smaller then than said predetermined target-to-photoactivating light source spacing distance;
wherein said distance probe light source and said distance probe far sensor are configured, sized and positioned so that said probe light ray is reflected from said target surface so as to travel along said far sensor optical axis when said photoactivating light sources are spaced from said target surface by a far spacing distance substantially greater than said predetermined target-to-photoactivating light source spacing distance; and
wherein when said photoactivating light sources are spaced from said target surface by said near spacing distance, said near sensor optical axis and said projection optical axis are angled relative to each other and intercept each other substantially on said target surface allowing said distance probe near sensor to sense said probe light ray and, when said photoactivating light sources are spaced from said target surface by said far spacing distance, said far sensor optical axis and said projection optical axis are angled relative to each other and intercept each other substantially on said target surface allowing said distance probe far sensor to sense said probe light ray.

7. A device as recited in claim 6 wherein,
said distance probe light source and said distance probe target sensor are configured, sized and positioned so that said probe light ray is reflected from said target surface so as to travel along said target sensor optical axis when said photoactivating light sources are spaced from said target surface by a predetermined target-to-photoactivating light source spacing distance located within a predetermined target spacing range;
said distance probe light source and said distance probe near sensor are configured, sized and positioned so that said probe light ray is reflected from said target surface so as to travel along said near sensor optical axis when said photoactivating light sources are spaced from said target surface by a near spacing distance located within a predetermined near spacing range;
said distance probe light source and said distance probe far sensor are configured, sized and positioned so that said probe light ray is reflected from said target surface so as to travel along said far sensor optical axis when said photoactivating light sources are spaced from said target surface by a far spacing distance located within a predetermined far spacing range; and
said near, far and target spacing ranges are substantially contiguous relative to each other so as to form a substantially continuous operational spacing range.

8. A device as recited in claim 1 wherein said distance probe light source allows for the emission of said probe light ray with the latter having a frequency located within the infra-red spectrum.

9. A device as recited in claim 1 further comprising an aiming element operatively coupled to said position evaluating element for allowing aiming of said probe light ray towards a target position located on said target surface, said aiming element including a visible aiming beam of light for visibly pointing towards said target position.

10. A device as recited in claim 1 wherein said optical probe includes an optical probe casing for protectively enclosing said distance probe light source and said distance probe target sensor; said optical probe casing including a light source cavity for protectively receiving at least part of said distance probe light source and a target sensor cavity for protectively receiving at least part of said distance probe target sensor.

11. A device as recited in claim 10 further comprising a light source alignment element for allowing adjustment of the direction of said projection optical axis relative to said optical probe casing.

12. A device as recited in claim 10 wherein said optical probe casing defines a casing input end and a substantially opposed casing output end; said light source cavity having a generally elongated configuration and extending through said optical probe casing substantially from said casing input end to said casing output end; said distance probe light source being mounted on a probe light source mounting component; said light source cavity having a light source mounting section located substantially adjacent to said casing input end for receiving said light source mounting component and allowing selective movement thereof within said light source mounting section.

13. A device as recited in claim 12 wherein said light source cavity defines a cavity longitudinal axis and wherein said light source mounting section is configured and sized for allowing selective movement of said light source mounting component therein along a substantially arc-shaped adjustment trajectory.

14. A device as recited in claim 13 wherein said probe light source mounting component includes a substantially cylindrical light source receiving channel for receiving said distance probe light source and a pair of substantially radial mounting component guiding flanges; said probe light source mounting component defining a pair of opposed and substantially flat mounting component guiding surfaces, at least one of said mounting component guiding surfaces being provided with a corresponding guiding tongue extending substantially outwardly therefrom; said optical probe casing defining a pair of opposed probe casing main walls extending in a spaced apart relationship relative to each other between said casing input end and said casing output end; at least one of said probe casing main walls having a guiding groove formed therein for guidingly receiving said corresponding guiding tongue.

15. A device as recited in claim 13 wherein said optical probe casing defines a casing input end and a substantially opposed casing output end; said light source cavity extending through said optical probe casing substantially from said casing input end to said casing output end; said light source cavity having a substantially frusto-conical configuration tapering towards said casing output end.

16. A photoactivation device as recited in claim 1 wherein said positioning element and said position evaluating element are configured and sized for being operative respectively with the forehead and the lateral periorbital regions of a human face.

17. A photoactivation device as recited in claim 1 further comprising a pair of focusing light sources operatively coupled to said treatment head, said focusing light sources being positioned and angled relative to said treatment head so as to project onto said target surface a corresponding pair of focusing marks, said focusing marks being in register with each other only when said treatment head is at a predetermined target distance from said target surface.

18. A photoactivation device as recited in claim 1 wherein at least one of said photoactivating light sources includes a matrix of light emitting diodes.

19. A device as recited in claim 1 wherein the photoactivating beam of light has a target irradiance of between about 30 mW/cm2 and about 100 mW/cm2.

* * * * *